US012674212B2

(12) United States Patent
Li et al.

(10) Patent No.: US 12,674,212 B2
(45) Date of Patent: Jul. 7, 2026

(54) PCR METHOD FOR THE DETECTION OF EQUINE ROTAVIRUS GROUP B (ERVB) IN BIOLOGICAL SAMPLES

(71) Applicant: University of Kentucky Research Foundation, Lexington, KY (US)

(72) Inventors: Feng Li, Lexington, KY (US); Dan Wang, Lexington, KY (US); Erdal Erol, Lexington, KY (US); Tirth Uprety, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 1133 days.

(21) Appl. No.: 17/712,012

(22) Filed: Apr. 1, 2022

(65) Prior Publication Data

US 2022/0325364 A1 Oct. 13, 2022

Related U.S. Application Data

(60) Provisional application No. 63/196,152, filed on Jun. 2, 2021, provisional application No. 63/169,645, filed on Apr. 1, 2021.

(51) Int. Cl.
C12Q 1/70 (2006.01)
C12Q 1/686 (2018.01)

(52) U.S. Cl.
CPC ............. *C12Q 1/701* (2013.01); *C12Q 1/686* (2013.01); *C12N 2720/12321* (2013.01)

(58) Field of Classification Search
CPC .................... C12Q 1/686; C12Q 1/701; C12N 2720/12321
See application file for complete search history.

(56) References Cited

U.S. PATENT DOCUMENTS 9,089,619 B2 7/2015 Li

OTHER PUBLICATIONS

Marthaler, D., et al., 2012, Detection of substantial porcine group B rotavirus genetic diversity in the United States, resulting in a modified classification proposal for G genotypes, Virol. 422:85-96.*
Otto, P. H., et al., 2015, Detection of rotavirus species A, B, and C in domestic mammalian animals with diarrhoea adn genotyping of bovine species A rotavirus strains, Vet. Microbiol. 179:168-176.*
Troeger C, Khalil IA, Rao PC, et al. Rotavirus Vaccination and the Global Burden of Rotavirus Diarrhea Among Children Younger Than 5 Years. JAMA pediatrics. Oct. 1, 2018;172(10):958-965.
Dhama K, Chauhan RS, Mahendran M, et al. Rotavirus diarrhea in bovines and other domestic animals. Vet Res Commun. Jan. 2009;33(1):1-23.
Anderson EJ, Weber SG. Rotavirus infection in adults. Lancet Infect Dis. Feb. 2004;4(2):91-9.

Crawford SE, Ramani S, Tate JE, et al. Rotavirus infection. Nat Rev Dis Primers. Nov. 9, 2017;3(1):17083.
Hu L, Crawford SE, Hyser JM, et al. Rotavirus non-structural proteins: structure and function. Curr Opin Virol. Aug. 2012;2(4):380-8.
Trojnar E, Otto P, Roth B, et al. The genome segments of a group D rotavirus possess group A-like conserved termini but encode group-specific proteins. J Virol. Oct. 2010;84(19):10254-65.
Zhang X, Settembre E, Xu C, et al. Near-atomic resolution using electron cryomicroscopy and single-particle reconstruction. 2008; 105(6):1867-1872.
Tang B, Gilbert JM, Matsui SM, et al. Comparison of the rotavirus gene 6 from different species by sequence analysis and localization of subgroup-specific epitopes using site-directed mutagenesis. Virology. Oct. 13, 1997;237(1):89-96.
Matthijnssens J, Otto PH, Ciarlet M, et al. VP6-sequence-based cutoff values as a criterion for rotavirus species demarcation. Arch Virol. Jun. 2012;157(6):1177-82.
Walker PJ, Siddell SG, Lefkowitz EJ, et al. Changes to virus taxonomy and the International Code of Virus Classification and Nomenclature ratified by the International Committee on Taxonomy of Viruses (2019). Arch Virol. Sep. 2019;164(9):2417-2429.
Hoshino Y, Kapikian AZ. Classification of rotavirus VP4 and VP7 serotypes. Archives of virology Supplementum. 1996;12:99-111.
Van der Heide R, Koopmans MP, Shekary N, et al. Molecular characterizations of human and animal group a rotaviruses in the Netherlands. J Clin Microbiol. Feb. 2005;43(2):669-75.
Trovao NS, Shepherd FK, Herzberg K, et al. Evolution of rotavirus C in humans and several domestic animal species. Zoonoses Public Health. Aug. 2019;66(5):546-557.
Deol P, Kattoor JJ, Sircar S, et al. Avian Group D Rotaviruses: Structure, Epidemiology, Diagnosis, and Perspectives on Future Research Challenges. Pathogens. Oct. 24, 2017;6(4):53.

(Continued)

*Primary Examiner* — Jeffrey S Parkin
(74) *Attorney, Agent, or Firm* — Stites & Harbison PLLC; Mandy Wilson Decker

(57) ABSTRACT

Provided herein are a set of primers and probes for detecting rotavirus. The set of primers and probes includes at least one forward primer selected from the group including SEQ ID NOS: 17, 20, 23, 26, 29, 32, 35, 38, 41, 44, 47, 50, 53, 56, 59, 62, 65, 68, 71, 74, 77, 80, 83, 86, 89, 92, 95, 98, 101, 104, 107, 110, 113, 116, 119, 122, 125, 128, 131, 134, 137, 140, 143, 146, 149, 152, 155, 158, 161, 164, 167, 204, 207, 210, and combinations thereof; at least one reverse primer selected from the group including SEQ ID NOS: 18, 21, 24, 27, 30, 33, 36, 39, 42, 45, 48, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153, 156, 159, 162, 165, 168, 205, 208, 211, and combinations thereof; and at least one probe selected from the group including SEQ ID NOS: 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151, 154, 157, 160, 163, 166, 169, 206, 209, 212, and combinations thereof. Also provided herein is a method for detecting rotavirus using the set of primers and probes.

4 Claims, 12 Drawing Sheets

Specification includes a Sequence Listing.

(56)            References Cited

OTHER PUBLICATIONS

Sanekata T, Ahmed MU, Kader A, et al. Human group B rotavirus infections cause severe diarrhea in children and adults in Bangladesh. J Clin Microbiol. May 2003;41(5):2187-90.

Chang KO, Parwani AV, Smith D, et al. Detection of group B rotaviruses in fecal samples from diarrheic calves and adult cows and characterization of their VP7 genes. J Clin Microbiol. Aug. 1997;35(8):2107-10.

Nguyen TA, Khamrin P, Trinh QD, et al. Sequence analysis of Vietnamese P[6] rotavirus strains suggests evidence of interspecies transmission. J Med Virol. Dec. 2007;79(12):1959-65.

Cook N, Bridger J, Kendall K, et al. The zoonotic potential of rotavirus. J Infect. May 2004;48(4):289-302.

Muller H, Johne R. Rotaviruses: diversity and zoonotic potential—a brief review. Berl Munch Tierarztl Wochenschr. Mar.-Apr. 2007;120(3-4):108-12.

Martella V, Banyai K, Matthijnssens J, et al. Zoonotic aspects of rotaviruses. Vet Microbiol. Jan. 27, 2010;140 (3-4):246-55.

Mukherjee A, Mullick S, Deb AK, et al. First report of human rotavirus G8P[4] gastroenteritis in India: evidence of ruminants-to-human zoonotic transmission. J Med Virol. Mar. 2013;85(3):537-45.

Mukherjee A, Dutta D, Ghosh S, et al. Full genomic analysis of a human group A rotavirus G9P[6] strain from Eastern India provides evidence for porcine-to-human interspecies transmission. Arch Virol. 2009;154(5):733-46.

Komoto S, Tacharoenmuang R, Guntapong R, et al. Reassortment of Human and Animal Rotavirus Gene Segments in Emerging DS-1-Like G1P[8] Rotavirus Strains. PLoS One. 2016;11(2):e0148416.

Chen F, Knutson TP, Ciarlet M, et al. Complete genome characterization of a rotavirus B (RVB) strain identified in Alpine goat kids with enteritis reveals inter-species transmission with RVB bovine strains. J Gen Virol. Apr. 2018;99 (4):457-463.

Miño S, Adúriz M, Barrandeguy M, et al. Molecular Characterization of Equine Rotavirus Group A Detected in Argentinean Foals During 2009-2014. Journal of Equine Veterinary Science. 2017 Dec. 1, 2017;59:64-70.

Hoshino Y, Wyatt RG, Greenberg HB, et al. Serotypic similarity and diversity of rotaviruses of mammalian and avian origin as studied by plaque-reduction neutralization. J Infect Dis. May 1984;149(5):694-702.

Browning GF, Fitzgerald TA, Chalmers RM, et al. A novel group A rotavirus G serotype: serological and genomic characterization of equine isolate FI23. J Clin Microbiol. Sep. 1991;29(9):2043-6.

Imagawa H, Tanaka T, Sekiguchi K, et al. Electropherotypes, serotypes, and subgroups of equine rotaviruses isolated in Japan. Arch Virol. 1993;131(1-2):169-76.

Isa P, Wood AR, Netherwood T, et al. Survey of equine rotaviruses shows conservation of one P genotype in background of two G genotypes. Arch Virol. 1996;141(9):1601-12.

Imagawa H, Ishida S, Uesugi S, et al. Genetic analysis of equine rotavirus by RNA-RNA hybridization. J Clin Microbiol. Aug. 1994;32(8):2009-12.

Browning GF, Chalmers RM, Fitzgerald TA, et al. Serological and genomic characterization of L338, a novel equine group A rotavirus G serotype. J Gen Virol. May 1991;72 ( Pt 5):1059-64.

Hardy ME, Gorziglia M, Woode GN. The outer capsid protein VP4 of equine rotavirus strain H-2 represents a unique VP4 type by amino acid sequence analysis. Virology. Mar. 1993;193(1):492-7.

Isa P, Snodgrass DR. Serological and genomic characterization of equine rotavirus VP4 proteins identifies three different P serotypes. Virology. Jun. 1994;201(2):364-72.

Collins PJ, Cullinane A, Martella V, et al. Molecular characterization of equine rotavirus in Ireland. J Clin Microbiol. Oct. 2008;46(10):3346-54.

Carossino M, Barrandeguy ME, Li Y, et al. Detection, molecular characterization and phylogenetic analysis of G3P[12] and G14P[12] equine rotavirus strains co-circulating in central Kentucky. Virus Res. Aug. 15, 2018;255:39-54.

Athiyyah AF, Utsumi T, Wahyuni RM, et al. Molecular Epidemiology and Clinical Features of Rotavirus Infection Among Pediatric Patients in East Java, Indonesia During 2015-2018: Dynamic Changes in Rotavirus Genotypes From Equine-Like G3 to Typical Human G1/G3 [Original Research]. Front Microbiol. 2019 May 3, 2019;10(940):940.

Ghosh S, Shintani T, Kobayashi N. Evidence for the porcine origin of equine rotavirus strain H-1. Vet Microbiol. Aug. 17, 2012;158(3-4):410-4.

Mino S, Matthijnssens J, Badaracco A, et al. Equine G3P[3] rotavirus strain E3198 related to simian RRV and feline/canine-like rotaviruses based on complete genome analyses. Vet Microbiol. Jan. 25, 2013;161(3-4):239-46.

Bailey KE, Gilkerson JR, Browning GF. Equine rotaviruses—current understanding and continuing challenges. Vet Microbiol. Nov. 29, 2013;167(1-2):135-44.

Otto PH, Rosenhain S, Elschner MC, et al. Detection of rotavirus species A, B and C in domestic mammalian animals with diarrhoea and genotyping of *bovine* species A rotavirus strains. Vet Microbiol. Sep. 30, 2015;179(3-4):168-76.

Kumar S, Stecher G, Li M, et al. Mega X: Molecular Evolutionary Genetics Analysis across Computing Platforms. Mol Biol Evol. Jun. 1, 2018;35(6):1547-1549.

Shepherd FK, Herrera-Ibata DM, Porter E, et al. Whole Genome Classification and Phylogenetic Analyses of Rotavirus B strains from the United States. Pathogens. Apr. 18, 2018;7(2):44.

Lu X, McDonald SM, Tortorici MA, et al. Mechanism for coordinated RNA packaging and genome replication by rotavirus polymerase VP1. Structure. Nov. 12, 2008;16(11):1678-88.

McDonald SM, Patton JT. Rotavirus VP2 core shell regions critical for viral polymerase activation. J Virol. Apr. 2011;85 (7):3095-105.

Patton JT, Chen D. RNA-binding and capping activities of proteins in rotavirus open cores. J Virol. Feb. 1999;73 (2):1382-91.

Díaz-Salinas MA, Romero P, Espinosa R, et al. The Spike Protein VP4 Defines the Endocytic Pathway Used by Rotavirus to Enter MA104 Cells. 2013;87(3):1658-1663.

Lopez S, Arias CF. Multistep entry of rotavirus into cells: a Versaillesque dance. Trends Microbiol. Jun. 2004;12 (6):271-8.

Greenberg HB, Estes MK. Rotaviruses: from pathogenesis to vaccination. Gastroenterology. May 2009;136 (6):1939-51.

Barro M, Patton JT. Rotavirus NSP1 inhibits expression of type I interferon by antagonizing the function of interferon regulatory factors IRF3, IRF5, and IRF7. J Virol. May 2007;81(9):4473-81.

Eichwald C, Rodriguez JF, Burrone OR. Characterization of rotavirus NSP2/NSP5 interactions and the dynamics of viroplasm formation. J Gen Virol. Mar. 2004;85(Pt 3):625-634.

Elschner M, Schrader C, Hotzel H, et al. Isolation and molecular characterisation of equine rotaviruses from Germany. Vet Microbiol. Jan. 31, 2005;105(2):123-9.

Browning GF, Begg AP. Prevalence of G and P serotypes among equine rotaviruses in the faeces of diarrhoeic foals. Arch Virol. 1996 Jun. 1, 1996;141(6):1077-89.

Tsunemitsu H, Imagawa H, Togo M, et al. Predominance of G3B and G14 equine group A rotaviruses of a single VP4 serotype in Japan. Arch Virol. Oct. 2001;146(10):1949-62.

Eiden JJ, Nataro J, Vonderfecht S, et al. Molecular cloning, sequence analysis, in vitro expression, and immunoprecipitation of the major inner capsid protein of the IDIR strain of group B rotavirus (GBR). Virology. Jun. 1992;188(2):580-9.

Miyabe FM, Dall Agnol AM, Leme RA, et al. Porcine rotavirus B as primary causative agent of diarrhea outbreaks in newborn piglets. Sci Rep. Dec. 15, 2020;10(1):22002.

Hayashi M, Murakami T, Kuroda Y, et al. Reinfection of adult cattle with rotavirus B during repeated outbreaks of epidemic diarrhea. Can J Vet Res. Jul. 2016;80(3):189-96.

Theil KW, Grooms DL, McCloskey CM, et al. Group B rotavirus associated with an outbreak of neonatal lamb diarrhea. J Vet Diagn Invest. Jan. 1995;7(1):148-50.

Joshi MS, Ganorkar NN, Ranshing SS, et al. Identification of group B rotavirus as an etiological agent in the gastroenteritis outbreak in Maharashtra, India. J Med Virol. Dec. 2017;89(12):2244-2248.

(56)         References Cited

OTHER PUBLICATIONS

Krishnan T, Sen A, Choudhury JS, et al. Emergence of adult diarrhoea rotavirus in Calcutta, India. Lancet. Jan. 30, 1999;353(9150):380-1.

Kuga K, Miyazaki A, Suzuki T, et al. Genetic diversity and classification of the outer capsid glycoprotein VP7 of porcine group B rotaviruses. Arch Virol. 2009 Oct. 11, 2009;154(11):1785-95.

Marthaler D, Rossow K, Gramer M, et al. Detection of substantial porcine group B rotavirus genetic diversity in the United States, resulting in a modified classification proposal for G genotypes. Virology. Nov. 10, 2012;433(1):85-96.

Alekseev KP, Penin AA, Mukhin AN, et al. Genome Characterization of a Pathogenic Porcine Rotavirus B Strain Identified in Buryat Republic, Russia in 2015. Pathogens. Apr. 20, 2018;7(2):46.

Papp H, Malik YS, Farkas SL, et al. Rotavirus strains in neglected animal species including lambs, goats and camelids. Virusdisease. 2014;25(2):215-22.

Holland RE. Some infectious causes of diarrhea in young farm animals. 1990;3(4):345-375.

Magdesian KG. Neonatal foal diarrhea. Vet Clin North Am Equine Pract. Aug. 2005;21(2):295-312, vi.

Arana A, Montes M, Jere KC, et al. Emergence and spread of G3P[8] rotaviruses possessing an equine-like VP7 and a DS-1-like genetic backbone in the Basque Country (North of Spain), 2015. Infect Genet Evol. Oct. 2016;44:137-144.

Cowley D, Donato CM, Roczo-Farkas S, et al. Emergence of a novel equine-like G3P[8] inter-genogroup reassortant rotavirus strain associated with gastroenteritis in Australian children. J Gen Virol. Feb. 2016;97(2):403-410.

Perkins C, Mijatovic-Rustempasic S, Ward ML, et al. Genomic Characterization of the First Equine-Like G3P[8] Rotavirus Strain Detected in the United States. Genome Announc. Nov. 22, 2017;5(47):e01341-17.

Martella V, Colombrita D, Lorusso E, et al. Detection of a porcine-like rotavirus in a child with enteritis in Italy. J Clin Microbiol. Oct. 2008;46(10):3501-7.

Jeong S, Than VT, Lim I, et al. Whole-genome analysis of a rare human Korean G3P rotavirus strain suggests a complex evolutionary origin potentially involving reassortment events between feline and bovine rotaviruses. PLoS One. 2014;9(5):e97127.

Dwyer RM. Diarrhea among young foals. Equine Disease Quarterly. Jul. 1995;3(4):5-6.

Masova AN, Amimo JO, Saif LJ. Porcine Rotaviruses: Epidemiology, Immune Responses and Control Strategies. Viruses. Mar. 18, 2017;9(3):48.

Tao H, Changan W, Zhaoying F, et al. Waterborne Outbreak of Rotavirus Diarrhoea in Adults in China Caused by a Novel Rotavirus. The Lancet. 1984;323(8387):1139-1142.

Chen G-M, Hung T, Bridger JC, et al. Chinese Adult Rotavirus Is a Group B Rotavirus. The Lancet. 1985;326 (8464):1123-1124.

Marthaler D, Suzuki T, Rossow K, et al. VP6 genetic diversity, reassortment, intragenic recombination and classification of rotavirus B in American and Japanese pigs. Vet Microbiol. Aug. 27, 2014;172(3-4):359-66.

Freeman MM, Kerin T, Hull J, McCaustland K, Gentsch J. Enhancement of detection and quantification of rotavirus in stool using a modified real-time RT-PCR assay. J Med Virol. Aug. 2008;80(8):1489-96. doi: 10.1002/jmv.21228. PMID: 18551614.

* cited by examiner

A

VP1

A

B

VP6

NSP1

SEQUENCE LISTING

```
<160> NUMBER OF SEQ ID NOS: 212

<210> SEQ ID NO 1
<211> LENGTH: 3481
<212> TYPE: DNA
<213> ORGANISM: Equine rotavirus

<400> SEQUENCE: 1
cataatgatg gccaggctgt ctccacccga gactcagtga aattgaactc gctgtgaaga        60
tgcagtgtac ccgcggcaag acggaaagac cccgtgatat ctgccggagc tctgcagata       120
tcaagtcaat atatacaaat ccaaaaattg cgaaaatagt ttttaaagaa gctgacagac       180
tgtgggaatc gaaaacacta aactcacaga cacccgatga agtgttagat gaaatagaaa       240
aattgaagaa atcaactgaa gatatcgata gtaaactgga aaaattactc aggttaaggt       300
```

-continued

```
atttaaccgt gtatgtagac gataaatctg acaaaagaaa aatagtgttg aaactgatcg      360
ataatgtagt gaatctaaca tctacaggtg acgtattcca ttcaatcagg gctatagaat      420
ttcaagctaa acagtggagg acgaaaaatg cgtctgtgct gaaaccatac cattacaaca      480
taccaatttg tgaatacatt cgagataatg aaattgaata catagatact ggtgattaca      540
aatggcaatc ggatacattg caaggtttga tgccaaatta ttatcacaga acgcatacac      600
tgattggttc agttgtatta tcagttctca aaagaatttc aacatatagt gacgaggaaa      660
agaaagcttt gaactacctg ttcacaacca tacgtgaatg ttactcggaa ggatacttag      720
aattgtcatt ggataggaaa tggtcgcaca ccatttcaca attaaaggaa gccacgttta      780
gactgtataa caccaaagta atacatgcag cttgtgcgat ggtttcacta ctccacgcat      840
caaacataat gccagaattc ctttgccaaa taatagctgt atacaaaata attcctgcaa      900
atgcagcaaa attactatcg tcgccaatga cgttgtacat aggcatagca actttttccat      960 ctaagatggt agcatcaact ggtaacgcct cagaatgtgc ttcaatggac ttgccaaata     1020
atgtctttgt cgccaaagaa cagattgaag aatggaatgt ggcattcaaa gatgatcctt     1080
taaatgagtc gctgttactt atagaaatga ataagaatct gaagactgat gtcgacacgt     1140
tcgtaaaaat atttaactgt tttttcggcga cttttcatgt tggacataga atcgataatg     1200
cacaggacgc gatagttgat caggtaacgg ttcagtacac cacagacgta gatcgtgaaa     1260
tgtatgatat gtattattac aaactgaaaa gtatgttgaa gactgaaatt aaaaagtatg     1320
ttgaggatca tatacatcgt gactaccaag acgttaccgc tgagtcgtta tctgctctcg     1380
ccaactcgtc aaacggattt cagaaagagg tattctttat cgacagaaaa ataaaaacaa     1440
tcaagaaaat attgcatctc gatgcagatt tgttggaagg agatttcaga gatgtgcgta     1500
aagtcatgtc tagaggtata cccatgggaa cgcgtaatgt tccagcccgt cagactagag     1560
gcatattcat cttaccatgg caagtagcag cagttcaaca cacaatagcg gaatctttat     1620
acaaaacagc aaaaaaagga gcgtaccaag ggtcattcgc tgaagcttac acttcaaaga     1680
ccgcatcatt aacatatgga gtattggctg aagatacttc taaggctatg aaaataattc     1740
tttatacgga cgtgtcacaa tgggacgcca gccaacataa cacacaacca tacagatcag     1800
catggataaa tgcaattaaa gaggtgagag aagaaggagg atggtcgaaa gaccaggagc     1860
caaccatgtt aggcataaac gtgcttgacg caatgagcgt gatacaagag gcattgctaa     1920
attcaacgtt aatcgttacc tccaccaaat ctaacagaaa catactaaca atcagatatc     1980
acggggtcgc gtcaggagaa aaaacaacga aggttggtaa ctcattcgcg aacgtggcgt     2040
tgattgaaac tgtactagat gtcacaaaac aaaagatacc agacatcgaa gtgactcatc     2100
tgagagtgga tggggacgat aacgtcgtgt cgatcaacac agcatgcaat atatcaaaac     2160
tacaaactgt aatcaaatcc aactatcaaa agttaaatgc acgagttaag gcgcttgctt     2220
cttacacagt tcttgaaatg gcgaaacgat ttattatatg tggaaacatc tttgaaagag     2280
gtgctatacc aattttttact gctgaaaggc catatggcac ggacgtctca atacaatcta     2340
tgactggttc atcaatctac tcatctgccg tgaacgcata tagagcgttt ggtgataagt     2400
acttaagctt tatgatggac gtgttggtac ctccatcatc aacagtgaga ctgactggca     2460
gattacgagt gttgctatcg ccaattacac tgtttgcgac tggacctttta agctttgaag     2520 tgactcaaaa tggattagga ggaagatgta gactgtatac accaaatagc cgactgatgc     2580
aattatttaa gatgctgaca gacactgtgt ctgtagcggt aacaccagaa gaagtaaaat     2640
```

-continued

```
tatatgcaaa gacaaatcaa ttcaaggaaa gagtgtctgt tatggcaaat agtctcaacg      2700
caaaaattaa aacaaatgct ccagccctag ttgcgatatt acgggagaaa gaagaacaga      2760
aaacgttggg agtgccaaac gtgcagacgc agaagaacag gaagcaggta aatgaggcat      2820
tgaagatact atctgttcca gaaagaaatg atctaattcc aaaaggctac tacccagaag      2880
agctgtacac cttagtgtta tctaactcaa aaatcacata taaggatttt ttaccagtgc      2940
acagtattta ccacacgaat aaccatgccg tcgcgttact tcataatcaa ttaggggtaa      3000
cgataagcga gtcaaaacca ataactaaac cagttaacca cttgtacgac attgtaagca      3060
cactatcacc aatttctata tcaccaagtg atattttaaa gcaatcaaag agatatgact      3120
tgacatcata caatggaaag aaaaggttct taagtgactt gggattaacg gggaacacct      3180
taaaaacata tctcgcatcg aagatgttat tcagagatct tttattggct aaatatgatg      3240
aattatacag tacaccaggt tttggtgcaa cgcaactgac aacaataccg ttgaatatac      3300
attcagctga gcaggttttc agtataaatg tcaagctgcc acctcatctg tatgaaataa      3360
tgatgttaat gttgctttat gagtacgtcc actatgtgtt catgacaaaa aggacttaca      3420
ccgctgtact atcaccgata tctgcagagc tccggcagat atcagcggtg taagtccttt      3480
t                                                                      3481
```

```
<210> SEQ ID NO 2
<211> LENGTH: 3390
<212> TYPE: DNA
<213> ORGANISM: Equine rotavirus

<400> SEQUENCE: 2
```

```
gcagatatct gggttttat atgtatggtt taccaggcgt catcagagaa tgacaccaca        60
tcaagtttaa tattatcaag cattttcaat attaaactag atagtttaac cgattgatcc       120
tgcgacatcg gtgatagtac agcggtgtaa gttctttttg tcatgaacac atagtggaca       180
tactcataaa gcaacattaa catcattatt tcatacagat gaggtggcag cttgacattt       240
atactgaaaa cctgctcagc tgaatgtata ttcaacggta ttgttgtcag ttgcgttgca       300
ccaaaacctg gtgtactgta taattcatca tatttagcca ataaaagatc tctgaataac       360
atcttcgagg cgagatatgt ttttaaggtg ttccccgtta atcccaagtc acttaagaat       420
cttttctttc cattgtatga tgtcaggtca tatctctttg attgcttcaa aatatcactt       480
ggtgatatag aaattggtga tagtgtgact acaatgtcgt ataagtggtt aactggttta       540
gttattggtt ttgactcgct tatcgttact cctaattgat tatgaagtaa cgcgacggca       600
tggttattcg tgtggtaaat actgtgcact ggtaaaaaat ccttatatgt gattttcgag       660
ttggataaca ctaaggtgta caactcttct gggtaatagc cttttggaat tagatcattt       720
ctttctggaa cagatagtat cttcaatgcc tcattcacct gcttcctgtt cttctgcgtc       780
tgcacgtttg gcactcccaa tgtttttctgt tcttctttct ctcgtaatat cgcaattagg       840
gctggagcat ttgtttttaat ttttgcgttg agactatttg ccataacaga cactctttcc       900
ttgaattgat ttgtctttgc atataatttt acttcttctg gtgttaccgc cacggataca       960
gtgtctgtca gcatcttaaa taattgcatc agtcggctat ttggtgtata cagtctacat      1020
cttcctccta atccattttg agtcacttca aagcttaaag gtccagtcgc aaacaacgta      1080
attggcgata gcaacactcg taatctgcca gtcagtctca ctgttgatga tggaggtacc      1140
aacacgtcca tcataaagct taagtactta tcaccaaacg ctctatatgc gttcacggca      1200
gatgagtaga ttgatgaacc agtcatagat tgtattgaga cgtccgtgcc atatggtctt      1260
```

-continued

```
tcagcagtaa aaattggtat agcacctctc tcaaagatgt ttccacatat aataaatcgt        1320
ttcgccattt caagacctgt gtaagacgca agcgccttaa ctcgtgcatt taacttttga        1380
tagttggatt taatcacagt ttgtagtttt gatatattgc atgctgtgtt gatcgacacg        1440
acgttgtcat ccccatccac tctcagatga gtcacttcga tgtctggtat ctgttgtttt        1500
gtgacatcta gtacagtttc aatcaatgcc acgttcgcga atgagttacc aaccttcgtt        1560
gttttttctc ctgacgcgac cccgtgatat ctgattgtta gtatgtttct gttagatttg        1620
gtggaggtaa cgattaacgt tgaatttagc aatgcctctt gtatcacgct cattgcgtca        1680
agcacgttta tgcctaacat agtaggctcc tggtctttcg accatcctcc ttcttctctc        1740
acctctttaa ttgcatttat ccatgctgat ctgtatggtt gtgtgttatg ttggctggcg        1800
tcccattgtg acacgtctgt ataaagaatt atcttcatag ccttagaagt atcttcagcc        1860
aatactccat atgttaatga cgcggtcttt gaagtataag cttcagcgaa tgacccttgg        1920
tacgctcctt tcttggctgt tttgtataaa gattccgcta ttgtgtgttg aactgctgct        1980
acttgccatg gcaagatgaa tatgcctcta gtctgacggg ctggaacatt acgcgttccc        2040
attggtatac ctctagacat gactttacgc acatctctga aatctccttc taacaaatct        2100
gcatcgagat gcaatatttt cttggttgtt tttattttc tgtcgataaa gagtacctct        2160
ttctgaaatc cgtttgacga gttggcgaga gcagataacg actcagcggt aacgtcttgg        2220
tagtcacgat gtatatgatc ctcaacatat tttttaattt cagccttcaa catacttttc        2280
agtttgtaat aatacatatc atacatttca cgatctacgt ctgtggtgta ctgaaccgtt        2340
acctgatcaa ctatcgcgtc ctgtgcattg tcgattctat gtccaacatg aaaagtcgcc        2400
gaaaaacaat taaatatttt tacgaacgtg tcgacatcag tcttcaggtt cttattcatt        2460
tctataagta acagcgactc atttaaagga tcatctttga atgccacatt ccattcttca        2520
atctgttctt tggcgacaaa gacattattt ggcaagtcca ttgaagcaca ttctgaggcg        2580
ttaccagttg atgctaccat cttagatgga aaagttgcta tgcctatgta caacgtcatt        2640
ggcgacgata gtaattttgc tgcatttgca ggaattattt tgtatacagc tattatttgg        2700
caaaggaatt ctggcattat gtttgatgcg tggagtagtg aaaccatcgc acaagctgca        2760
tgtattactt tggtgttata cagtctaaac gtggcttcct ttaattgtga aatggtatgt        2820
gaccatttcc tatccaatga caattctaag tatccttccg agtaacattc gcgtatggtt        2880
gtaaacaggt agttcaaagc tttcttttcc tcgtcactat atgttgaaat tcttttgaga        2940
actgataata caactgaacc aattagtgta tgcgttctgt gataataatt cggcattaaa        3000
ccttgcaatg tatccgattg ccatttgtaa tcaccagtat ctatgtattc aatttcatta        3060
tctcgaatgt attcacagat tggtatgttg taatggtatg gtttcagcac ggacgcattt        3120
ttcgtcctcc actgtttagc ttgaaattct atagccttga ttgaatggaa tacgtcatct        3180
gtagatgtta gattcactac attatcgatc agtttcaaca ctatttctct tttgtcagat        3240
ttatcgtcta catacacggt taaatacctt aaccttagta atttttccag tttactatcg        3300
atatcttcag ttgattcctt caatttttct atttcatcta acacttcatc gggtgtctgt        3360
gattttatac acatatgacg ctgccgacga                                        3390
```

<210> SEQ ID NO 3
<211> LENGTH: 2175
<212> TYPE: DNA
<213> ORGANISM: Equine rotavirus -continued

```
<400> SEQUENCE: 3
taagaacaac attatcaaag accctattca tagatgtaga cgccgaagag tactcggttt      60
atgttcctct agaagtgcaa aacatttcac ctgtggtgat tgacattaga ccaatacaga     120
catataaacc aaaaacttta atgtacaaag atacggcgat aataccttca aacaatgact     180
tggtgtcaga tcaatgggga gcggacgaaa tcctatatga ttcacacatg tttaacgaca     240
ttaacatagg ccagattgaa gattttgaaa catatttgtt agagaaagct gtagagatta     300
aagactcgct gccaaatatc aaccatatat cacaattaag taaagacacg aatcctttca     360
atgtacacaa cacactatgt ttagattttg gacaaaagga gtattataat ctaatttcag     420
acagaacgaa ccagtcattt gtggggagaa gacaagcggt acaatttgat aacgttgttg     480
tggacgggat tgaacgtaca gcgcgcatat cgttgagact tcatccattc gataaccaaa     540
tgctaaactt aataccactg aatttaatac atgagcagcc cattattgat gtaattagag     600
agtaccagct agtagcggcg gatggtttcg ttgctacccc aaaaataagg cttgacaagg     660
atgtgactat aatcgcagat gcacggtctc cagtgcttgc aagattatgt gaattatcgc     720
cttatttgca tcgaacaaga atcttagatt caatgactca gttcagccca ttgtggaagg     780
ttaacgtttt ttcaagttcg atagagaatg ctaaagactc catttataag atggctgaga     840
tttcattcac tgtagccgac tctgttacct cagcgctgtc aacggtcaat gtagcctcag     900
cgcaacaaac cctaactgtt ttacttaatt catgtatatt ccgtcttgag gttgatccga     960
ctggaagtca gtcgaacttt ggtgctgcaa tatcggcagc gataatgctt gttttgttcc    1020
caactgatga agaaacgatg cctacgaatg ttttttgataa tctatgcaac ttagtgtata    1080
acgaattgat agcttggacg gtcgacagac caacgttcgt caaacgcacg ggacaaacta    1140
acgcatttga agctaatgtt aatatcggtg ggggtaatat gaatagagac atattggctt    1200
acatcaggtt tatactactc agaaggccat ggattttgta tcaacggaca tacgacgagg    1260
catatgcggc tgatatattc attccaaaca ttgacgaagc caacataaat gaccaagctt    1320
atgtagctgt aaatagttta ttctcaggcc tgatccaggc agcacagagg aatccgaacc    1380
cagggaggca aatcagtgcg aattctttta gaaaattgct aaaatcaatg aaagatgtgt    1440
gttcaaacaa attgatgcca atagttagat taatcaggta taatattgaa aggatggcga    1500
gagtttatag gtggtttcca tattcagccg acttcgcaaa tcgtataccg cacttccgcg    1560
atgaaaggct aagggttaag gttccaatat caggtgtgct ctccatcatg ctagggataa    1620
ataaagcgcc agaggccttc gactggtata acattctgaa gtttgctgat tcaattagat    1680
tgaaaaatta tgcagaaatg gaatcaatag aaatcataat gtctaaagct ataattcgca    1740
atgacattaa accatcaagg tcaaagaagg attacataat tcaaaattta aaaccaccaa    1800
caaatgttgt tgcagctata gccaaaatgc cctcagctac attaacatca atattgtctg    1860
atcggattct tgtcaatggg gtccggttaa ctcagtcctt cggagtaatc aatagggtga    1920
ttgatgccat tagagttgca tttgagaacg taccgacagc agaacatggt atagctaagg    1980
gtgctttgtt attgccatac ccacgaccat tcaacagatc atctgcttac gtgcgtaaag    2040
ataatgttat atataacgct ccaacagagg tacagagatt taatatatct gatttattgg    2100
agggaagatt ttatcaagga ctaataggtc aagatatctg ccggagctct gcagatatcg    2160
tgggtatggc aataa                                                     2175

<210> SEQ ID NO 4
<211> LENGTH: 2777
```

-continued

```
<212> TYPE: DNA
<213> ORGANISM: Equine rotavirus

<400> SEQUENCE: 4
taatcctcaa acacaagcaa tccattgaag agcgtcacat caggaggttt aactgaagta      60
aattccaact tatccactac ggatgtgttg atttgtatgt ccctatactg gaatgcgtaa     120
acggtcgaat cttgctgtac ggcgattttt ggcgcatcaa tgatgaagac tgatgttttt     180
gacagcagct gttcaaattg tgtgttcggc ctctgaatgt ttgaatcgct ataatggtct     240
actgtaggtg gtgaaactat tttattatgc cttagatctt ctggccgaac acatgcatcg     300
tatggagatg acatcgtcaa gtatcctgaa gttaccgatt caatcgccgt cacgtcaaga     360
ttacgcactt gtaatggacc atttatgaca aatggagaca tgcgttgtac ttggcctatt     420
agtccttgat aaaatcttcc ctccaataaa tcagatatat taaacctctg tacctctgtc     480
ggagcgttat atataacatt atctttacgc acgtaagcag atgatctgtt gaatgatcgt     540
ggatatggta ataacaaagc acccttagct ataccatgtt ctgctgtcgg tacgttctca     600
aatgcaactc taatagcatc aatcacccta ttgattactc cgaaggactg agttaaccga     660
accccattga caagaatccg atcagacaat attgatgtta atgtcgctga gggcattttg     720
gctatagctg caacaacatt tgttggtggt cttaaatttt gaattatgta atccttcttt     780
gaccttgacg gtttaatgtc attgcgaatt atagctttgg acattatgat ttctattgat     840
tccatttctg cataattttt caatctaatt gaatcagcaa atttcagaat gttataccag     900
tcgaaagcct ctggcgcttt atttattcct agcatgatgg agagcacacc tgatattgga     960
actttaaccc ttagccttc atcgcggaag tgcggtatac gatttgcgaa gtcggctgaa    1020
tatggaaacc acttataaac tcttgccatc ctttcaatat tatacctgat taatctaact    1080
attggcatca atttgtttga acacacatct ttcattgatt ttagcaattt tctaaaagaa    1140
ttcgcactga tttgcctccc tgggttcgga ttcctctgtg ctgcctggat caggcctgag    1200
aataaactat ttacagctac ataagcttgg tcatttatgt tggcttcgtc aatgtttgga    1260
atgaaaatat cagccgcata tgcctcgtcg tatgtccgtt gatacaaaat ccatggtctt    1320
ctgagtagta taaacctgat gtaagctaat atgtctctat tcatattacc cccaccgata    1380
ttaacattag cttcaaatgc gttggtttgt cccgtgcgtt tgacgaacgt tggcctgtcg    1440
accgtccaag ctatcaattc gttatacact aagttgcata gattatcaaa aacattcgta    1500
ggcatcgttt cttcatcagt tgggaacaaa acaagcatta tcgctgccga tattgcagca    1560
ccaaagttcg actgacttcc agtcggatca atctcaagac ggaatataca tgaattaagt    1620
aaaacagtca gggtttgttg cgctgaggct acattaaccg tcgacagcgc tgaggtaacg    1680
gagtcggcca cagtgaatga aatctcagcc atcttataaa tggagtcttt agcattctct    1740
atcgaacttg aaaaaacgtt aatcttccac aatgggctga actgagtcat tgaatctaag    1800
atccttgttc gatgcaagta aggcgataat tcacataatc ttgcaagcac tggagaacgt    1860
gcatctgcga ttatagtcac atccttgtcg agccttactt ttggggtagc aacgaaacca    1920
tccgccgcta ctagctggta atctctaatt acatcaataa tgggctgctc atgtattaaa    1980
ttcaggggta ttaaattcag catttggtta tcgaatggat gaagtctcaa cgatatgcgc    2040
gctgtacgtt caatcccatc cacaacaacg ttatcaaatt gtaccgcttg tcttctcccc    2100
acaaatgact ggttcgttct gtctgaaatt agattataat actcctttg tccaaaatct    2160 agacatagtg tgttgtgcac attgaaagga ttcgtgtctt tgcttaattg tgatatatgg    2220
```

```
ttgatatttg gcagcgaatc tttaatttct acagctttct ctaacaaata cgtttcaaaa      2280
tcttcaatct ggcctatgtt aatgtcgtta aacatgtgcg aatcatatag gatttcgtcc      2340
gctccccatt gatctgacac caagtcattg tttgaaggta ttatcgccgt atctttgtac      2400
attaaagttt ttggtttata tgtttgtatt ggtctaatgt caatcaccac aggtgaaatg      2460
ttttgcactt ctagaggaac gtaaaccgaa tactcttcgg cgtccacatc tatgaataga      2520
gtctttgata atgtcgttct tagttggaaa acgttttgtg tgaatataga cgttggatcc      2580
ggttggtcat tgatcgtgtt aaccacatct tcttgtacct ctacgttgaa tactagacca      2640
tttatattgg atagttccaa tagtttggat tggacgtccg gttgtaggac gcccttactc      2700
agtcttttca agtcattgac caactgatca aaaatctttt gtttgtcgtt tttatcattc      2760
gtagcttgta ttgcttg                                                      2777
```

<210> SEQ ID NO 5
<211> LENGTH: 1383
<212> TYPE: DNA
<213> ORGANISM: Equine rotavirus

<400> SEQUENCE: 5

```
aattcttcta cacaacatga ttacaaaaag caattgtcat cttttttatcg tgagaaagtg        60 gactgggatt acgtgcatag acacagattg aaatttgaaa atgcgttttg ccatttattc       120
ttgcatcata taatcaagag taggtcttat tcaataatct atgttaacac gctctataac       180
attggaaatt ggacagaagc gtatccatgg cttaacatac gcgtggtgga ccatattcct       240
gtcattctaa acaactcagt agtttttggt tttatgttat caacgaacgt gtgttcattc       300
tcagtgaatg ttgatagtga taaagttgtt tattcaccga aaccatacga tgatgaaaac       360
aatgtttgga ccgtttcaat actaggggag aatataggtg tgccttcaaa tgaagcagaa       420
aggatagcag caaagaaaaa tggactgcca aactacattt acggtggggt gaagtttgat       480
gtcgaagcgc ttgattttaa ttatattaca gttggtctgt attcactatc caatgtcata       540
aactccccag agctaatcaa agctacttta tcttatgatc acattttac ctttccaaca        600 tattcagagg gtgattggag actcgagatt gagaaaacaa acaaaatttt cattacaacg       660
cagaagcaat tcaaattcaa tgattggata attgatgcga aaaatctttc tctggaaatg       720
gacactgagg ttgtctcaga atctgttttc ctgcagcttg gtaaagatcg cgctttcatc       780
tcagatcgtt atcaacacat ggtcgcattt cgatttaaac aaaaaaacta ttactcagac       840
aaatatatgt cacatctggg aataagacaa ccatcaattt tcaacaggga cagatttctg       900
acgtcacgtc tatctgcgta catcgacaga caattgacac tcaattcgga tttgtcttca       960
atagagaaaa accactttc agggttttca ggacacttga ttgcagtcga aaaatatttt      1020
catgcactgg cttacacaat gtctccaatg cggtgggcta acagagcgtt gtctgacgca      1080
atttacaaaa aaactgacag gtggaccaat gctgttggtg agcgccattc gattcaagac      1140
tttagaaata cgtatgcata tttgggagac agtatcaatc caatatttcg atccaatctg      1200
gtgactaaca aatatgcgga taagccaact tactgtatcc aattattaag taagaagaac      1260
cacatcacgc tacaactcac aactacatca ccggatagag ccatgcctct aataattaaa      1320
gcggttgagg gcactagatt caaatatttta gggagaaaca aatttggaac gatggatgtt      1380
gca                                                                     1383
```

<210> SEQ ID NO 6
<211> LENGTH: 2372

-continued

```
<212> TYPE: DNA
<213> ORGANISM: Equine rotavirus

<400> SEQUENCE: 6
gatatctgcg gtacaatatg tcgaagctca ttgagttttc tgacctgggc atcgaggtca        60
caaaccgtga gcagctgttc aaaatatcaa acaatacatc ctcatacgaa acaattagac       120
caagcaaaga tatagaagat tacatcagag aaagctctca ctacgtggta attgataaga       180
gaagaaatga accatttgtt gaagtattta ctcaattgtt tccttcttca attgtttata       240
accataagga aggttataag tctggtggct gtagacatct tcttaacaat gttttacatg       300
ttagtaacta tatgcacact tattgcaaca gtgatactag aaatctcgct cctgatggtt       360
ggaccattga caaggctgat ggatttgatg atccaattgg tgactacatt cttcgctcaa       420
tggtgaatga ttgttcaata gagaataaag cgcagcacag gaataaacca aacggagttt       480
acccgaaact cctaaacata aatgaatatt ttgttaaaac cctaaaaaaa atgataactc       540
ccgttagtaa tgttgatttt caatcatatc attacctgaa ccaaagaaga cagataggca       600
cattagttag aaatacaata ttcgaactaa tcgcaaataa taattggaat gtcaattata       660
ttggaccaga atttgagtca tttagaaata tttgcgagtt gctactgaat agaaattata       720
cagggaaaat aagatttttt accttcaatt cttctacaca acatgattac aaaaagcaat       780
tgtcatcttt tcatcgtgag aaagtggact gggattacgt gcacagacac agattgaaat       840
ttgaaaacgc gttttgccat ttattcttgc atcatataat taagagtagg tcttattcaa       900
taatctatgt taacacgctt tacaacattg gaaactggac agaagcgtat ccatggctta       960
acatacgcgt ggtagaccat attcctgtaa ttctaaacaa ctcagtagtt tttggtttta      1020
tgttatcgac gaaagtgtgt tcgttctcag tgaatgttga cagtgataaa gttgtttatt      1080
caccgaaacc atacgatgat gagaacaatg tttggaccgt ttcaatacta ggggaaaata      1140
taggtgtgcc ttcaaatgaa acagaaaaga tagcagcaaa gaaaaatgga ctgccaaact      1200
acatttacgg tgggatgaag tttgatgtcg aagcgcttga ttttaactat attacagttg      1260
gtctgtattc actatcaaat gtcataaact ccccagaact aattaaagct actttatctt      1320
atgatcacat ttttactttt ccaacatatt cggagggtga ttggagactc gagattgaga      1380
aaacgaacaa aattttcatc acaacgcaga agcaattcaa attcaatgat tggataattg      1440
atgcgaaaaa tctttctctg gaaatggata ctgaggttgt ctcagaatct gtgttcctgc      1500
agctcggtaa agatcgcgct ttcatctcag accgttatca acacatggtc gcatttcgat      1560
ttaaacaaaa aaactattac tcagacaaat atatgtcaca tctgggaata agacaaccat      1620 caatttttcaa cagggacaga tttctgacgt cacgtctatc tgcgtacatc gacagacaat      1680
tgacacttaa ttcagatttg tcttcaatag agaaaaacca cttttcaggg ttttcaggac      1740
acttgattgc agttgaaaaa tattttcatg cactggctta tacaatgtct ccaatgcggt      1800
gggctaacag agcgttatct gacgcaattt acaaaaaaac tgacaggtgg accaatgctg      1860
ttggtgaacg ccattcgatt caagacttca ggaatacgta tgcatatttg ggagacagta      1920
tcaatccaat atttcgatct aatctggtga ctaacaaata tgcggataag ccaacttact      1980
gtatccaatt attaagtaag aaaaaccaca tcacgctaca gctcacaact acatcaccag      2040
atagagctat gcctcaaata attaaagcgg ttgagggcac tagattcaaa tacttaggga      2100
ggaacagatt tggaacgttg gatgttgcac tgtatcaaac agatggtatg acacaatatg      2160
aaattgtgaa cattctgaga acaatggaca ttccctgtca acaaacgagg ccatacataa      2220
```

-continued

```
tgcatatgac gatcaaagat caaagtgaca taccatcgac gatcgttgct aattcgaata      2280
acgttaaagt caaagaaatt agatgctgag ctgacatatg atccacgaga ctatctgccg      2340
gagctctgca gatatcgtct cctatgtaac at                                   2372

<210> SEQ ID NO 7
<211> LENGTH: 1428
<212> TYPE: DNA
<213> ORGANISM: Equine rotavirus

<400> SEQUENCE: 7
ccgacgggca aagcgggaat taaccaatca tggagaccgg caacagacta caacggacag        60
tatgtctgca tgcaaccagg cgatatgttt tcggtttggt attttgaaga taggtggcag       120
ataaatcagg caatatacgc taaaaatttc cagtcagatt caagagctga aggcgagtta       180
gaaaatacgg gaagtttgat atttagaatg aattatatac caagtctagc tggaatcagg       240
aataaagcgg gtaaagttaa atacaggtat ataaatgggg gctttgcgca ggttgacgca       300
ggatcttaca ctggcatggc aataatatta aattttgagt gctacggtcg aaaattttat       360
gctgattcaa acaactatcc ggttgacaac actttgaatc catatatatg ttacatagga       420
gatgactata cagtaggagg gacgcactac agaaacggtg catgctcagg ctacgctgct       480
ggctatgatg acacaatatt ggaacatgat atgactatat catatacggt aatgaaacca       540
tcagatccag attttgtcac aggggggagaa agctacggac agagtataac gtcgggacta       600
gaagtgtcag tccgcaatct acaagatcag ataaactcaa tattagcgga actgaatata       660
cagcaagtta cgtctgcggt gttttcagcg gttacgtcag ttggagacct accaaatcta       720
ttttcgaatg ttaccaagat tttcagtaag acgaaggacg ctttagcgaa attgaaagga       780
agaaaggtgg ctaaaacgga acctgttaaa gctacaatga ttatagataa gtctaacatc       840
gatgtgccaa atgtatctat agttaacaaa atgccagaag aatacgaact gggggtcatc       900
tataattcaa tgcgccaagc gagactgcaa agggagggta agcacgattt tccgacattc       960
gcactagcaa ccgagatgaa gttgccgtac atacaaaata ccaacacatt aacgcctaaa      1020
ttcaaaaaat acttgagtga tagaggtttg ctgtgtgatg acaccgcagc cgttcaattt      1080
gatcctatgg atctaacgtt ttcaacacta cgaaagagaa acgcggacat tctgaagtat      1140
aagattgatc cggagatagc acatgaagtg ctttcagaga tgtcgacaac agccacaaga      1200
tcactgtttt cactgaatgt gaggaaacag ataagtacga ataacgaatt tggatctccg      1260
acatatgaac agataatcaa cagaatcctc gatgatagag aaattcttga tatcatgggg      1320
aaattaaaca ggcaaaccgt agggaactta ttccaagaat ttttagatag aacgaaagac      1380
atgctgtcca actacgtcta aaggaatgag cggcggacgg gtgagtaa                   1428

<210> SEQ ID NO 8
<211> LENGTH: 2275
<212> TYPE: DNA
<213> ORGANISM: Equine rotavirus

<400> SEQUENCE: 8
gactctgcag atatcgttcg aagatgagga cgcagtggca gcaagaaacg gttcagatac        60
aacttcgaaa gagatgtacc gaccaaagcg gacgggaggt actgctataa agcagaggtg       120
aataaatcaa attatactac cgaagtgcgc gggtttgcac tgggggaagc ggatgaacgt       180
gtaagtgcgg agcaattcca ggtttatagc ggagaggtga ctaatggtta cacattcata       240
aacggagatc caccatgtca aacggtaata cgtatttact tgaatgtaac aggtgaaatt       300
```

-continued

```
acgatagacg ggcagagtgt tcaaggaata tatttcgagg ctacttcctg catcagaacg        360
gataatggtt ataacctgca tgcgtataga gatcgtagtg tggtaccaac tgaggcacaa        420
tggaaattaa taacgcgtgc tttctcaaaa aacggatgca ccggtttaga cggaaatggt        480
cagttgtcag cctcagtttc aattaaaaat gaaaaggaat ggtcgtatga tattagcgga        540
gagactgagt taaacatgta ctcttggtca gatttatgtc aacagtcacg aacaactatg        600
agtaatgcaa aacagagttc tcgaataatc atatacgagc aggaagatgg attttggaaa        660
atattgactg aaacactatg gatcaaattg aaaccatatt ttaaaccata cggcacaatg        720
ggaggggctt ttaagaattg gctcgtagac tcaggatttg agaaatacga atacagttat        780
acgtacacga gggatggaaa agtggtcaac gcaacaacag tgacataccc aaaaccgacg        840
ggcaaagcgg gaattaacca atcgtggaga ccggcgacag actacaacgg acagtacgtc        900
tgcatgcaac caggtgatat attttcggtt tggtattttg aagataggtg gcagataaat        960
caggcaatat acgctaaaaa tttccagtca gattcaagag ctgaaggcga gttagaaaac       1020
acgggaggtt tgatatttag aatgaattat ataccaagtc tagctggaat caggaataaa       1080
gcgggcaaag ttaaatacag gtatataaat ggggggtttg cacaggttga cgccggatct       1140
tacactggca tggcaataat attaaatttt gagtgttacg gtcgaaagtt ctatgctgat       1200
tcaaacaact atccggttga caacactttg aatccatata tatgttacat aggagacgac       1260
tatacggtag gagggacgca ctacagaaac ggtgcatgct caggctacgc tgctggctat       1320
gatgacacaa tattggaaca tgatatgact atatcatata cggtaatgaa accatcagat       1380
ccagattttg ttacaggggg agaaagctac ggacagagta taacgtcggg actagaagtg       1440
tcaatccgca acctacaaga tcagataaac tcgatattag cggaactgaa tatacagcaa       1500
gttacgtctg cggtattttc agcggttacg tcagttggag acctaccaaa tctattttcg       1560
aatgttacca agattttcag taagacgaag gatgctttag cgaaattgaa aggaagaaag       1620
gtggctaaaa cagaacctgt taaagctaca atgatcatag acaaatctaa catcgatgta       1680
ccaaatgtgt ctatagttaa caaaatgcca gaagaatacg aactgggggt catctataat       1740
tcaatgcgcc aagcgagact gcaaagggag ggtaagcacg attttccgac attcgcacta       1800
gcaactgaga tgaaactgcc gtacatacaa aataccaata cactaactcc taaattcaaa       1860
aaatatttga gtgatagagg tttactgtgt gatgacaccg cagctattca atttgatcct       1920
atggatctaa cgttttcaac attacgaaag agaaacgcgg acgttctgaa gtataagatt       1980
gatccggaga tagcacatga agtgctctca gagatgtcga caacagccac aagatcactg       2040
ttttcactga atgtgaggaa acagataagt acgaataatg aatttggatc tccgacatat       2100
gaacagataa tcaacagaat cctcgatgat agagaaattc ttgacattat ggggaaattg       2160
aacaggcaaa ccgtagggaa cttattccaa gaatttttag atagaacgaa agacatgctg       2220
tccaactatg tctaaaggaa tgagccagtg ggtgagtaaa aaccccgat atctg            2275
```

<210> SEQ ID NO 9
<211> LENGTH: 1163
<212> TYPE: DNA
<213> ORGANISM: Equine rotavirus
<400> SEQUENCE: 9

```
ttacgcccaa taaatccgga taacgcttgc accctacgta ttaccgcggc tgctggcacg         60
tagttagccg gtgctctgca gatatcccct tacacgatac acgcaccgat aatttcgctg        120
```

-continued

```
gccgttagaa tatctactga tgattatgat gacatgagaa atggagttga gtctatacta      180
gattgtttgg ctgcggcgat tcgcactgaa ggctcgagac cggttagagt gattgaacgt      240
agagttattg aaccagtggt aaagcagctg gtcgaagatc tgaagttaaa aagtctgatt      300
tctgaaatct caattgccaa tttcgctgct actgataccg cgcttatcca accagaagta      360
gtagaaactg aaaatccatt gatagttggt atcatagaac aggtggttgt aagacaacca      420
gccagtctaa atggtggcaa tattagagca gcgattggca gatggtcagg taataaaggc      480
tcagtcacat gtgtctcagg catggaagca gaacatatgt tcttcgtgga actaaaagct      540
aggacgtgtg gtgtactgaa cgtcgtttat ctgccagccc caggagttat aatggtgcct      600
atgccgcaag gacgcaacag agaaagtgtt atacttgacg tatccgcaga gatgacagca      660
gatgatttta taatcgattt cttttgatgat aacaacattg tccatacgga aagaggagtt      720
ggcctatttt catttccaat gtgtaccaga attagattta gagttacacc atggacacaa      780
caaaaatctc agaatggact tgacactcca tcattggcta cgtgggcgaa cggtacgtct      840
ccgaggcagc cagcggtgtc tttcatgttt gaattaagaa gaaccttcac tgaaaacgat      900
tataaattcg tttcacgatg tacctcgaaa gttcaataca tattggatac caacttccca      960
gagacatcat ttattaacag gcctcaaata gaatggaacg tacaagagat gattacttct     1020
gacacagaca cagtatggtc acgtaaaatc gcaatgctag tcgcagcatt tgctgctaag     1080
atctgattct ccctgagccc gggagccggg ttgctctaga ggatgaaaaa aatagcacta     1140 aaaaccccg gatatctgca gag                                               1163
```

```
<210> SEQ ID NO 10
<211> LENGTH: 1163
<212> TYPE: DNA
<213> ORGANISM: Equine rotavirus

<400> SEQUENCE: 10
ttacgcccaa taaatccgga taacgcttgc accctacgta ttaccgcggc tgctggcacg       60
tagttagccg gtgctctgca gatatcccct tacacgatac acgcaccgat aatttcgctg      120
gccgttagaa tatctactga tgattatgat gacatgagaa atggagttga gtctatacta      180
gattgtttgg ctgcggcgat tcgcactgaa ggctcgagac cggttagagt gattgaacgt      240
agagttattg aaccagtggt aaagcagctg gtcgaagatc tgaagttaaa aagtctgatt      300
tctgaaatct caattgccaa tttcgctgct actgataccg cgcttatcca accagaagta      360
gtagaaactg aaaatccatt gatagttggt atcatagaac aggtggttgt aagacaacca      420
gccagtctaa atggtggcaa tattagagca gcgattggca gatggtcagg taataaaggc      480
tcagtcacat gtgtctcagg catggaagca gaacatatgt tcttcgtgga actaaaagct      540
aggacgtgtg gtgtactgaa cgtcgtttat ctgccagccc caggagttat aatggtgcct      600
atgccgcaag gacgcaacag agaaagtgtt atacttgacg tatccgcaga gatgacagca      660
gatgatttta taatcgattt cttttgatgat aacaacattg tccatacgga aagaggagtt      720
ggcctatttt catttccaat gtgtaccaga attagattta gagttacacc atggacacaa      780
caaaaatctc agaatggact tgacactcca tcattggcta cgtgggcgaa cggtacgtct      840
ccgaggcagc cagcggtgtc tttcatgttt gaattaagaa gaaccttcac tgaaaacgat      900
tataaattcg tttcacgatg tacctcgaaa gttcaataca tattggatac caacttccca      960
gagacatcat ttattaacag gcctcaaata gaatggaacg tacaagagat gattacttct     1020
gacacagaca cagtatggtc acgtaaaatc gcaatgctag tcgcagcatt tgctgctaag     1080
```

-continued

```
atctgattct ccctgagccc gggagccggg ttgctctaga ggatgaaaaa aatagcacta    1140 aaaaccccg gatatctgca gag                                            1163

<210> SEQ ID NO 11
<211> LENGTH: 1297
<212> TYPE: DNA
<213> ORGANISM: Equine rotavirus

<400> SEQUENCE: 11
actcgagcat acacttgcag ggcacttcaa ccgccaattt cacaacgcaa cacattattt      60
taacagtagg cgctgtcttg atagcactac ttttaacatc tctcattttc agctgtattt     120
gcaattgtta tctctactct aaactacgaa atggatttca aacagtttct cagcacgtca     180
ggaggaaaga aagatctcat accaacatac cagggcaaca aattcgacca gacatgtatg     240
tctaagaaac cgtggaaaac ggaaaaactc atgtacccgt cctccattcg tgaaacacca     300
tttgtggcag gtgaatccat attgattgaa gacgtatgtc cttttaatca tgaacacttt     360
tgtggcgcca ttcacattcc aacacagagc aatatgaaac caaaaggaag gacttcgcat     420
gtgacggctg ataaaattgc atggccatgt ggtatagaat caatcagtgt ggacggaaaa     480
gtgatctctg gatccgaatt tgtcaaatgc agatgtggca acctatatcc aacagttatt     540
aacgaagtta cagacttctt cattctgaca tgttgctcac atgacacgaa atcaatccaa     600
ctgtgtgtgt ctgaacgtta tgactgtgcc aattgtggaa agaaagtgcg ttggtatact     660
tcaggaaaag gcattctcac taaacacaaa ttttatctgc catctaagat ttgcccttca     720
tgttcacctt tcagagattt gatttccaca atgtccatgc ttaataaagt tgagttcatt     780
ggtccagact tcaggaagat gcaagacaac tatcaatgga aacatgcgct ggaaaatgga     840
tgtgaacaag cattcagggc cttgaattca ccacatattc tgagtaagat ttcaatcatc     900
tctaagatta atccatcact taatgttaac accgtgaccg aggtgataag ttcatttaac     960
agagaatggc catataacat tgtcatgaca ccaatctcta gaggcaaagt tgcaatcact    1020
aataattact ctaggacaat tataactttc aacagtaaca cggaattgtt cagatcagtt    1080
aacatgcttt tgttcaaatg gcggcttgct tgaacataga atgagagttc cagatctcta    1140
accggacgcg atatctgcag agctccggca gatatcgtca gccaatctca tatctctgaa    1200
cggacgtcgc gtctagtaac aactcacttg agtcatcttt gtttacgaaa tgtcaacctg    1260
taaattagct ttgtcagcca gtcctttgat cagtcgt                             1297

<210> SEQ ID NO 12
<211> LENGTH: 1301
<212> TYPE: DNA
<213> ORGANISM: Equine rotavirus

<400> SEQUENCE: 12
tgcagatatc attggtataa taatagtgta ccatctgtgc aagtctggga aacctatggg      60
aagcagccag tccagcttgc aatctcaggt acatagcacc aatatccatt ctcaacactc     120
gagcatacac ttgcaaggca cctcaaccgc taatttcaca acacaacaca ttattttaac     180
agtaggcgcc gtcttgatag cactacttct gacatctctc gttttcagct gtatctgcaa     240
ttgctacctc tactctaaac tacgaaatgg atttcaaaca gtttctcaac acgtcgggag     300
gaaagaaaga tctcatacca acataccagg acaacaaatt cgaccagaca tgtacgtcta     360
agaaaccgtg gaaaacggaa aaactcatgt acccgtcctc cattcgtgaa acaccatttg     420
```

-continued

```
tggcaggtga atccatattg attgaggacg tatgtccttt taatcatgaa catttttgtg      480
gcgccattca cattccaaca cagagcaata tgaaaccaaa agggaggact tcgcatgtga      540
cggctgataa aattgcatgg ccatgtggta tagaatcaat cagtgtggac ggaaaagtga      600
tctctggatc cgaatttgtc aaatgcagat gtggcaacct atatccaaca attattaacg      660
aagttacaga cttcttcatt ctgacatgtt gctcacatga cacaaaatca atccaactgt      720
gtgtgtctga acgttatgac tgtgccaatt gtggaaagaa ggtgcgttgg tatacttcag      780
gaaaaggcat tctcactaaa cacaaatttt acctgccgtc aaagatttgc ccttcatgtt      840
cacctttcag agatttgatt tccacaatgt ctatgcttaa taaagttgag ttcattggtc      900
cagacttcag gaagatgcaa gaaaactatc aatggaaaca tgcgttggaa aatgaatgtg      960
aacaggcatt cagggctttg aattcaccac atattctgag taagatttca atcatctcca     1020
agattaatcc atcacttaat gttaacacca tgaccgaggt ggtaagttca tttaacagag     1080
aatggccata taacattgtc atgacgccaa tctccagagg caaagttgca attactaata     1140
attactccag gacaattata actttcaata ataatgcgga attgttcaga tcagttaaca     1200 tgctttttgtt caaatggcgg cttgcttgaa catagaatga gagttccaga tctctaaccg     1260
gacgcagttg atcactataa taaaaaaccc cgatatctgc a                         1301
```

<210> SEQ ID NO 13
<211> LENGTH: 1027
<212> TYPE: DNA
<213> ORGANISM: Equine rotavirus

<400> SEQUENCE: 13

```
gggttcttat cggtacaaaa aaacgtaata agtgtgtcgt gagagggtca cccatccct       60 ggtcgccatg acgcagtcta tttcgatcgc agatttcatc gtgaaaactg aagatggttt      120
tatgccttca gatagagaaa atattgtgtt agatcgctac ttgtctaaag aactaaaaga      180
actaagagat aaatataaag atgagaagaa tgatagagca tcacttcgta ttaaaatgtt      240
tttgacgcca gcgccatcac gtcgcttcac tcaaagagga gtagtgccaa tgagagaact      300
caaaactacg tctgatctca caacttcaat gttcaacttg attactgact ggctactatc      360
tgtgctcgcc gatgaagaaa tggctgaatc ttttgaacaa ttcattgaga gcaaatttcc      420
agacattttt gcttcagctg acaaaattggc cagatttgct caaaggctag aagataagcg      480
cgacattatg catagaaatc catcaaaggc tttgaacgct ttcggagcat gttttttgggc      540 agtcaaaccg acatatgtca cggagggcaa gtgcaatgtt gtgagagcta ccgacgattc      600
tattatacta gaatttgagc caattccgga acatttgcga tgtggaagaa caagatcaac      660
tttctataaa ctgtacccac tgtcagaaga agctccggtg acaggtatga tcgcattacg      720
aggcgttgca ggtaatcaat ttctcatgta tcacgggcac ggacatatta gaacagttcc      780
ctatcatgaa atgagtgacg caatcaggtc ttttgcaaag aaaaagagtg atgagctgga      840
agcgatagcg aagtcatcac tcgcggtcca ctgtggtcag aaattcatga acatgcttga      900
tcagattaga tcaaaacaga aaatcgaaga tatcataaca caagccaaac agaatgatcg      960
aaagaaatag attgtgacaa atccaccatt gcgtttttaa ccgataagaa cccccgatat     1020
ctgcaga                                                              1027
```

<210> SEQ ID NO 14
<211> LENGTH: 1027
<212> TYPE: DNA
<213> ORGANISM: Equine rotavirus -continued

<400> SEQUENCE: 14

```
gggttcttat cggtacaaaa aaacgtaata agtgtgtcgt gagagggtca cccatcccct        60
ggtcgccatg acgcagtcta tttcgatcgc agatttcatc gtgaaaactg aagatggttt       120
tatgccttca gatagagaaa atattgtgtt agatcgctac ttgtctaaag aactaaaaga       180
actaagagat aaatataaag atgagaagaa tgatagagca tcacttcgta ttaaaatgtt       240
tttgacgcca gcgccatcac gtcgcttcac tcaaagagga gtagtgccaa tgagagaact       300
caaaactacg tctgatctca caacttcaat gttcaacttg attactgact ggctactatc       360
tgtgctcgcc gatgaagaaa tggctgaatc ttttgaacaa ttcattgaga gcaaatttcc       420
agacattttt gcttcagctg acaaattggc cagatttgct caaaggctag aagataagcg       480
cgacattatg catagaaatc catcaaaggc tttgaacgct ttcggagcat gtttttgggc       540
agtcaaaccg acatatgtca cggagggcaa gtgcaatgtt gtgagagcta ccgacgattc       600
tattatacta gaatttgagc caattccgga acatttgcga tgtggaagaa caagatcaac       660
tttctataaa ctgtacccac tgtcagaaga agctccggtg acaggtatga tcgcattacg       720
aggcgttgca ggtaatcaat ttctcatgta tcacgggcac ggacatatta gaacagttcc       780
ctatcatgaa atgagtgacg caatcaggtc tttttgcaaag aaaaagagtg atgagctgga       840
agcgatagcg aagtcatcac tcgcggtcca ctgtggtcag aaattcatga acatgcttga       900
tcagattaga tcaaaacaga aaatcgaaga tatcataaca caagccaaac agaatgatcg       960
aaagaaatag attgtgacaa atccaccatt gcgtttttaa ccgataagaa cccccgatat      1020
ctgcaga                                                                 1027
```

<210> SEQ ID NO 15
<211> LENGTH: 1084
<212> TYPE: DNA
<213> ORGANISM: Equine rotavirus

<400> SEQUENCE: 15

```
tctgatccac gattactagc gattccgact tcatggagtc gagttgcaga ctccaatccg        60
gactacgacg ttctttatga ggtttttatt aattggtggt cagccaatct catatctctg       120
aacggacgtc gcgtctaata acaactcact tgagtcattt tgtttacgaa atgtcaacct       180
gtaaattagc tttgtcagcc agtcctttga tcagtcgtat atgttcatct tgctcttctc       240
taagtacaac attctcactg gacaactttg cacaacgctc ttcaacatca gaaacatgtt       300
caattaagac ttggatatct ttcatatgat caagtgacat gttgtcaaac tgcttgttca       360
acgttgaaat ggtcaaattc aatgtcccgt tctctagacg gagttcagat atctctcttt       420
tgtagatctt tttctcttcc tcatggtgtt gattaaccaa ctcaagtctt tctctgtgat       480
tctcacgtag gaacgtaatc ttctttctca gcattataat ctgttggttc atttcactca       540
tgattctgtc cctttcctca attagctctt cttgatatct cattttttgtg tttgcttctt       600 cctgtattgt tttaatgctg ttttcgagtt ccgaattttt tttaatcaaa tcatcaacta       660
catcagaagg aaatgggttt aatttcatgt caacagtaga gtttagtaga accacttctg       720
cgtttcttgt tttcggtaga agtacagtat atccattctt cttgccaaca tcaaatgatt       780
gtagtagtct gtctttcatc gtttcaccat tcttccaaga ttcatgtctc aacctcaaca       840
cttcagtctc catatttttc aactgtatag ccattgttgt accggtcatt ggttttggaa       900
tcctcagttt gtagtatgca tcgcgccaat tgtccaacat cataccacaa tctttcattg       960
```

-continued

--- catgaatgaa atcttcaatg attttcaact gatcatcaat ttcatgttta gacaacacag    1020
atcctagaat tgacgcaaca gcgttcagag ccatagtgta agattctcac tgcgagcaga    1080
tatc                                                                 1084

<210> SEQ ID NO 16
<211> LENGTH: 1053
<212> TYPE: DNA
<213> ORGANISM: Equine rotavirus

<400> SEQUENCE: 16
gctctgcaga tatcagtggt ataatagtgt tcgtttcaga agctgctcgc agtgagaaac      60
ttacactatg gctctgaacg ctgttgcgtc aattctagga tctgtgttgt ctaaacatga     120
aattgatgat cagttgaaaa tcattgaaga tttcattcat gcaatgaagg attgtggtat     180
gatgctggac aattggcgcg atgcatacta caaactgagg attccaaaac aaatgactgg     240
tacaacaatg gctatacagt tgaaaaacat ggaaactgaa gtgctgaggt tgagacatga     300
atcttggaaa aatggtgaaa cgatgaaaga tagactgctg caatcatttg atgttggcaa     360
aaagaatgga tatactgtac ttctaccgaa aacaagaaac gcagaagtgg tcctactaaa     420
ctctactgtt gacatgaaat taaacccatt tccctctgat gtagttgatg atttgatcaa     480
gaaaaattcg gaactcgaaa acagcattaa aacaatacaa gaggaaacaa gcgcaaaaat     540
aagatatcaa gaggaactaa ttgaggaaag ggacagaatc atgagcgaaa tgaatcagca     600
gattacaatg ctgaaaaaga agattacatt cctacgtgag aatcacaaag aaagacttga     660
gttgattaat caacaccatg aggaagagaa aaaaatttac aaaagagaga tatctgaact     720
ccgtctagag aacgggacat tgaatttgac catctcaacg ttgaacaaac aatttgacaa     780
catgtcactt gatcatatga aagacatcca agtcttgatt gaacatgttt ctgatgttga     840
agagcgttgt gcaaaattgt ccaatgaaaa tgttgtactt agggaagaac aagacgaaca     900
tatacgactg atcaaaggac tggctgacaa agctaattta caggttgaca tttcgtaaac     960
aaagatgact caagtgagtt gttactagac gcgacgtccg ttcagagata tgagattggc    1020
tgaccaccaa ttaataaaaa ccccgatatc tgc                                 1053

<210> SEQ ID NO 17
<211> LENGTH: 20
<212> TYPE: DNA
<213> ORGANISM: Artificial
<220> FEATURE:
<223> OTHER INFORMATION: Forward primer for ER segment 1

<400> SEQUENCE: 17
cgtgaatgtt actcggaagg                                                  20

<210> SEQ ID NO 18
<211> LENGTH: 22
<212> TYPE: DNA
<213> ORGANISM: Artificial
<220> FEATURE:
<223> OTHER INFORMATION: Reverse primer for ER segment 1

<400> SEQUENCE: 18
caagctgcat gtattacttt gg                                               22

<210> SEQ ID NO 19
<211> LENGTH: 24
<212> TYPE: DNA
<213> ORGANISM: Artificial

-continued

<220> FEATURE:
<223> OTHER INFORMATION: Probe for ER segment 1

<400> SEQUENCE: 19
tggataggaa atggtcgcac acca                                          24

<210> SEQ ID NO 20
<211> LENGTH: 22
<212> TYPE: DNA
<213> ORGANISM: Artificial
<220> FEATURE:
<223> OTHER INFORMATION: Forward primer for ER segment 1

<400> SEQUENCE: 20
gttagatttg gtggaggtaa cg                                            22

<210> SEQ ID NO 21
<211> LENGTH: 20
<212> TYPE: DNA
<213> ORGANISM: Artificial
<220> FEATURE:
<223> OTHER INFORMATION: Reverse primer for ER segment 1

<400> SEQUENCE: 21
tgagagaaga aggaggatgg                                               20

<210> SEQ ID NO 22
<211> LENGTH: 22
<212> TYPE: DNA
<213> ORGANISM: Artificial
<220> FEATURE:
<223> OTHER INFORMATION: Probe for ER segment 1

<400> SEQUENCE: 22
acgctcattg cgtcaagcac gt                                            22

<210> SEQ ID NO 23
<211> LENGTH: 21
<212> TYPE: DNA
<213> ORGANISM: Artificial
<220> FEATURE:
<223> OTHER INFORMATION: Forward primer for ER segment 2

<400> SEQUENCE: 23
cgacagcaga acatggtata g                                             21

<210> SEQ ID NO 24
<211> LENGTH: 19
<212> TYPE: DNA
<213> ORGANISM: Artificial
<220> FEATURE:
<223> OTHER INFORMATION: Reverse primer for ER segment 2

<400> SEQUENCE: 24
tacctctgtt ggagcgtta                                                19

<210> SEQ ID NO 25
<211> LENGTH: 24
<212> TYPE: DNA
<213> ORGANISM: Artificial
<220> FEATURE:
<223> OTHER INFORMATION: Probe for ER segment 2

<400> SEQUENCE: 25
tgccataccc acgaccattc aaca                                          24

```
<210> SEQ ID NO 26
<211> LENGTH: 19
<212> TYPE: DNA
<213> ORGANISM: Artificial
<220> FEATURE:
<223> OTHER INFORMATION: Forward primer for ER segment 2

<400> SEQUENCE: 26
caaatgcgtt ggtttgtcc                                              19

<210> SEQ ID NO 27
<211> LENGTH: 20
<212> TYPE: DNA
<213> ORGANISM: Artificial
<220> FEATURE:
<223> OTHER INFORMATION: Reverse primer for ER segment 2

<400> SEQUENCE: 27
atgaagaaac gatgcctacg                                             20

<210> SEQ ID NO 28
<211> LENGTH: 22
<212> TYPE: DNA
<213> ORGANISM: Artificial
<220> FEATURE:
<223> OTHER INFORMATION: Probe for ER segment 2

<400> SEQUENCE: 28
tgcgtttgac gaacgttggc ct                                          22

<210> SEQ ID NO 29
<211> LENGTH: 19
<212> TYPE: DNA
<213> ORGANISM: Artificial
<220> FEATURE:
<223> OTHER INFORMATION: Forward primer for ER segment 3

<400> SEQUENCE: 29
tggcttacac aatgtctcc                                              19

<210> SEQ ID NO 30
<211> LENGTH: 22
<212> TYPE: DNA
<213> ORGANISM: Artificial
<220> FEATURE:
<223> OTHER INFORMATION: Reverse primer for ER segment 3

<400> SEQUENCE: 30
tgatactgtc tcccaaatat gc                                          22

<210> SEQ ID NO 31
<211> LENGTH: 22
<212> TYPE: DNA
<213> ORGANISM: Artificial
<220> FEATURE:
<223> OTHER INFORMATION: Probe for ER segment 3

<400> SEQUENCE: 31
tgcggtgggc taacagagcg tt                                          22

<210> SEQ ID NO 32
<211> LENGTH: 18
<212> TYPE: DNA
<213> ORGANISM: Artificial
<220> FEATURE:
<223> OTHER INFORMATION: Forward primer for ER segment 3
```

-continued

```
<400> SEQUENCE: 32
tcatcacaac gcagaagc                                                    18

<210> SEQ ID NO 33
<211> LENGTH: 21
<212> TYPE: DNA
<213> ORGANISM: Artificial
<220> FEATURE:
<223> OTHER INFORMATION: Reverse primer for ER segment 3

<400> SEQUENCE: 33
ataacggtct gagatgaaag c                                                21

<210> SEQ ID NO 34
<211> LENGTH: 21
<212> TYPE: DNA
<213> ORGANISM: Artificial
<220> FEATURE:
<223> OTHER INFORMATION: Probe for ER segment 3

<400> SEQUENCE: 34
tctgtgttcc tgcagctcgg t                                                21

<210> SEQ ID NO 35
<211> LENGTH: 22
<212> TYPE: DNA
<213> ORGANISM: Artificial
<220> FEATURE:
<223> OTHER INFORMATION: Forward primer for ER segment 4

<400> SEQUENCE: 35
atcaggaata aagcgggtaa ag                                               22

<210> SEQ ID NO 36
<211> LENGTH: 18
<212> TYPE: DNA
<213> ORGANISM: Artificial
<220> FEATURE:
<223> OTHER INFORMATION: Reverse primer for ER segment 4

<400> SEQUENCE: 36
tcgaccgtag cactcaaa                                                    18

<210> SEQ ID NO 37
<211> LENGTH: 24
<212> TYPE: DNA
<213> ORGANISM: Artificial
<220> FEATURE:
<223> OTHER INFORMATION: Probe for ER segment 4

<400> SEQUENCE: 37
acgcaggatc ttacactggc atgg                                             24

<210> SEQ ID NO 38
<211> LENGTH: 19
<212> TYPE: DNA
<213> ORGANISM: Artificial
<220> FEATURE:
<223> OTHER INFORMATION: Forward primer for ER segment 4

<400> SEQUENCE: 38
cgagcaggaa gatggattt                                                   19

<210> SEQ ID NO 39
```

-continued

```
<211> LENGTH: 20
<212> TYPE: DNA
<213> ORGANISM: Artificial
<220> FEATURE:
<223> OTHER INFORMATION: Reverse primer for ER segment 4

<400> SEQUENCE: 39
ctgagtctac gagccaattc                                                     20

<210> SEQ ID NO 40
<211> LENGTH: 24
<212> TYPE: DNA
<213> ORGANISM: Artificial
<220> FEATURE:
<223> OTHER INFORMATION: Probe for ER segment 4

<400> SEQUENCE: 40
aaaccatacg gcacaatggg aggg                                                24

<210> SEQ ID NO 41
<211> LENGTH: 20
<212> TYPE: DNA
<213> ORGANISM: Artificial
<220> FEATURE:
<223> OTHER INFORMATION: Forward primer for ER segment 6

<400> SEQUENCE: 41
acttgacact ccatcattgg                                                     20

<210> SEQ ID NO 42
<211> LENGTH: 19
<212> TYPE: DNA
<213> ORGANISM: Artificial
<220> FEATURE:
<223> OTHER INFORMATION: Reverse primer for ER segment 6

<400> SEQUENCE: 42
cgaggtacat cgtgaaacg                                                      19

<210> SEQ ID NO 43
<211> LENGTH: 22
<212> TYPE: DNA
<213> ORGANISM: Artificial
<220> FEATURE:
<223> OTHER INFORMATION: Probe for ER segment 6

<400> SEQUENCE: 43
aggcagccag cggtgtcttt ca                                                  22

<210> SEQ ID NO 44
<211> LENGTH: 20
<212> TYPE: DNA
<213> ORGANISM: Artificial
<220> FEATURE:
<223> OTHER INFORMATION: Forward primer for ER segment 6

<400> SEQUENCE: 44
acaggcctca aatagaatgg                                                     20

<210> SEQ ID NO 45
<211> LENGTH: 21
<212> TYPE: DNA
<213> ORGANISM: Artificial
<220> FEATURE:
<223> OTHER INFORMATION: Reverse primer for ER segment 6

<400> SEQUENCE: 45
```

-continued cagggagaat cagatcttag c                                          21

<210> SEQ ID NO 46
<211> LENGTH: 22
<212> TYPE: DNA
<213> ORGANISM: Artificial
<220> FEATURE:
<223> OTHER INFORMATION: Probe for ER segment 6

<400> SEQUENCE: 46
aatcgcaatg ctagtcgcag ca                                         22

<210> SEQ ID NO 47
<211> LENGTH: 24
<212> TYPE: DNA
<213> ORGANISM: Artificial
<220> FEATURE:
<223> OTHER INFORMATION: Forward primer for ER segment 5

<400> SEQUENCE: 47
agaaagatct cataccaaca tacc                                       24

<210> SEQ ID NO 48
<211> LENGTH: 18
<212> TYPE: DNA
<213> ORGANISM: Artificial
<220> FEATURE:
<223> OTHER INFORMATION: Reverse primer for ER segment 5

<400> SEQUENCE: 48
ttcacctgcc acaaatgg                                              18

<210> SEQ ID NO 49
<211> LENGTH: 22
<212> TYPE: DNA
<213> ORGANISM: Artificial
<220> FEATURE:
<223> OTHER INFORMATION: Probe for ER segment 5

<400> SEQUENCE: 49
tgtacccgtc ctccattcgt ga                                         22

<210> SEQ ID NO 50
<211> LENGTH: 19
<212> TYPE: DNA
<213> ORGANISM: Artificial
<220> FEATURE:
<223> OTHER INFORMATION: Forward primer for ER segment 5

<400> SEQUENCE: 50
aactgtgtgt gtctgaacg                                             19

<210> SEQ ID NO 51
<211> LENGTH: 21
<212> TYPE: DNA
<213> ORGANISM: Artificial
<220> FEATURE:
<223> OTHER INFORMATION: Reverse primer for ER segment 5

<400> SEQUENCE: 51
tctgaaaggt gaacatgaag g                                          21

<210> SEQ ID NO 52
<211> LENGTH: 22
<212> TYPE: DNA

-continued

<213> ORGANISM: Artificial
<220> FEATURE:
<223> OTHER INFORMATION: Probe for ER segment 5

<400> SEQUENCE: 52
tgtggaaaga aggtgcgttg gt                                                      22

<210> SEQ ID NO 53
<211> LENGTH: 19
<212> TYPE: DNA
<213> ORGANISM: Artificial
<220> FEATURE:
<223> OTHER INFORMATION: Forward primer for ER segment 8

<400> SEQUENCE: 53
gatgagctgg aagcgatag                                                         19

<210> SEQ ID NO 54
<211> LENGTH: 21
<212> TYPE: DNA
<213> ORGANISM: Artificial
<220> FEATURE:
<223> OTHER INFORMATION: Reverse primer for ER segment 8

<400> SEQUENCE: 54
ttctgtttgg cttgtgttat g                                                      21

<210> SEQ ID NO 55
<211> LENGTH: 24
<212> TYPE: DNA
<213> ORGANISM: Artificial
<220> FEATURE:
<223> OTHER INFORMATION: Probe for ER segment 8

<400> SEQUENCE: 55
cagtggaccg cgagtgatga cttc                                                   24

<210> SEQ ID NO 56
<211> LENGTH: 18
<212> TYPE: DNA
<213> ORGANISM: Artificial
<220> FEATURE:
<223> OTHER INFORMATION: Forward primer for ER segment 8

<400> SEQUENCE: 56
agagctaccg acgattct                                                          18

<210> SEQ ID NO 57
<211> LENGTH: 21
<212> TYPE: DNA
<213> ORGANISM: Artificial
<220> FEATURE:
<223> OTHER INFORMATION: Reverse primer for ER segment 8

<400> SEQUENCE: 57
ctgacagtgg gtacagttta t                                                      21

<210> SEQ ID NO 58
<211> LENGTH: 24
<212> TYPE: DNA
<213> ORGANISM: Artificial
<220> FEATURE:
<223> OTHER INFORMATION: Probe for ER segment 8

<400> SEQUENCE: 58
ccggaacatt tgcgatgtgg aaga                                                   24

<210> SEQ ID NO 59
<211> LENGTH: 22
<212> TYPE: DNA
<213> ORGANISM: Artificial
<220> FEATURE:
<223> OTHER INFORMATION: Forward primer for ER segment 7

<400> SEQUENCE: 59
tcaacacttc agtctccata tt                                         22

<210> SEQ ID NO 60
<211> LENGTH: 22
<212> TYPE: DNA
<213> ORGANISM: Artificial
<220> FEATURE:
<223> OTHER INFORMATION: Reverse primer for ER segment 7

<400> SEQUENCE: 60
gcaatgaaag attgtggtat ga                                         22

<210> SEQ ID NO 61
<211> LENGTH: 24
<212> TYPE: DNA
<213> ORGANISM: Artificial
<220> FEATURE:
<223> OTHER INFORMATION: Probe for ER segment 7

<400> SEQUENCE: 61
tatgcatcgc gccaattgtc caac                                       24

<210> SEQ ID NO 62
<211> LENGTH: 22
<212> TYPE: DNA
<213> ORGANISM: Artificial
<220> FEATURE:
<223> OTHER INFORMATION: Forward primer for ER segment 7

<400> SEQUENCE: 62
ctggctgaca aagctaattt ac                                         22

<210> SEQ ID NO 63
<211> LENGTH: 21
<212> TYPE: DNA
<213> ORGANISM: Artificial
<220> FEATURE:
<223> OTHER INFORMATION: Reverse primer for ER segment 7

<400> SEQUENCE: 63
ggtcagccaa tctcatatct c                                          21

<210> SEQ ID NO 64
<211> LENGTH: 24
<212> TYPE: DNA
<213> ORGANISM: Artificial
<220> FEATURE:
<223> OTHER INFORMATION: Probe for ER segment 7

<400> SEQUENCE: 64
agttgttact agacgcgacg tccg                                       24

<210> SEQ ID NO 65
<211> LENGTH: 20
<212> TYPE: DNA
<213> ORGANISM: Artificial
<220> FEATURE:

-continued

<223> OTHER INFORMATION: Forward primer for ERVB

<400> SEQUENCE: 65
aacaggcatt cagggctttg                                           20

<210> SEQ ID NO 66
<211> LENGTH: 20
<212> TYPE: DNA
<213> ORGANISM: Artificial
<220> FEATURE:
<223> OTHER INFORMATION: Reverse primer for ERVB

<400> SEQUENCE: 66
ctttgcctct ggagattggc                                           20

<210> SEQ ID NO 67
<211> LENGTH: 27
<212> TYPE: DNA
<213> ORGANISM: Artificial
<220> FEATURE:
<223> OTHER INFORMATION: Probe for ERVB

<400> SEQUENCE: 67
tgaacttacc acctcggtca tggtgtt                                   27

<210> SEQ ID NO 68
<211> LENGTH: 20
<212> TYPE: DNA
<213> ORGANISM: Artificial
<220> FEATURE:
<223> OTHER INFORMATION: Forward primer for ERVB

<400> SEQUENCE: 68
ggcacctcaa ccgctaattt                                           20

<210> SEQ ID NO 69
<211> LENGTH: 20
<212> TYPE: DNA
<213> ORGANISM: Artificial
<220> FEATURE:
<223> OTHER INFORMATION: Reverse primer for ERVB

<400> SEQUENCE: 69
ctcccgacgt gttgagaaac                                           20

<210> SEQ ID NO 70
<211> LENGTH: 24
<212> TYPE: DNA
<213> ORGANISM: Artificial
<220> FEATURE:
<223> OTHER INFORMATION: Probe for ERVB

<400> SEQUENCE: 70
tgctatcaag acggcgccta ctgt                                      24

<210> SEQ ID NO 71
<211> LENGTH: 20
<212> TYPE: DNA
<213> ORGANISM: Artificial
<220> FEATURE:
<223> OTHER INFORMATION: Forward primer for ERVB

<400> SEQUENCE: 71
ctgtgcaagt ctgggaaacc                                           20

-continued

```
<210> SEQ ID NO 72
<211> LENGTH: 20
<212> TYPE: DNA
<213> ORGANISM: Artificial
<220> FEATURE:
<223> OTHER INFORMATION: Reverse primer for ERVB

<400> SEQUENCE: 72
tgccttgcaa gtgtatgctc                                               20

<210> SEQ ID NO 73
<211> LENGTH: 21
<212> TYPE: DNA
<213> ORGANISM: Artificial
<220> FEATURE:
<223> OTHER INFORMATION: Probe for ERVB

<400> SEQUENCE: 73
agctggactg gctgcttccc a                                             21

<210> SEQ ID NO 74
<211> LENGTH: 20
<212> TYPE: DNA
<213> ORGANISM: Artificial
<220> FEATURE:
<223> OTHER INFORMATION: Forward primer for ERVB

<400> SEQUENCE: 74
tccggtgaca ggtatgatcg                                               20

<210> SEQ ID NO 75
<211> LENGTH: 20
<212> TYPE: DNA
<213> ORGANISM: Artificial
<220> FEATURE:
<223> OTHER INFORMATION: Reverse primer for ERVB

<400> SEQUENCE: 75
atcgcttcca gctcatcact                                               20

<210> SEQ ID NO 76
<211> LENGTH: 24
<212> TYPE: DNA
<213> ORGANISM: Artificial
<220> FEATURE:
<223> OTHER INFORMATION: Probe for ERVB

<400> SEQUENCE: 76
tctcatgtat cacgggcacg gaca                                          24

<210> SEQ ID NO 77
<211> LENGTH: 20
<212> TYPE: DNA
<213> ORGANISM: Artificial
<220> FEATURE:
<223> OTHER INFORMATION: Forward primer for ERVB

<400> SEQUENCE: 77
gtgctcgccg atgaagaaat                                               20

<210> SEQ ID NO 78
<211> LENGTH: 20
<212> TYPE: DNA
<213> ORGANISM: Artificial
<220> FEATURE:
<223> OTHER INFORMATION: Reverse primer for ERVB
```

-continued

<400> SEQUENCE: 78
gtcgcgctta tcttctagcc                                              20

<210> SEQ ID NO 79
<211> LENGTH: 27
<212> TYPE: DNA
<213> ORGANISM: Artificial
<220> FEATURE:
<223> OTHER INFORMATION: Probe for ERVB

<400> SEQUENCE: 79
tttgcttcag ctgacaaatt ggccaga                                      27

<210> SEQ ID NO 80
<211> LENGTH: 20
<212> TYPE: DNA
<213> ORGANISM: Artificial
<220> FEATURE:
<223> OTHER INFORMATION: Forward primer for ERVB

<400> SEQUENCE: 80
aacgctttcg gagcatgttt                                              20

<210> SEQ ID NO 81
<211> LENGTH: 20
<212> TYPE: DNA
<213> ORGANISM: Artificial
<220> FEATURE:
<223> OTHER INFORMATION: Reverse primer for ERVB

<400> SEQUENCE: 81
aatcgtcggt agctctcaca                                              20

<210> SEQ ID NO 82
<211> LENGTH: 24
<212> TYPE: DNA
<213> ORGANISM: Artificial
<220> FEATURE:
<223> OTHER INFORMATION: Probe for ERVB

<400> SEQUENCE: 82
acattgcact tgccctccgt gaca                                         24

<210> SEQ ID NO 83
<211> LENGTH: 20
<212> TYPE: DNA
<213> ORGANISM: Artificial
<220> FEATURE:
<223> OTHER INFORMATION: Forward primer for ERVB

<400> SEQUENCE: 83
ctgctcgcag tgagaaactt                                              20

<210> SEQ ID NO 84
<211> LENGTH: 20
<212> TYPE: DNA
<213> ORGANISM: Artificial
<220> FEATURE:
<223> OTHER INFORMATION: Reverse primer for ERVB

<400> SEQUENCE: 84
gtagtatgca tcgcgccaat                                              20

<210> SEQ ID NO 85
<211> LENGTH: 21

-continued

```
<212> TYPE: DNA
<213> ORGANISM: Artificial
<220> FEATURE:
<223> OTHER INFORMATION: Probe for ERVB

<400> SEQUENCE: 85
acgcaacagc gttcagagcc a                                              21

<210> SEQ ID NO 86
<211> LENGTH: 20
<212> TYPE: DNA
<213> ORGANISM: Artificial
<220> FEATURE:
<223> OTHER INFORMATION: Forward primer for ERVB

<400> SEQUENCE: 86
gatgttgaag agcgttgtgc                                                20

<210> SEQ ID NO 87
<211> LENGTH: 20
<212> TYPE: DNA
<213> ORGANISM: Artificial
<220> FEATURE:
<223> OTHER INFORMATION: Reverse primer for ERVB

<400> SEQUENCE: 87
gacgtcgcgt ctagtaacaa                                                20

<210> SEQ ID NO 88
<211> LENGTH: 26
<212> TYPE: DNA
<213> ORGANISM: Artificial
<220> FEATURE:
<223> OTHER INFORMATION: Probe for ERVB

<400> SEQUENCE: 88
tgtcagccag tcctttgatc agtcgt                                         26

<210> SEQ ID NO 89
<211> LENGTH: 20
<212> TYPE: DNA
<213> ORGANISM: Artificial
<220> FEATURE:
<223> OTHER INFORMATION: Forward primer for ERVB

<400> SEQUENCE: 89
gaacgctgtt gcgtcaattc                                                20

<210> SEQ ID NO 90
<211> LENGTH: 20
<212> TYPE: DNA
<213> ORGANISM: Artificial
<220> FEATURE:
<223> OTHER INFORMATION: Reverse primer for ERVB

<400> SEQUENCE: 90
agccattgtt gtaccagtca                                                20

<210> SEQ ID NO 91
<211> LENGTH: 23
<212> TYPE: DNA
<213> ORGANISM: Artificial
<220> FEATURE:
<223> OTHER INFORMATION: Probe for ERVB

<400> SEQUENCE: 91
```

-continued

```
tgcatcgcgc caattgtcca gca                                        23

<210> SEQ ID NO 92
<211> LENGTH: 22
<212> TYPE: DNA
<213> ORGANISM: Artificial
<220> FEATURE:
<223> OTHER INFORMATION: Forward primer for ERVB

<400> SEQUENCE: 92
tcaacaccat gaggaagaga aa                                         22

<210> SEQ ID NO 93
<211> LENGTH: 20
<212> TYPE: DNA
<213> ORGANISM: Artificial
<220> FEATURE:
<223> OTHER INFORMATION: Reverse primer for ERVB

<400> SEQUENCE: 93
ttgcacaacg ctcttcaaca                                           20

<210> SEQ ID NO 94
<211> LENGTH: 27
<212> TYPE: DNA
<213> ORGANISM: Artificial
<220> FEATURE:
<223> OTHER INFORMATION: Probe for ERVB

<400> SEQUENCE: 94
tctgaactcc gtctagagaa cgggaca                                    27

<210> SEQ ID NO 95
<211> LENGTH: 20
<212> TYPE: DNA
<213> ORGANISM: Artificial
<220> FEATURE:
<223> OTHER INFORMATION: Forward primer for ERVB

<400> SEQUENCE: 95
gctgcattag catcgcagaa                                           20

<210> SEQ ID NO 96
<211> LENGTH: 19
<212> TYPE: DNA
<213> ORGANISM: Artificial
<220> FEATURE:
<223> OTHER INFORMATION: Reverse primer for ERVB

<400> SEQUENCE: 96
cacgcggatc atacgctac                                            19

<210> SEQ ID NO 97
<211> LENGTH: 24
<212> TYPE: DNA
<213> ORGANISM: Artificial
<220> FEATURE:
<223> OTHER INFORMATION: Probe for ERVB

<400> SEQUENCE: 97
acgttcccat ctcacagctg tcgc                                      24

<210> SEQ ID NO 98
<211> LENGTH: 20
<212> TYPE: DNA
<213> ORGANISM: Artificial
```

-continued

```
<220> FEATURE:
<223> OTHER INFORMATION: Forward primer for ERVB

<400> SEQUENCE: 98
gccctgaaat gtctgaagca                                                20

<210> SEQ ID NO 99
<211> LENGTH: 20
<212> TYPE: DNA
<213> ORGANISM: Artificial
<220> FEATURE:
<223> OTHER INFORMATION: Reverse primer for ERVB

<400> SEQUENCE: 99
tcggctgagt ataccgacac                                                20

<210> SEQ ID NO 100
<211> LENGTH: 26
<212> TYPE: DNA
<213> ORGANISM: Artificial
<220> FEATURE:
<223> OTHER INFORMATION: Probe for ERVB

<400> SEQUENCE: 100
tgcgtcgcta cgacttgatg tttcac                                         26

<210> SEQ ID NO 101
<211> LENGTH: 20
<212> TYPE: DNA
<213> ORGANISM: Artificial
<220> FEATURE:
<223> OTHER INFORMATION: Forward primer for ERVB

<400> SEQUENCE: 101
tcggtatact cagccgagac                                                20

<210> SEQ ID NO 102
<211> LENGTH: 20
<212> TYPE: DNA
<213> ORGANISM: Artificial
<220> FEATURE:
<223> OTHER INFORMATION: Reverse primer for ERVB

<400> SEQUENCE: 102
gctgttatcc gaatggtcgt                                                20

<210> SEQ ID NO 103
<211> LENGTH: 27
<212> TYPE: DNA
<213> ORGANISM: Artificial
<220> FEATURE:
<223> OTHER INFORMATION: Probe for ERVB

<400> SEQUENCE: 103
tggttcacgt ctcaacttgt tgtacgc                                        27

<210> SEQ ID NO 104
<211> LENGTH: 20
<212> TYPE: DNA
<213> ORGANISM: Artificial
<220> FEATURE:
<223> OTHER INFORMATION: Forward primer for ERVB

<400> SEQUENCE: 104
acgaccattc ggataacagc                                                20
```

-continued

```
<210> SEQ ID NO 105
<211> LENGTH: 20
<212> TYPE: DNA
<213> ORGANISM: Artificial
<220> FEATURE:
<223> OTHER INFORMATION: Reverse primer for ERVB

<400> SEQUENCE: 105
tctgattaaa cgcggcatca                                                       20

<210> SEQ ID NO 106
<211> LENGTH: 21
<212> TYPE: DNA
<213> ORGANISM: Artificial
<220> FEATURE:
<223> OTHER INFORMATION: Probe for ERVB

<400> SEQUENCE: 106
accgcaacgc aacctgttgg t                                                     21

<210> SEQ ID NO 107
<211> LENGTH: 20
<212> TYPE: DNA
<213> ORGANISM: Artificial
<220> FEATURE:
<223> OTHER INFORMATION: Forward primer for ERVB

<400> SEQUENCE: 107
gctgcattag catcgcagaa                                                       20

<210> SEQ ID NO 108
<211> LENGTH: 20
<212> TYPE: DNA
<213> ORGANISM: Artificial
<220> FEATURE:
<223> OTHER INFORMATION: Reverse primer for ERVB

<400> SEQUENCE: 108
cgcagatcat acgctacgac                                                       20

<210> SEQ ID NO 109
<211> LENGTH: 25
<212> TYPE: DNA
<213> ORGANISM: Artificial
<220> FEATURE:
<223> OTHER INFORMATION: Probe for ERVB

<400> SEQUENCE: 109
tcccatctca cagctgtcgc tttga                                                 25

<210> SEQ ID NO 110
<211> LENGTH: 20
<212> TYPE: DNA
<213> ORGANISM: Artificial
<220> FEATURE:
<223> OTHER INFORMATION: Forward primer for ERVB

<400> SEQUENCE: 110
ccaatgggaa cgcgtaatgt                                                       20

<210> SEQ ID NO 111
<211> LENGTH: 20
<212> TYPE: DNA
<213> ORGANISM: Artificial
<220> FEATURE:
<223> OTHER INFORMATION: Reverse primer for ERVB
```

-continued

<400> SEQUENCE: 111
cttcagcgaa tgacccttgg                                                  20

<210> SEQ ID NO 112
<211> LENGTH: 22
<212> TYPE: DNA
<213> ORGANISM: Artificial
<220> FEATURE:
<223> OTHER INFORMATION: Probe for ERVB

<400> SEQUENCE: 112
ccagcccgtc agactagagg ca                                               22

<210> SEQ ID NO 113
<211> LENGTH: 20
<212> TYPE: DNA
<213> ORGANISM: Artificial
<220> FEATURE:
<223> OTHER INFORMATION: Forward primer for ERVB

<400> SEQUENCE: 113
taccaagacg ttaccgctga                                                  20

<210> SEQ ID NO 114
<211> LENGTH: 20
<212> TYPE: DNA
<213> ORGANISM: Artificial
<220> FEATURE:
<223> OTHER INFORMATION: Reverse primer for ERVB

<400> SEQUENCE: 114
cattacgcgt tcccattggt                                                  20

<210> SEQ ID NO 115
<211> LENGTH: 24
<212> TYPE: DNA
<213> ORGANISM: Artificial
<220> FEATURE:
<223> OTHER INFORMATION: Probe for ERVB

<400> SEQUENCE: 115
tgctctcgcc aactcgtcaa acgg                                             24

<210> SEQ ID NO 116
<211> LENGTH: 20
<212> TYPE: DNA
<213> ORGANISM: Artificial
<220> FEATURE:
<223> OTHER INFORMATION: Forward primer for ERVB

<400> SEQUENCE: 116
gccagccaac ataacacaca                                                  20

<210> SEQ ID NO 117
<211> LENGTH: 20
<212> TYPE: DNA
<213> ORGANISM: Artificial
<220> FEATURE:
<223> OTHER INFORMATION: Reverse primer for ERVB

<400> SEQUENCE: 117
tgcctcttgt atcacgctca                                                  20

<210> SEQ ID NO 118

-continued

```
<211> LENGTH: 24
<212> TYPE: DNA
<213> ORGANISM: Artificial
<220> FEATURE:
<223> OTHER INFORMATION: Probe for ERVB

<400> SEQUENCE: 118
aggctcctgg tctttcgacc atcc                                            24

<210> SEQ ID NO 119
<211> LENGTH: 20
<212> TYPE: DNA
<213> ORGANISM: Artificial
<220> FEATURE:
<223> OTHER INFORMATION: Forward primer for ERVB

<400> SEQUENCE: 119
ggatggtttc gttgctaccc                                                 20

<210> SEQ ID NO 120
<211> LENGTH: 20
<212> TYPE: DNA
<213> ORGANISM: Artificial
<220> FEATURE:
<223> OTHER INFORMATION: Reverse primer for ERVB

<400> SEQUENCE: 120
ccacaatggg ctgaactgag                                                 20

<210> SEQ ID NO 121
<211> LENGTH: 23
<212> TYPE: DNA
<213> ORGANISM: Artificial
<220> FEATURE:
<223> OTHER INFORMATION: Probe for ERVB

<400> SEQUENCE: 121
cgcagatgca cgttctccag tgc                                             23

<210> SEQ ID NO 122
<211> LENGTH: 20
<212> TYPE: DNA
<213> ORGANISM: Artificial
<220> FEATURE:
<223> OTHER INFORMATION: Forward primer for ERVB

<400> SEQUENCE: 122
gccaagtaca acgcatgtct                                                 20

<210> SEQ ID NO 123
<211> LENGTH: 20
<212> TYPE: DNA
<213> ORGANISM: Artificial
<220> FEATURE:
<223> OTHER INFORMATION: Reverse primer for ERVB

<400> SEQUENCE: 123
agatcttctg gccgaacaca                                                 20

<210> SEQ ID NO 124
<211> LENGTH: 23
<212> TYPE: DNA
<213> ORGANISM: Artificial
<220> FEATURE:
<223> OTHER INFORMATION: Probe for ERVB

<400> SEQUENCE: 124
```

-continued cgccgtcacg tcaagattac gca                                                          23

<210> SEQ ID NO 125
<211> LENGTH: 20
<212> TYPE: DNA
<213> ORGANISM: Artificial
<220> FEATURE:
<223> OTHER INFORMATION: Forward primer for ERVB

<400> SEQUENCE: 125
accgacagca gaacatggta                                                              20

<210> SEQ ID NO 126
<211> LENGTH: 20
<212> TYPE: DNA
<213> ORGANISM: Artificial
<220> FEATURE:
<223> OTHER INFORMATION: Reverse primer for ERVB

<400> SEQUENCE: 126
agacatgcgt tgtacttggc                                                              20

<210> SEQ ID NO 127
<211> LENGTH: 24
<212> TYPE: DNA
<213> ORGANISM: Artificial
<220> FEATURE:
<223> OTHER INFORMATION: Probe for ERVB

<400> SEQUENCE: 127
acctctgtac ctctgtcgga gcgt                                                         24

<210> SEQ ID NO 128
<211> LENGTH: 20
<212> TYPE: DNA
<213> ORGANISM: Artificial
<220> FEATURE:
<223> OTHER INFORMATION: Forward primer for ERVB

<400> SEQUENCE: 128
taaagcggtt gagggcacta                                                              20

<210> SEQ ID NO 129
<211> LENGTH: 20
<212> TYPE: DNA
<213> ORGANISM: Artificial
<220> FEATURE:
<223> OTHER INFORMATION: Reverse primer for ERVB

<400> SEQUENCE: 129
atggcctcgt ttgttgacag                                                              20

<210> SEQ ID NO 130
<211> LENGTH: 27
<212> TYPE: DNA
<213> ORGANISM: Artificial
<220> FEATURE:
<223> OTHER INFORMATION: Probe for ERVB

<400> SEQUENCE: 130
tccaacgttc caaatctgtt cctccct                                                      27

<210> SEQ ID NO 131
<211> LENGTH: 20
<212> TYPE: DNA

-continued

```
<213> ORGANISM: Artificial
<220> FEATURE:
<223> OTHER INFORMATION: Forward primer for ERVB

<400> SEQUENCE: 131
gggattacgt gcacagacac                                                      20

<210> SEQ ID NO 132
<211> LENGTH: 20
<212> TYPE: DNA
<213> ORGANISM: Artificial
<220> FEATURE:
<223> OTHER INFORMATION: Reverse primer for ERVB

<400> SEQUENCE: 132
tggtctacca cgcgtatgtt                                                      20

<210> SEQ ID NO 133
<211> LENGTH: 25
<212> TYPE: DNA
<213> ORGANISM: Artificial
<220> FEATURE:
<223> OTHER INFORMATION: Probe for ERVB

<400> SEQUENCE: 133
agccatggat acgcttctgt ccagt                                                25

<210> SEQ ID NO 134
<211> LENGTH: 20
<212> TYPE: DNA
<213> ORGANISM: Artificial
<220> FEATURE:
<223> OTHER INFORMATION: Forward primer for ERVB

<400> SEQUENCE: 134
ttcggagggt gattggagac                                                      20

<210> SEQ ID NO 135
<211> LENGTH: 20
<212> TYPE: DNA
<213> ORGANISM: Artificial
<220> FEATURE:
<223> OTHER INFORMATION: Reverse primer for ERVB

<400> SEQUENCE: 135
tgaaagcgcg atctttaccg                                                      20

<210> SEQ ID NO 136
<211> LENGTH: 27
<212> TYPE: DNA
<213> ORGANISM: Artificial
<220> FEATURE:
<223> OTHER INFORMATION: Probe for ERVB

<400> SEQUENCE: 136
tgtctcagaa tctgtgttcc tgcagct                                              27

<210> SEQ ID NO 137
<211> LENGTH: 20
<212> TYPE: DNA
<213> ORGANISM: Artificial
<220> FEATURE:
<223> OTHER INFORMATION: Forward primer for ERVB

<400> SEQUENCE: 137
acttcctgca tcagaacgga                                                      20
```

<210> SEQ ID NO 138
<211> LENGTH: 20
<212> TYPE: DNA
<213> ORGANISM: Artificial
<220> FEATURE:
<223> OTHER INFORMATION: Reverse primer for ERVB

<400> SEQUENCE: 138
tgaggctgac aactgaccat                                                        20

<210> SEQ ID NO 139
<211> LENGTH: 23
<212> TYPE: DNA
<213> ORGANISM: Artificial
<220> FEATURE:
<223> OTHER INFORMATION: Probe for ERVB

<400> SEQUENCE: 139
tccgtctaaa ccggtgcatc cgt                                                    23

<210> SEQ ID NO 140
<211> LENGTH: 20
<212> TYPE: DNA
<213> ORGANISM: Artificial
<220> FEATURE:
<223> OTHER INFORMATION: Forward primer for ERVB

<400> SEQUENCE: 140
agcggagagg tgactaatgg                                                        20

<210> SEQ ID NO 141
<211> LENGTH: 20
<212> TYPE: DNA
<213> ORGANISM: Artificial
<220> FEATURE:
<223> OTHER INFORMATION: Reverse primer for ERVB

<400> SEQUENCE: 141
tccgttctga tgcaggaagt                                                        20

<210> SEQ ID NO 142
<211> LENGTH: 25
<212> TYPE: DNA
<213> ORGANISM: Artificial
<220> FEATURE:
<223> OTHER INFORMATION: Probe for ERVB

<400> SEQUENCE: 142
acggagatcc accatgtcaa acggt                                                  25

<210> SEQ ID NO 143
<211> LENGTH: 20
<212> TYPE: DNA
<213> ORGANISM: Artificial
<220> FEATURE:
<223> OTHER INFORMATION: Forward primer for ERVB

<400> SEQUENCE: 143
gttgacgccg gatcttacac                                                        20

<210> SEQ ID NO 144
<211> LENGTH: 20
<212> TYPE: DNA
<213> ORGANISM: Artificial
<220> FEATURE:

<223> OTHER INFORMATION: Reverse primer for ERVB

<400> SEQUENCE: 144
tcatcatagc cagcagcgta                                          20

<210> SEQ ID NO 145
<211> LENGTH: 24
<212> TYPE: DNA
<213> ORGANISM: Artificial
<220> FEATURE:
<223> OTHER INFORMATION: Probe for ERVB

<400> SEQUENCE: 145
tgcaccgttt ctgtagtgcg tccc                                     24

<210> SEQ ID NO 146
<211> LENGTH: 20
<212> TYPE: DNA
<213> ORGANISM: Artificial
<220> FEATURE:
<223> OTHER INFORMATION: Forward primer for ERVB

<400> SEQUENCE: 146
gataccgcgc ttatccaacc                                          20

<210> SEQ ID NO 147
<211> LENGTH: 20
<212> TYPE: DNA
<213> ORGANISM: Artificial
<220> FEATURE:
<223> OTHER INFORMATION: Reverse primer for ERVB

<400> SEQUENCE: 147
gttctgcttc catgcctgag                                          20

<210> SEQ ID NO 148
<211> LENGTH: 24
<212> TYPE: DNA
<213> ORGANISM: Artificial
<220> FEATURE:
<223> OTHER INFORMATION: Probe for ERVB

<400> SEQUENCE: 148
acctgaccat ctgccaatcg ctgc                                     24

<210> SEQ ID NO 149
<211> LENGTH: 20
<212> TYPE: DNA
<213> ORGANISM: Artificial
<220> FEATURE:
<223> OTHER INFORMATION: Forward primer for ERVB

<400> SEQUENCE: 149
acacgataca cgcaccgata                                          20

<210> SEQ ID NO 150
<211> LENGTH: 20
<212> TYPE: DNA
<213> ORGANISM: Artificial
<220> FEATURE:
<223> OTHER INFORMATION: Reverse primer for ERVB

<400> SEQUENCE: 150
cttcgaccag ctgctttacc                                          20

-continued

```
<210> SEQ ID NO 151
<211> LENGTH: 20
<212> TYPE: DNA
<213> ORGANISM: Artificial
<220> FEATURE:
<223> OTHER INFORMATION: Probe for ERVB

<400> SEQUENCE: 151
agtgcgaatc gccgcagcca                                                      20

<210> SEQ ID NO 152
<211> LENGTH: 20
<212> TYPE: DNA
<213> ORGANISM: Artificial
<220> FEATURE:
<223> OTHER INFORMATION: Forward primer for ERVB

<400> SEQUENCE: 152
ctcgagaccg gttagagtga                                                      20

<210> SEQ ID NO 153
<211> LENGTH: 20
<212> TYPE: DNA
<213> ORGANISM: Artificial
<220> FEATURE:
<223> OTHER INFORMATION: Reverse primer for ERVB

<400> SEQUENCE: 153
tggataagcg cggtatcagt                                                      20

<210> SEQ ID NO 154
<211> LENGTH: 24
<212> TYPE: DNA
<213> ORGANISM: Artificial
<220> FEATURE:
<223> OTHER INFORMATION: Probe for ERVB

<400> SEQUENCE: 154
tcgaccagct gctttaccac tggt                                                 24

<210> SEQ ID NO 155
<211> LENGTH: 20
<212> TYPE: DNA
<213> ORGANISM: Artificial
<220> FEATURE:
<223> OTHER INFORMATION: Forward primer for ERVB

<400> SEQUENCE: 155
gttgccattg cttctcgtct                                                      20

<210> SEQ ID NO 156
<211> LENGTH: 20
<212> TYPE: DNA
<213> ORGANISM: Artificial
<220> FEATURE:
<223> OTHER INFORMATION: Reverse primer for ERVB

<400> SEQUENCE: 156
ttccaatcac tagcgtgcag                                                      20

<210> SEQ ID NO 157
<211> LENGTH: 27
<212> TYPE: DNA
<213> ORGANISM: Artificial
<220> FEATURE:
<223> OTHER INFORMATION: Probe for ERVB
```

-continued

```
<400> SEQUENCE: 157
tccaatcagc aacccggaga tttgtgt                                        27

<210> SEQ ID NO 158
<211> LENGTH: 20
<212> TYPE: DNA
<213> ORGANISM: Artificial
<220> FEATURE:
<223> OTHER INFORMATION: Forward primer for ERVB

<400> SEQUENCE: 158
ctcagggacg gtgtcaagag                                                20

<210> SEQ ID NO 159
<211> LENGTH: 20
<212> TYPE: DNA
<213> ORGANISM: Artificial
<220> FEATURE:
<223> OTHER INFORMATION: Reverse primer for ERVB

<400> SEQUENCE: 159
gctcgtggct caaagtttct                                                20

<210> SEQ ID NO 160
<211> LENGTH: 26
<212> TYPE: DNA
<213> ORGANISM: Artificial
<220> FEATURE:
<223> OTHER INFORMATION: Probe for ERVB

<400> SEQUENCE: 160
acctgcgcaa atgtcttgaa acctgt                                         26

<210> SEQ ID NO 161
<211> LENGTH: 20
<212> TYPE: DNA
<213> ORGANISM: Artificial
<220> FEATURE:
<223> OTHER INFORMATION: Forward primer for ERVB

<400> SEQUENCE: 161
agcgcatcaa tgaagacaaa                                                20

<210> SEQ ID NO 162
<211> LENGTH: 20
<212> TYPE: DNA
<213> ORGANISM: Artificial
<220> FEATURE:
<223> OTHER INFORMATION: Reverse primer for ERVB

<400> SEQUENCE: 162
acctgcgcaa atgtcttgaa                                                20

<210> SEQ ID NO 163
<211> LENGTH: 20
<212> TYPE: DNA
<213> ORGANISM: Artificial
<220> FEATURE:
<223> OTHER INFORMATION: Probe for ERVB

<400> SEQUENCE: 163
tgacaccgtc cctgaggccg                                                20

<210> SEQ ID NO 164
<211> LENGTH: 20
```

-continued

```
<212> TYPE: DNA
<213> ORGANISM: Artificial
<220> FEATURE:
<223> OTHER INFORMATION: Forward primer for ERVB

<400> SEQUENCE: 164
tccggtgaca ggtatgatcg                                               20

<210> SEQ ID NO 165
<211> LENGTH: 20
<212> TYPE: DNA
<213> ORGANISM: Artificial
<220> FEATURE:
<223> OTHER INFORMATION: Reverse primer for ERVB

<400> SEQUENCE: 165
atcgcttcca gctcatcact                                               20

<210> SEQ ID NO 166
<211> LENGTH: 24
<212> TYPE: DNA
<213> ORGANISM: Artificial
<220> FEATURE:
<223> OTHER INFORMATION: Probe for ERVB

<400> SEQUENCE: 166
tctcatgtat cacgggcacg gaca                                          24

<210> SEQ ID NO 167
<211> LENGTH: 21
<212> TYPE: DNA
<213> ORGANISM: Artificial
<220> FEATURE:
<223> OTHER INFORMATION: Forward primer for ERVB

<400> SEQUENCE: 167
gcggttgagg gcactagatt c                                             21

<210> SEQ ID NO 168
<211> LENGTH: 20
<212> TYPE: DNA
<213> ORGANISM: Artificial
<220> FEATURE:
<223> OTHER INFORMATION: Reverse primer for ERVB

<400> SEQUENCE: 168
gcaacatcca acgttccaaa                                               20

<210> SEQ ID NO 169
<211> LENGTH: 19
<212> TYPE: DNA
<213> ORGANISM: Artificial
<220> FEATURE:
<223> OTHER INFORMATION: Probe for ERVB

<400> SEQUENCE: 169
aatacttagg gagaaacag                                                19

<210> SEQ ID NO 170
<211> LENGTH: 18
<212> TYPE: RNA
<213> ORGANISM: Simian 11 rotavirus
<220> FEATURE:
<221> NAME/KEY: 5'UTR
<222> LOCATION: (1)..(18)
<223> OTHER INFORMATION: Segment 1
```

-continued

```
<400> SEQUENCE: 170
ggcuauuaaa gcguaca                                                    18

<210> SEQ ID NO 171
<211> LENGTH: 17
<212> TYPE: RNA
<213> ORGANISM: Simian 11 rotavirus
<220> FEATURE:
<221> NAME/KEY: 3'UTR
<222> LOCATION: (1)..(17)
<223> OTHER INFORMATION: Segment 1

<400> SEQUENCE: 171
aacgcuuaga ugugacc                                                    17

<210> SEQ ID NO 172
<211> LENGTH: 16
<212> TYPE: RNA
<213> ORGANISM: Simian 11 rotavirus
<220> FEATURE:
<221> NAME/KEY: 5'UTR
<222> LOCATION: (1)..(16)
<223> OTHER INFORMATION: Segment 2

<400> SEQUENCE: 172
ggcuauuaaa ggcuca                                                     16

<210> SEQ ID NO 173
<211> LENGTH: 28
<212> TYPE: RNA
<213> ORGANISM: Simian 11 rotavirus
<220> FEATURE:
<221> NAME/KEY: 3'UTR
<222> LOCATION: (1)..(28)
<223> OTHER INFORMATION: Segment 2

<400> SEQUENCE: 173
acgccaaccc cauuguggag auaugacc                                        28

<210> SEQ ID NO 174
<211> LENGTH: 49
<212> TYPE: RNA
<213> ORGANISM: Simian 11 rotavirus
<220> FEATURE:
<221> NAME/KEY: 5'UTR
<222> LOCATION: (1)..(49)
<223> OTHER INFORMATION: Segment 3

<400> SEQUENCE: 174
ggcuuuuaaa gcaguaccag uaguguguuu uaccucugau ggguguaaac               49

<210> SEQ ID NO 175
<211> LENGTH: 34
<212> TYPE: RNA
<213> ORGANISM: Simian 11 rotavirus
<220> FEATURE:
<221> NAME/KEY: 3'UTR
<222> LOCATION: (1)..(34)
<223> OTHER INFORMATION: Segment 3

<400> SEQUENCE: 175
gcuaaaaacu uaacacacua gucaugaugu gacc                                34

<210> SEQ ID NO 176
<211> LENGTH: 9
<212> TYPE: RNA
<213> ORGANISM: Simian 11 rotavirus
```

-continued

```
<220> FEATURE:
<221> NAME/KEY: 5'UTR
<222> LOCATION: (1)..(9)
<223> OTHER INFORMATION: Segment 4

<400> SEQUENCE: 176 ggcuauaaa                                                            9

<210> SEQ ID NO 177
<211> LENGTH: 22
<212> TYPE: RNA
<213> ORGANISM: Simian 11 rotavirus
<220> FEATURE:
<221> NAME/KEY: 3'UTR
<222> LOCATION: (1)..(22)
<223> OTHER INFORMATION: Segment 4

<400> SEQUENCE: 177
guaauuucua gaggauguga cc                                            22

<210> SEQ ID NO 178
<211> LENGTH: 30
<212> TYPE: RNA
<213> ORGANISM: Simian 11 rotavirus
<220> FEATURE:
<221> NAME/KEY: 5'UTR
<222> LOCATION: (1)..(30)
<223> OTHER INFORMATION: Segment 5

<400> SEQUENCE: 178
ggcuuuuuuu ugaaaagucu uguguuagcc                                    30

<210> SEQ ID NO 179
<211> LENGTH: 93
<212> TYPE: RNA
<213> ORGANISM: Simian 11 rotavirus
<220> FEATURE:
<221> NAME/KEY: 3'UTR
<222> LOCATION: (1)..(93)
<223> OTHER INFORMATION: Segment 5

<400> SEQUENCE: 179
aauuacuaau gucacuaucu aauuauacag uauuuagcca ucacaagacc guccagacua    60
gaguagcgcc uagcuggcaa aauacuguga acc                                93

<210> SEQ ID NO 180
<211> LENGTH: 23
<212> TYPE: RNA
<213> ORGANISM: Simian 11 rotavirus
<220> FEATURE:
<221> NAME/KEY: 5'UTR
<222> LOCATION: (1)..(23)
<223> OTHER INFORMATION: Segment 6

<400> SEQUENCE: 180
ggcuuuuaaa cgaagucuuc aac                                           23

<210> SEQ ID NO 181
<211> LENGTH: 139
<212> TYPE: RNA
<213> ORGANISM: Simian 11 rotavirus
<220> FEATURE:
<221> NAME/KEY: 3'UTR
<222> LOCATION: (1)..(139)
<223> OTHER INFORMATION: Segment 6

<400> SEQUENCE: 181
```
ggaccaagcu aacaacuugg uauccaacuu ggugaguau guagcuauau caagcuguuu          60
gaacucugua aguaaggaua cguauacgca uucgcuacac agaguaauca cucagauggu         120
auagugagag gaugugacc                                                      139

```
<210> SEQ ID NO 182
<211> LENGTH: 34
<212> TYPE: RNA
<213> ORGANISM: Simian 11 rotavirus
<220> FEATURE:
<221> NAME/KEY: 5'UTR
<222> LOCATION: (1)..(34)
<223> OTHER INFORMATION: Segment 7

<400> SEQUENCE: 182
```
ggcauuuaau gcuuuucagu gguugaugcu caag                                      34

```
<210> SEQ ID NO 183
<211> LENGTH: 132
<212> TYPE: RNA
<213> ORGANISM: Simian 11 rotavirus
<220> FEATURE:
<221> NAME/KEY: 3'UTR
<222> LOCATION: (1)..(132)
<223> OTHER INFORMATION: Segment 7

<400> SEQUENCE: 183
```
ccauuuugau acauguugaa caaucaaaua caguguuagu auguugucau cuaugcauaa          60
cccucuauga gcacaauagu uaaaagcuaa cacugucaaa aaccuaaaug gcuauagggg         120
cguuaugugg cc                                                             132

```
<210> SEQ ID NO 184
<211> LENGTH: 46
<212> TYPE: RNA
<213> ORGANISM: Simian 11 rotavirus
<220> FEATURE:
<221> NAME/KEY: 5'UTR
<222> LOCATION: (1)..(46)
<223> OTHER INFORMATION: Segment 8

<400> SEQUENCE: 184
```
ggcuuuuaaa gcgucucagu cgccguuuga gccuugcggu guagcc                        46

```
<210> SEQ ID NO 185
<211> LENGTH: 59
<212> TYPE: RNA
<213> ORGANISM: Simian 11 rotavirus
<220> FEATURE:
<221> NAME/KEY: 3'UTR
<222> LOCATION: (1)..(59)
<223> OTHER INFORMATION: Segment 8

<400> SEQUENCE: 185
```
uucgcuauca auuugaggau gaugauggcu uagcaagaau agaaagcgcu uaugugacc          59

```
<210> SEQ ID NO 186
<211> LENGTH: 48
<212> TYPE: RNA
<213> ORGANISM: Simian 11 rotavirus
<220> FEATURE:
<221> NAME/KEY: 5'UTR
<222> LOCATION: (1)..(48)
<223> OTHER INFORMATION: Segment 9

<400> SEQUENCE: 186
```
ggcuuuaaaa gagagaauuu ccguuuggcu agcgguuagc uccuuuua                      48

-continued

```
<210> SEQ ID NO 187
<211> LENGTH: 33
<212> TYPE: RNA
<213> ORGANISM: Simian 11 rotavirus
<220> FEATURE:
<221> NAME/KEY: 3'UTR
<222> LOCATION: (1)..(33)
<223> OTHER INFORMATION: Segment 9

<400> SEQUENCE: 187
guauaacuua gguuagaauu guaugaugug acc                                33

<210> SEQ ID NO 188
<211> LENGTH: 41
<212> TYPE: RNA
<213> ORGANISM: Simian 11 rotavirus
<220> FEATURE:
<221> NAME/KEY: 5'UTR
<222> LOCATION: (1)..(41)
<223> OTHER INFORMATION: Segment 10

<400> SEQUENCE: 188
ggcuuuuaaa aguucuguuc cgagagagcg cgugcggaaa g                       41

<210> SEQ ID NO 189
<211> LENGTH: 182
<212> TYPE: RNA
<213> ORGANISM: Simian 11 rotavirus
<220> FEATURE:
<221> NAME/KEY: 3'UTR
<222> LOCATION: (1)..(182)
<223> OTHER INFORMATION: Segment 10

<400> SEQUENCE: 189
gagguugagc ugccgucgac uguccucgga agcggcggag uucuuuacag uaagcaccau    60
cggaccugau ggcugacuga gaagccacag ucagccauau cgcguguggc ucaagccuua    120
aucccguuua accaauccgg ucagcaccgg acguuaaugg aaggaacggu cuuaauguga    180
cc                                                                  182

<210> SEQ ID NO 190
<211> LENGTH: 21
<212> TYPE: RNA
<213> ORGANISM: Simian 11 rotavirus
<220> FEATURE:
<221> NAME/KEY: 5'UTR
<222> LOCATION: (1)..(21)
<223> OTHER INFORMATION: Segment 11

<400> SEQUENCE: 190
ggcuuuuaaa gcgcuacagu g                                             21

<210> SEQ ID NO 191
<211> LENGTH: 49
<212> TYPE: RNA
<213> ORGANISM: Simian 11 rotavirus
<220> FEATURE:
<221> NAME/KEY: 3'UTR
<222> LOCATION: (1)..(49)
<223> OTHER INFORMATION: Segment 11

<400> SEQUENCE: 191
gucugaccug ggaacacacu agggagcucc ccacucccgu uuugugacc               49

<210> SEQ ID NO 192
```

-continued

```
<211> LENGTH: 1084
<212> TYPE: DNA
<213> ORGANISM: Equine rotavirus

<400> SEQUENCE: 192
gatatctgct cgcagtgaga atcttacact atggctctga acgctgttgc gtcaattcta      60
ggatctgtgt tgtctaaaca tgaaattgat gatcagttga aaatcattga agatttcatt     120
catgcaatga aagattgtgg tatgatgttg acaattggc gcgatgcata ctacaaactg      180
aggattccaa aaccaatgac cggtacaaca atggctatac agttgaaaaa tatggagact     240
gaagtgttga ggttgagaca tgaatcttgg aagaatggtg aaacgatgaa agacagacta     300
ctacaatcat ttgatgttgg caagaagaat ggatatactg tacttctacc gaaaacaaga     360
aacgcagaag tggttctact aaactctact gttgacatga aattaaaccc atttccttct     420
gatgtagttg atgatttgat taaaaaaaat tcggaactcg aaaacagcat taaaacaata     480
caggaagaag caaacacaaa aatgagatat caagaagagc taattgagga aagggacaga     540
atcatgagtg aaatgaacca acagattata atgctgagaa agaagattac gttcctacgt     600
gagaatcaca gagaaagact tgagttggtt aatcaacacc atgaggaaga gaaaaagatc     660
tacaaaagag agatatctga actccgtcta gagaacggga cattgaattt gaccatttca     720
acgttgaaca agcagtttga caacatgtca cttgatcata tgaaagatat ccaagtctta     780
attgaacatg tttctgatgt tgaagagcgt gtgtcaaagt tgtccagtga gaatgttgta     840
cttagagaag agcaagatga acatatacga ctgatcaaag gactggctga caaagctaat     900
ttacaggtta cattcgta aacaaaatga ctcaagtgag ttgttattag acgcgacgtc     960
cgttcagaga tatgagattg gctgaccacc aattaataaa aacctcataa agaacgtcgt    1020
agtccggatt ggagtctgca actcgactcc atgaagtcgg aatcgctagt aatcgtggat    1080
caga                                                                 1084

<210> SEQ ID NO 193
<211> LENGTH: 3503
<212> TYPE: DNA
<213> ORGANISM: Equine rotavirus

<400> SEQUENCE: 193
atggacacct cggaattctt tgattggtta acagaagaat tcaagaggaa cctatcttac      60
atcaagtcaa tatatacaaa ccccaaaatt gcgaaaatag tttttaaaga agctgacaaa     120
ctgtgggaat cgaaaacact aaactcacag acacccgatg aagtgttaga tgaaatagaa     180
aaattgaagg aatcaactga agatatcgat agtaaactgg aaaaattact aaggttaagg     240
tatttaaccg tgtatgtaga cgataaatct gacaaaagag aaatagtgtt gaaactgatc     300
gataatgtag tgaatctaac atctacagat gacgtattcc attcaatcaa ggctatagaa     360
tttcaagcta aacagtggag gacgaaaaat gcgtccgtgc tgaaaccata ccattacaac     420
ataccaatct gtgaatacat tcgagataat gaaattgaat acatagatac tggtgattac     480
aaatggcaat cggatacatt gcaaggttta atgccgaatt attatcacag aacgcataca     540
ctaattggtt cagttgtatt atcagttctc aaaagaattt caacatatag tgacgaggaa     600
aagaaagctt tgaactacct gtttacaacc atacgcgaat gttactcgga aggatactta     660
gaattgtcat tggataggaa atggtcacat accatttcac aattaaagga agccacgttt     720
agactgtata acaccaaagt aatacatgca gcttgtgcga tggtttcact actccacgca     780
tcaaacataa tgccagaatt cctttgccaa ataatagctg tatacaaaat aattcctgca     840
```

-continued

```
aatgcagcaa aattactatc gtcgccaatg acgttgtaca taggcatagc aacttttcca      900
tctaagatgg tagcatcaac tggtaacgcc tcagaatgtg cttcaatgga cttgccaaat      960
aatgtctttg tcgccaaaga acagattgaa gaatggaatg tggcattcaa agatgatcct     1020
ttaaatgagt cgctgttact tatagaaatg aataagaacc tgaagactga tgtcgacacg     1080
ttcgtaaaaa tatttaattg tttttcggcg acttttcatg ttggacatag aatcgacaat     1140
gcacaggacg cgatagttga tcaggtaacg gttcagtaca ccacagacgt agatcgtgaa     1200
atgtatgata tgtattatta caaactgaaa agtatgttga aggctgaaat taaaaaatat     1260
gttgaggatc atatacatcg tgactaccaa gacgttaccg ctgagtcgtt atctgctctc     1320
gccaactcgt caaacggatt tcagaaagag gtactcttta tcgacagaaa aataaaaaca     1380
accaagaaaa tattgcatct cgatgcagat ttgttagaag gagatttcag agatgtgcgt     1440
aaagtcatgt ctagaggtat accaatggga acgcgtaatg ttccagcccg tcagactaga     1500
ggcatattca tcttgccatg gcaagtagca gcagttcaac acacaatagc ggaatcttta     1560
tacaaaacag ccaagaaagg agcgtaccaa gggtcattcg ctgaagctta tacttcaaag     1620
accgcgtcat aacatatgg agtattggct gaagatactt ctaaggctat gaagataatt     1680
ctttatacag acgtgtcaca atgggacgcc agccaacata acacacaacc atacagatca     1740
gcatggataa atgcaattaa agaggtgaga gaagaaggag gatggtcgaa agaccaggag     1800
cctactatgt taggcataaa cgtgcttgac gcaatgagcg tgatacaaga ggcattgcta     1860
aattcaacgt taatcgttac ctccaccaaa tctaacagaa acatactaac aatcagatat     1920
cacggggtcg cgtcaggaga aaaaacaacg aaggttggta actcattcgc gaacgtggca     1980
ttgattgaaa ctgtactaga tgtcacaaaa caacagatac cagacatcga agtgactcat     2040
ctgagagtgg atggggatga caacgtcgtg tcgatcaaca cagcatgcaa tatatcaaaa     2100
ctacaaactg tgattaaatc caactatcaa aagttaaatg cacgagttaa ggcgcttgcg     2160
tcttacacag gtcttgaaat ggcgaaacga tttattatat gtggaaacat ctttgagaga     2220
ggtgctatac caattttac tgctgaaaga ccatatggca cggacgtctc aatacaatct     2280
atgactggtt catcaatcta ctcatctgcc gtgaacgcat atagagcgtt tggtgataag     2340
tacttaagct ttatgatgga cgtgttggta cctccatcat caacagtgag actgactggc     2400
agattacgag tgttgctatc gccaattacg ttgtttgcga ctggaccttt aagctttgaa     2460
gtgactcaaa atggattagg aggaagatgt agactgtata caccaaatag ccgactgatg     2520
caattattta agatgctgac agacactgta tccgtggcgg taacaccaga agaagtaaaa     2580
ttatatgcaa agacaaatca attcaaggaa agagtgtctg ttatggcaaa tagtctcaac     2640
gcaaaaatta aaacaaatgc tccagcccta attgcgatat tacgagagaa agaagaacag     2700
aaaacattgg gagtgccaaa cgtgcagacg cagaagaaca ggaagcaggt gaatgaggca     2760
ttgaagatac tatctgttcc agaaagaaat gatctaattc caaaaggcta ttacccagaa     2820
gagttgtaca ccttagtgtt atccaactcg aaaatcacat ataaggattt tttaccagtg     2880
cacagtattt accacacgaa taaccatgcc gtcgcgttac ttcataatca attaggagta     2940
acgataagcg agtcaaaacc aataactaaa ccagttaacc acttatacga cattgtagtc     3000
acactatcac caatttctat atcaccaagt gatattttga agcaatcaaa gagatatgac     3060
ctgacatcat acaatggaaa gaaaagattc ttaagtgact tgggattaac ggggaacacc     3120
ttaaaaacat atctcgcctc gaagatgtta ttcagagatc ttttattggc taaatatgat     3180
```

-continued

```
gaattatacca  gtacaccagg  ttttggtgca  acgcaactga  caacaatacc  gttgaatata   3240
cattcagctg  agcaggtttt  cagtataaat  gtcaagctgc  cacctcatct  gtatgaaata   3300
atgatgttaa  tgttgcttta  tgagtatgtc  cactatgtgt  tcatgacaaa  aagaacttac   3360
accgctgtac  tatcaccgat  gtcgcaggat  caatcggtta  aactatctag  tttaatattg   3420
aaaatgcttg  ataatattaa  acttgatgtg  gtgtcattct  ctgatgacgc  ctggtaaacc   3480
atacatataa  aaacccagat  ctg                                             3503

<210> SEQ ID NO 194
<211> LENGTH: 2889
<212> TYPE: DNA
<213> ORGANISM: Equine rotavirus

<400> SEQUENCE: 194
ggaagatatg  atgggtgatt  tagatctaat  cacttctgct  tcacaagcaa  tacaagctac     60
gaatgataaa  aacgacaaac  aaaagatttt  tgatcagttg  gtcaatgact  tgaaaagact    120
gagtaagggc  gtcctacaac  cggacgtcca  atccaaacta  ttggaactat  ccaatataaa    180
tggtctagta  ttcaacgtag  aggtacaaga  agatgtgggtt  aacacgatca  atgaccaacc    240
ggatccaacg  tctatattca  cacaaaacgt  tttccaacta  agaacgacat  tatcaaagac    300
tctattcata  gatgtggacg  ccgaagagta  ttcggtttac  gttcctctag  aagtgcaaaa    360
catttcacct  gtggtgattg  acattagacc  aatacaaaca  tataaaccaa  aaactttaat    420
gtacaaagat  acggcgataa  taccttcaaa  caatgacttg  gtgtcagatc  aatggggagc    480
ggacgaaatc  ctatatgatt  cgcacatgtt  taacgacatt  aacataggcc  agattgaaga    540
ttttgaaacg  tatttgttag  agaaagctgt  agaaattaaa  gattcgctgc  caaatatcaa    600
ccatatatca  caattaagca  aagacacgaa  tcctttcaat  gtgcacaaca  cactatgtct    660
agattttgga  caaaaggagt  attataatct  aatttcagac  agaacgaacc  agtcatttgt    720
ggggagaaga  caagcggtac  aatttgataa  cgttgttgtg  gatgggattg  aacgtacagc    780
gcgcatatcg  ttgagacttc  atccattcga  taaccaaatg  ctgaatttaa  taccccctgaa    840 tttaatacat  gagcagccca  ttattgatgt  aattagagat  taccagctag  tagcggcgga    900
tggtttcgtt  gctaccccaa  aagtaaggct  cgacaaggat  gtgactataa  tcgcagatgc    960
acgttctcca  gtgcttgcaa  gattatgtga  attatcgcct  tacttgcatc  gaacaaggat   1020
cttagattca  atgactcagt  tcagcccatt  gtggaagatt  aacgtttttt  caagttcgat   1080
agagaatgct  aaagactcca  tttataagat  ggctgagatt  tcattcactg  tggccgactc   1140
cgttacctca  gcgctgtcga  cggttaatgt  agcctcagcg  caacaaaccc  tgactgtttt   1200
acttaattca  tgtatattcc  gtcttgagat  tgatccgact  ggaagtcagt  cgaactttgg   1260
tgctgcaata  tcggcagcga  taatgcttgt  tttgttccca  actgatgaag  aaacgatgcc   1320
tacgaatgtt  tttgataatc  tatgcaactt  agtgtataac  gaattgatag  cttgacggt    1380 cgacaggcca  acgttcgtca  aacgcacggg  acaaaccaac  gcatttgaag  ctaatgttaa   1440
tatcggtggg  ggtaatatga  atagagacat  attagcttac  atcaggttta  tactactcag   1500
aagaccatgg  attttgtatc  aacggacata  cgacgaggca  tatgcggctg  atattttcat   1560
tccaaacatt  gacgaagcca  acataaatga  ccaagcttat  gtagctgtaa  atagtttatt   1620
ctcaggcctg  atccaggcag  cacagaggaa  tccgaaccca  gggaggcaaa  tcagtgcgaa   1680
ttcttttaga  aaattgctaa  aatcaatgaa  agatgtgtgt  tcaaacaaat  tgatgccaat   1740
agttagatta  atcaggtata  atattgaaag  gatggcaaga  gtttataagt  ggtttccata   1800
```

```
ttcagccgac ttcgcaaatc gtataccgca cttccgcgat gaaaggctaa gggttaaagt      1860
tccaatatca ggtgtgctct ccatcatgct aggaataaat aaagcgccag aggctttcga      1920
ctggtataac attctgaaat ttgctgattc aattagattg aaaaattatg cagaaatgga      1980
atcaatagaa atcataatgt ccaaagctat aattcgcaat gacattaaac cgtcaaggtc      2040
aaagaaggat tacataattc aaaatttaag accaccaaca aatgttgttg cagctatagc      2100
caaaatgccc tcagcgacat taacatcaat attgtctgat cggattcttg tcaatggggt      2160
tcggttaact cagtccttcg gagtaatcaa tagggtgatt gatgctatta gagttgcatt      2220
tgagaacgta ccgacagcag aacatggtat agctaagggt gctttgttat taccatatcc      2280
acgatcattc aacagatcat ctgcttacgt gcgtaaagat aatgttatat ataacgctcc      2340
gacagaggta cagaggttta atatatctga tttattggag ggaagatttt tcaaggact       2400 aataggccaa gtacaacgca tgtctccatt tgtcataaat ggtccattac aagtgcgtaa      2460
tcttgacgtg acggcgattg aatcggtaac ttcaggatac ttgacgatgt catctccata      2520
cgatgcatgt gttcggccag aagatctaag gcataataaa atagtttcac cacctacagt      2580
agaccattat agcgattcaa acattcagag gccgaacaca caatttgaac agctgctgtc      2640
aaaaacatca gtcttcatca ttgatgcgcc aaaaatcgcc gtacagcaag attcgaccgt      2700
ttacgcattc cagtataggg acatacaaat caacacatcc gtagtggata agttggaatt      2760
tacttcagtt aaacctcctg atgtgacgct cttcaatgga ttgcttgtgt ttgaggatta      2820
gatcagatat acagacacta aaaaccctga tatggataag ttggaattta cttcagttaa      2880
acctccaga                                                              2889
```

```
<210> SEQ ID NO 195
<211> LENGTH: 2340
<212> TYPE: DNA
<213> ORGANISM: Equine rotavirus

<400> SEQUENCE: 195
atgtcgaagc tcattgagtt ttctgacctg ggcatcgagg tcacaaaccg tgagcagctg        60
ttcaaaatat caaacaatac atcctcatac gaaacaatta gaccaagcaa agatatagaa       120
gattacatca gagaaagctc tcactacgtg gtaattgata agagaagaaa tgaaccattt       180
gttgaagtat ttactcaatt gtttccttct tcaattgttt ataaccataa ggaaggttat       240
aagtctggtg gctgtagaca tcttcttaac aatgttttac atgttagtaa ctatatgcac       300
acttattgca acagtgatac tagaaatctc gctcctgatg gttggaccat tgacaaggct       360
gatggatttg atgatccaat tggtgactac attcttcgct caatggtgaa tgattgttca       420
atagagaata aagcgcagca caggaataaa ccaaacggag tttacccgaa actcctaaac       480
ataaatgaat attttgttaa aaccctaaaa aaaatgataa ctcccgttag taatgttgat       540
tttcaatcat atcattacct gaaccaaaga agacagatag gcacattagt tagaaataca       600
atattcgaac taatcgcaaa taataattgg aatgtcaatt atattggacc agaatttgag       660
tcatttagaa atatttgcga gttgctactg aatagaaatt atacagggaa aataagagtt       720
tttaccttca attcttctac acaacatgat tacaaaaagc aattgtcatc ttttcatcgt       780
gagaaagtgg actgggatta cgtgcacaga cacagattga aatttgaaaa cgcgttttgc       840
catttattct tgcatcatat aattaagagt aggtcttatt caataatcta tgttaacacg       900
ctttacaaca ttggaaactg gacagaagcg tatccatggc ttaacatacg cgtggtagac       960
```

-continued

```
catattcctg taattctaaa caactcagta gtttttggtt ttatgttatc gacgaaagtg      1020
tgttcgttct cagtgaatgt tgacagtgat aaagttgttt attcaccgaa accatacgat      1080
gatgagaaca atgtttggac cgtttcaata ctaggggaaa atataggtgt gccttcaaat      1140
gaaacagaaa agatagcagc aaagaaaaat ggactgccaa actacattta cggtgggatg      1200
aagtttgatg tcgaagcgct tgattttaac tatattacag ttggtctgta ttcactatca      1260
aatgtcataa actccccaga actaattaaa gctactttat cttatgatca catttttact      1320
tttccaacat attcggaggg tgattggaga ctcgagattg agaaaacgaa caaaattttc      1380
atcacaacgc agaagcaatt caaattcaat gattggataa ttgatgcgaa aaatctttct      1440
ctggaaatgg atactgaggt tgtctcagaa tctgtgttcc tgcagctcgg taaagatcgc      1500
gctttcatct cagaccgtta tcaacacatg gtcgcatttc gatttaaaca aaaaaactat      1560
tactcagaca aatatatgtc acatctggga ataagacaac catcaatttt caacagggac      1620
agatttctga cgtcacgtct atctgcgtac atcgacagac aattgacact taattcagat      1680
ttgtcttcaa tagagaaaaa ccactttca gggtttcag gacacttgat tgcagttgaa      1740 aaatatttc atgcactggc ttatacaatg tctccaatgc ggtgggctaa cagagcgtta      1800
tctgacgcaa tttacaaaaa aactgacagg tggaccaatg ctgttggtga acgccattcg      1860
attcaagact tcaggaatac gtatgcatat ttgggagaca gtatcaatcc aatatttcga      1920
tctaatctgg tgactaacaa atatgcggat aagccaactt actgtatcca attattaagt      1980
aagaaaaacc acatcacgct acagctcaca actacatcac cagatagagc tatgcctcaa      2040
ataattaaag cggttgaggg cactagattc aaatacttag ggaggaacag atttggaacg      2100
ttggatgttg cactgtatca aacagatggt atgacacaat atgaaattgt gaacattctg      2160
agaacaatgg acattccctg tcaacaaacg aggccataca taatgcatat gacgatcaaa      2220
gatcaaagtg acataccatc gacgatcgtt gctaattcga ataacgttaa agtcaaagaa      2280
attagatgct gagctgacat atgatccacg agactatcgt cgtctacggt aggtggggag      2340
```

```
<210> SEQ ID NO 196
<211> LENGTH: 2324
<212> TYPE: DNA
<213> ORGANISM: Equine rotavirus

<400> SEQUENCE: 196
```

```
ggtatttaat cactaggcat gatttcctat ctaagacgtg agtggcagtc ttatggggag        60
actgtgctgc agatatcgtt cgaagatgag gacgcagtgg cagcaagaaa cggttcagat       120
acaacttcag aaagagatgt accgaccaaa gcggacggga ggtactgcta taaagcagag       180
gtgaataaat caaattatac taccgaagtg cgcgggtttg cactggggga agcggatgaa       240
cgtgtaagtg cggagcaatt ccaggtttat agcggagagg tgactaatgg ttacacattc       300
ataaacggag atccaccatg tcaaacggta atacgtattt acttgaatgt aacaggtgaa       360
attacgatag acgggcagag tgttcaagga atatatttcg aggctacttc ctgcatcaga       420
acggataatg gttataacct gcatgcgtat agagatcgta gtgtggtacc aactgaggca       480
caatggaaat taataacgcg tgctttctca aaaaacggat gcaccggttt agacggaaat       540
ggtcagttgt cagcctcagt ttcaattaaa aatgaaaagg aatggtcgta tgatattagc       600
ggagagactg agttaaacat gtactcttgg tcagatttat gtcaacagtc acgaacaact       660
atgagtaatg cagaacagag ttctcgaata atcatatacg agcaggaaga tggattttgg       720
aaaatattga ctgaaacact atggatcaaa ttgaaaccat attttaaacc atacggcaca       780
```

```
atgggagggg cttttaagaa ttggctcgta gactcaggat ttgagaaata cgaatacagt     840
tatacgtaca cgagggatgg aaaagtggtc aacgcaacaa cagtgacata cccaaaaccg     900
acgggcaaag cgggaattaa ccaatcgtgg agaccggcga cagactacaa cggacagtac     960
gtctgcatgc aaccaggtga tatattttcg gtttggtatt ttgaagatag gtggcagata    1020
aatcaggcaa tatacgctaa aaatttccag tcagattcaa gagctgaagg cgagttagaa    1080
aacacgggag gtttgatatt tagaatgaat tatataccaa gtctagctgg aatcaggaat    1140
aaagcgggca aagttaaata caggtatata aatgggggct ttgcacaggt tgacgccgga    1200
tcttacactg gcatggcaat aatattaaat tttgagtgtt acggtcgaaa gttctatgct    1260
gattcaaaca actatccggt tgacaacact ttgaatccat atatatgtta cataggagac    1320
gactatacgg taggagggac gcactacaga aacggtgcat gctcaggcta cgctgctggc    1380
tatgatgaca caatattgga acatgatatg actatatcat atacggtaat gaaaccatca    1440
gatccagatt ttgttacagg gggagaaagc tacggacaga gtataacgtc gggactagaa    1500
gtgtcaatcc gcaacctaca agatcagata aactcgatat tagcggaact gaatatacag    1560
caagttacgt ctgcggtatt ttcagcggtt acgtcagttg gagacctacc aaatctattt    1620
tcgaatgtta ccaagatttt cagtaagacg aaggatgctt tagcgaaatt gaaaggaaga    1680
aaggtggcta aaacagaacc tgttaaagct acaatgatca tagacaaatc taacatcgat    1740
gtaccaaatg tgtctatagt taacaaaatg ccagaagaat acgaactggg ggtcatctat    1800
aattcaatgc gccaagcgag actgcaaagg gagggtaagc acgattttcc gacattcgca    1860
ctagcaactg agatgaaact gccgtacata caaaatacca atacactaac tcctaaattc    1920
aaaaaatatt tgagtgatag aggtttactg tgtgatgaca ccgcagctat tcaatttgat    1980
cctatggatc taacgttttc aacattacga aagagaaacg cggacgttct gaagtataag    2040
attgatccgg agatagcaca tgaagtgctc tcagagatgt cgacaacagc cacaagatca    2100
ctgttttcac tgaatgtgag gaaacagata agtacgaata atgaatttgg atctccgaca    2160
tatgaacaga taatcaacag aatcctcgat gatagagaaa ttcttgacat tatggggaaa    2220
ttgaacaggc aaaccgtagg gaacttattc caagaatttt tagatagaac gaaagacatg    2280
ctgtccaact atgtctaaag gaatgagcca gtggtgaatg taat                    2324
```

```
<210> SEQ ID NO 197
<211> LENGTH: 1252
<212> TYPE: DNA
<213> ORGANISM: Equine rotavirus

<400> SEQUENCE: 197
accatctgtg caagtctggg aaacctatgg gaagcagcca gtccagcttg caatctcagg      60
tacatagcac caatatccat tctcaacact cgagcataca cttgcaaggc acctcaaccg     120
ctaatttcac aacacaacac attatttttaa cagtaggcgc cgtcttgata gcactacttc     180
tgacatctct cgtttttcagc tgtatctgca attgctacct ctactctaaa ctacgaaatg     240
gatttcaaac agtttctcaa cacgtcggga ggaaagaaag atctcatacc aacataccag     300
gacaacaaat tcgaccagac atgtacgtct aagaaaccgt ggaaaacgga aaaactcatg     360
tacccgtcct ccattcgtga aacaccattt gtggcaggtg aatccatatt gattgaggac     420
gtatgtcctt ttaatcatga acatttttgt ggcgccattc acattccaac acagagcaat     480
atgaaaccaa aagggaggac ttcgcatgtg acggctgata aaattgcatg gccatgtggt     540
```

-continued

```
atagaatcaa tcagtgtgga cggaaaagtg atctctggat ccgaatttgt caaatgcaga      600
tgtggcaacc tatatccaac aattattaac gaagttacag acttcttcat tctgacatgt      660
tgctcacatg acacaaaatc aatccaactg tgtgtgtctg aacgttatga ctgtgccaat      720 tgtgaaaga aggtgcgttg gtatacttca ggaaaaggca ttctcactaa acacaaattt      780
tacctgccgt caaagatttg cccttcatgt tcacctttca gagatttgat ttccacaatg      840
tctatgctta ataaagttga gttcattggt ccagacttca ggaagatgca agaaaactat      900
caatggaaac atgcgttgga aaatgaatgt gaacaggcat tcagggcttt gaattcacca      960
catattctga gtaagatttc aatcatctcc aagattaatc catcacttaa tgttaacacc      1020
atgaccgagg tggtaagttc atttaacaga gaatggccat ataacattgt catgacgcca      1080
atctccagag gcaaagttgc aattactaat aattactcca ggacaattat aactttcaat      1140
aataatgcgg aattgttcag atcagttaac atgctttgt tcaaatggcg gcttgcttga      1200
acatagaatg agagttccag atctctaacc ggacgcagtt gatcactata at             1252
```

<210> SEQ ID NO 198
<211> LENGTH: 1221
<212> TYPE: DNA
<213> ORGANISM: Equine rotavirus

<400> SEQUENCE: 198

```
gtgtacgagc atggatctga tcgaaacggt gaacgcttgc gtcagattgc agaaaagagt       60
attatcacta gctccaaaca caaacttgaa cactgcaggt cagtcaattc tcaatgatta      120
taatgctata gcatccagag tgaatgggaa gacttatgct cttttggacc aaacagcaat      180
attatcccct tacacgatac acgcaccgat aatttcgctg gccgttagaa tatctactga      240
tgattatgat gacatgagaa atggagttga gtctatacta gattgtttgg ctgcggcgat      300
tcgcactgaa ggctcgagac cggttagagt gattgaacgt agagttattg aaccagtggt      360
aaagcagctg gtcgaagatc tgaagttaaa aagtctgatt tctgaaatct caattgccaa      420
tttcgctgct actgataccg cgcttatcca accagaagta gtagaaactg aaaatccatt      480
gatagttggt atcatagaac aggtggttgt aagacaacca gccagtctaa atggtggcaa      540
tattagagca gcgattggca gatggtcagg taataaaggc tcagtcacat gtgtctcagg      600
catggaagca gaacatatgt tcttcgtgga actaaaagct aggacgtgtg gtgtactgaa      660
cgtcgtttat ctgccagccc caggagttat aatggtgcct atgccgcaag gacgcaacag      720
agaaagtgtt atacttgacg tatccgcaga gatgacagca gatgatttta taatcgattt      780
ctttgatgat aacaacattg tccatacgga aagaggagtt ggcctatttt catttccaat      840
gtgtaccaga attagattta gagttacacc atggacacaa caaaaatctc agaatggact      900
tgacactcca tcattggcta cgtgggcgaa cggtacgtct ccgaggcagc cagcggtgtc      960
tttcatgttt gaattaagaa gaaccttcac tgaaaacgat tataaattcg tttcacgatg      1020
tacctcgaaa gttcaataca tattggagac caacttccca gagacatcat ttattaacag      1080
gcctcaaata gaatggaacg tacaagagat gattacttct gacacagaca cagtatggtc      1140
acgtaaaatc gcaatgctag tcgcagcatt tgctgctaag atctgattct ccctgagccc      1200
gggagccggg ttgctctaga g                                               1221
```

<210> SEQ ID NO 199
<211> LENGTH: 1007
<212> TYPE: DNA
<213> ORGANISM: Equine rotavirus -continued

<400> SEQUENCE: 199

```
gttcagagcc atagtgttcg tttcagaagc tgctcgcagt gagaaactta cactatggct      60
ctgaacgctg ttgcgtcaat tctaggatct gtgttgtcta aacatgaaat tgatgatcag     120
ttgaaaatca ttgaagattt cattcatgca atgaaggatt gtggtatgat gctggacaat     180
tggcgcgatg catactacaa actgaggatt ccaaaacaaa tgactggtac aacaatggct     240
atacagttga aaacatgga aactgaagtg ctgaggttga gacatgaatc ttggaaaaat     300
ggtgaaacga tgaaagatag actgctgcaa tcatttgatg ttggcaaaaa gaatggatat     360
actgtacttc taccgaaaac aagaaacgca gaagtggtcc tactaaactc tactgttgac     420
atgaaattaa acccatttcc ctctgatgta gttgatgatt tgatcaagaa aaattcggaa     480
ctcgaaaaca gcattaaaac aatacaagag gaaacaagcg caaaaataag atatcaagag     540
gaactaattg aggaaaggga cagaatcatg agcgaaatga atcagcagat tacaatgctg     600
aaaaagaaga ttacattcct acgtgagaat cacaaagaaa gacttgagtt gattaatcaa     660
caccatgagg aagagaaaaa aatttacaaa agagagatat ctgaactccg tctagagaac     720
gggacattga atttgaccat ctcaacgttg aacaaacaat ttgacaacat gtcacttgat     780
catatgaaag acatccaagt cttgattgaa catgtttctg atgttgaaga gcgttgtgca     840
aaattgtcca atgaaaatgt tgtacttagg gaagaacaag acgaacatat acgactgatc     900
aaaggactgg ctgacaaagc taatttacag gttgacattt cgtaaacaaa gatgactcaa     960
gtgagttgtt actagacgcg acgtccgttc agagatatga gattggc                  1007
```

<210> SEQ ID NO 200
<211> LENGTH: 961
<212> TYPE: DNA
<213> ORGANISM: Equine rotavirus

<400> SEQUENCE: 200

```
tgagagggtc acccatcccc tggtcgccat gacgcagtct atttcgatcg cagatttcat      60
cgtgaaaact gaagatggtt ttatgccttc agatagagaa aatattgtgt tagatcgcta     120
cttgtctaaa gaactaaaag aactaagaga taaatataaa gatgagaaga atgatagagc     180
atcacttcgt attaaaatgt tttttgacgcc agcgccatca cgtcgcttca ctcaaagagg     240
agtagtgcca atgagagaac tcaaaactac gtctgatctc acaacttcaa tgttcaactt     300
gattactgac tggctactat ctgtgctcgc cgatgaagaa atggctgaat cttttgaaca     360
attcattgag agcaaatttc cagacatttt tgcttcagct gacaaattgg ccagatttgc     420
tcaaaggcta gaagataagc gcgacattat gcatagaaat ccatcaaagg ctttgaacgc     480
tttcggagca tgtttttggg cagtcaaacc gacatatgtc acggagggca agtgcaatgt     540
tgtgagagct accgacgatt ctattatact agaatttgag ccaattccgg aacatttgcg     600
atgtggaaga acaagatcaa ctttctataa actgtaccca ctgtcagaag aagctccggt     660
gacaggtatg atcgcattac gaggcgttgc aggtaatcaa tttctcatgt atcacgggca     720
cggacatatt agaacagttc cctatcatga aatgagtgac gcaatcaggt cttttgcaaa     780
gaaaaagagt gatgagctgg aagcgatagc gaagtcatca ctcgcggtcc actgtggtca     840
gaaattcatg aacatgcttg atcagattag atcaaaacag aaaatcgaag atatcataac     900
acaagccaaa cagaatgatc gaaagaaata gattgtgaca aatccaccat tgcgtttta     960 a                                                                    961
```

-continued

```
<210> SEQ ID NO 201
<211> LENGTH: 773
<212> TYPE: DNA
<213> ORGANISM: Equine rotavirus

<400> SEQUENCE: 201
gaaataatca gagatggcgt tgccattgct tctcgtcttt gctgcttgtg caaaagctca      60
attagtgatt actccaatca gcaacccgga gatttgtgtg ctgcacgcta gtgattggaa     120
tgtgaatagt ttcggagaca actttacaaa tattttttgaa acgtataatt cagtgactct     180
atccttttac cagtatgata gtacaaacta tgatgtgatt gatattatat ctaagagaga     240
ttattcgttg tgtcatatat tggcaataga cgttataagg ccagaaatgg atttcattac     300
gttccttcaa tcaaacaatg agtgttcgaa gtatgcagga cagaaaatac actatcaaaa     360
actctcaaca aacgaagaat ggtttgttta ttcaaagaat ttgaagtttt gtccactatc     420
tgacagtcta attggattgt attgcgatac gcagataaat ggtacatatt ttccattgtc     480
agagaatgag aaatacgatg ttacggatct accagaattt acagaatgg gttacgtttt     540 ttactcgaat gatgactttt acatttgtaa gcgcatcaat gaagacaaat gggtaaatta     600
tcatcttttc tacagagaat attcggcctc agggacggtg tcaagagcta tcagttggga     660
caatgtatgg acaggtttca agacatttgc gcaggttgta tataaaatac tagacatctt     720
tttcaacaat agaagaaact ttgagccacg agcataaaga agactaggcg aaa           773

<210> SEQ ID NO 202
<211> LENGTH: 697
<212> TYPE: DNA
<213> ORGANISM: Equine rotavirus

<400> SEQUENCE: 202
aatttcagcc atctttgaat atcaaagatg gctgaaatta atgaaagcat tagcaatgtg      60
ttaaatgttt tcgaaacact tcaacatgag acaatacata acgtgataaa gaacacggct     120
tcgtcaaaat tactaacgaa ttgtgcactg tcactactat cgatagtcac tgttgcattg     180
gcaaagaaca aagtcaaatt accgattaca aacaaaatac gtagtaatat caggcacatc     240
gctgaatcaa ttgtttggag agctgaaaca acaattagag aaatcgttaa tgatgttatt     300
tcaaagaatg acattttcaa agacattata catttaaccg aagaagttga aagaattaaa     360
caatctatat ccaaaattaa gggaatggac gtgactaagg aaatttttga cttatgtgaa     420
cgaaaaatga gagcaatcga tgataaaata gatgatgtgc agaaatcatg tgaaaggaga     480
attaaagatt atgactggaa aatcgctgca ttagcatcgc agaatttaaa atcagtagaa     540
gcgcatgtta gtatacagaa ccaaacagct gaggttatta atgatgatga gatgacaaaa     600
aataatattg ttagacaagc aagaacaaaa ttgaattcaa agcgacagct gtgagatggg     660
aacgtcgtag cgtatgatct gcgtgtgcga tgttccg                              697

<210> SEQ ID NO 203
<211> LENGTH: 764
<212> TYPE: DNA
<213> ORGANISM: Equine rotavirus

<400> SEQUENCE: 203
ggcagtggct ggaaacgctg cactgtccgc actctgccct gaaatgtctg aagcatctga      60
gtttaggttt ccaagtggaa ataggaaaag ggataaggta gcaaaacga gcaacaagaa     120 aatgccttct gattctacgt caactaaaag tgaaagtgaa acatcaagtc gtagcgacgc     180
```

-continued

```
agtgtcggta tactcagccg agactataaa ctctgaatac gaagaagcgt acaacaagtt      240
gagacgtgaa ccagttatag aagaaagtaa cgactcttgc tgtttggatg agtctttccc      300
agcaattgaa actgttaaaa aaacgaggcc gaaaagaatt actgaggtca gatacgacca      360
ttcggataac agcgatatac ttgaaaagtt gtctgagtta accttggaac ttgaaaagct      420
gaaaaccgca acgcaacctg ttggtgttga tgccgcgttt aatcagatat tacggaatgt      480
cgacaattta aatactaaac agaagcaagc actagtaaac gctattgtta attcaatgaa      540
ctaacttgat aatagatatg aacattcgta caacaacgac atacttaaga agctatctga      600
gttaactttg gaactttaga tgttgaaaac tgcaacgcaa cttgttagtg ctgacgccgc      660
gtttaattag atattgagga atgttaataa tttaaatgct aaatgaaagc aagcactagt      720
aaactatatt gttaattcaa tgaactaact taatcagatt gtgg                        764
```

```
<210> SEQ ID NO 204
<211> LENGTH: 18
<212> TYPE: DNA
<213> ORGANISM: Artificial
<220> FEATURE:
<223> OTHER INFORMATION: Forward primer for ERVB VP6

<400> SEQUENCE: 204
gcgcttatcc aaccagaa                                                      18
```

```
<210> SEQ ID NO 205
<211> LENGTH: 19
<212> TYPE: DNA
<213> ORGANISM: Artificial
<220> FEATURE:
<223> OTHER INFORMATION: Reverse primer for ERVB VP6

<400> SEQUENCE: 205
gccaatcgct gctctaata                                                     19
```

```
<210> SEQ ID NO 206
<211> LENGTH: 23
<212> TYPE: DNA
<213> ORGANISM: Artificial
<220> FEATURE:
<223> OTHER INFORMATION: Probe for ERVB VP6

<400> SEQUENCE: 206
accagccagt ctaaatggtg gca                                                23
```

```
<210> SEQ ID NO 207
<211> LENGTH: 21
<212> TYPE: DNA
<213> ORGANISM: Artificial
<220> FEATURE:
<223> OTHER INFORMATION: Forward primer for ERVB NSP3

<400> SEQUENCE: 207
gcaatgaagg attgtggtat g                                                  21
```

```
<210> SEQ ID NO 208
<211> LENGTH: 22
<212> TYPE: DNA
<213> ORGANISM: Artificial
<220> FEATURE:
<223> OTHER INFORMATION: Reverse primer for ERVB NSP3

<400> SEQUENCE: 208
```

-continued

```
ccattgttgt accagtcatt tg                                              22

<210> SEQ ID NO 209
<211> LENGTH: 22
<212> TYPE: DNA
<213> ORGANISM: Artificial
<220> FEATURE:
<223> OTHER INFORMATION: Probe for ERVB NSP3

<400> SEQUENCE: 209
ctggacaatt ggcgcgatgc at                                              22

<210> SEQ ID NO 210
<211> LENGTH: 20
<212> TYPE: DNA
<213> ORGANISM: Artificial
<220> FEATURE:
<223> OTHER INFORMATION: Forward primer for ERVB VP7

<400> SEQUENCE: 210
tcagttggga caatgtatgg                                                 20

<210> SEQ ID NO 211
<211> LENGTH: 18
<212> TYPE: DNA
<213> ORGANISM: Artificial
<220> FEATURE:
<223> OTHER INFORMATION: Reverse primer for ERVB VP7

<400> SEQUENCE: 211
tatgctcgtg gctcaaag                                                   18

<210> SEQ ID NO 212
<211> LENGTH: 25
<212> TYPE: DNA
<213> ORGANISM: Artificial
<220> FEATURE:
<223> OTHER INFORMATION: Probe for ERVB VP7

<400> SEQUENCE: 212
caggtttcaa gacatttgcg caggt                                           25
```

PCR METHOD FOR THE DETECTION OF EQUINE ROTAVIRUS GROUP B (ERVB) IN BIOLOGICAL SAMPLES

RELATED APPLICATIONS

This application claims priority from U.S. Provisional Application Ser. No. 63/196,152, filed Jun. 2, 2021, as well as U.S. Provisional Application Ser. No. 63/169,645, filed Apr. 1, 2021, the entire disclosures of which are incorporated herein by this reference.

SEQUENCE LISTING

The instant application contains a Sequence Listing which has been submitted in ASCII format via EFS-Web and is hereby incorporated by reference in its entirety. The ASCII copy of the Sequence Listing, which was created on Apr. 1, 2022, is named 13177N-2582US.txt and is 98.4 kilobytes in size.

TECHNICAL FIELD

The present disclosure is directed to Equine Rotavirus Group B and methods for diagnosing the same. In particular, the disclosure is directed to primers and probes for a newly discovered sequence of Equine Rotavirus Group B, as well as a method for detecting the rotavirus using the primers and probes.

BACKGROUND

Rotaviruses (RVs) belong to the Reoviridae family that is further divided into two subfamilies: Sedoreovirinae and Spinareovirinae. The Sedoreovirinae subfamily has 6 genera with RVs as one of them. Rotavirus was originally identified in mice, and in vervet monkey, before its emergence in humans. RV is a double-stranded RNA virus with segmented genomes under positive polarity. The virus has 11 genome segments each coding for at least one protein. RV genome codes for 6 structural proteins (VP) and 6 non-structural proteins (NSP). Specifically, segments 1, 2, 3, and 4 code for VP1, VP2, VP3, and VP4, respectively. VP4 is proteolytically cleaved into VP5* and VP8* during viral replication. Segments 6 and 9 express VP6 and VP7. Segment 5 encodes NSP1, while segments 7, 8, and 10 code for NSP3, NSP2, and NSP4. Segment 11 has two open reading frames that express NSP5 and NSP6, respectively. The total genome size is approximately 18.5 kb with individual genome segment sizes ranging from 667 to 3302 nucleotides in length.

The RV genus has 10 species also called groups/serogroups designated as A-J. These group demarcations are based on the nucleotide sequence of the inner capsid protein VP6. Rotaviruses from groups A, B, C can infect humans and animals, while D, E, F, G predominantly infect animals. Group A rotaviruses (RVA) are of clinical importance as they are a leading cause of acute severe gastroenteritis and life-threatening diarrhea in infants and children worldwide, although group B and C also infect humans. RVs are also a health concern for elderly and immunocompromised adult populations, in spite of the disease that is often less severe.

Globally, RVs are the primary cause of death due to diarrhea in children under the age of five. Based on the serological assay and two outer capsid protein sequences, two major serotypes of RVA are identified, the G serotype (based on VP7 sequence) and the P serotype (based on VP4 sequence), which is the foundation of a dual classification system that has been utilized for internationally serotyping RVs. For P serotypes, cross-reactivity among serotypes is often observed that has complicated the P serotype prediction, and thus for the sake of clarity, P genotype (based on VP4 sequence), rather than P serotype, is used commonly for classification. Currently, there are 35 G serotypes and 50 P genotypes. G1-G4 serotypes, P[8], P[4] are predominant G and P serotypes that are involved in more than 90% of all human RV infections. The complete genome sequence has been incorporated into the latest nomenclature of RVA. An established nucleotide percentage identity is used for each segment and new genotype is assigned if percentage identity of nucleotide sequence does not meet the established percentage. The Gx-P[x]-Ix-Rx-Cx-Mx-Ax-Nx-Tx-Ex-Hx designates VP7-VP4-VP6-VP1-VP2-VP3-NSP1-NSP2-NSP3-NSP4-NSP5/6 respectively in the nomenclature system. There are three major genomic constellations (Wa-like, DS-1 like, and AU-1 like) of RVA circulating in humans. These genomic constellations are based on the complete genome sequence similarities barring P and G genome sequences. The Wa-like constellation has a common ancestor with porcine RVA, while DS-1 like constellation has a common ancestor traced back to bovine RVA. These two are major RVA constellations circulating in humans. The less common AU-1 like constellation has a common ancestor to dogs and cats.

Recently, there has been a significant increase in foal diarrhea cases in central Kentucky, which has not been successfully diagnosed using available techniques. Accordingly, there remains a need for articles and methods to detect Rotavirus, specifically Rotavirus Group B.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

In some embodiments, the presently-disclosed subject matter is directed to a set of primers and probes for detecting rotavirus, the set including at least one forward primer selected from the group including SEQ ID NOS: 17, 20, 23, 26, 29, 32, 35, 38, 41, 44, 47, 50, 53, 56, 59, 62, 65, 68, 71, 74, 77, 80, 83, 86, 89, 92, 95, 98, 101, 104, 107, 110, 113, 116, 119, 122, 125, 128, 131, 134, 137, 140, 143, 146, 149, 152, 155, 158, 161, 164, 167, 204, 207, 210, and combinations thereof; at least one reverse primer selected from the group including SEQ ID NOS: 18, 21, 24, 27, 30, 33, 36, 39, 42, 45, 48, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153, 156, 159, 162, 165, 168, 205, 208, 211, and combinations thereof; and at least one probe selected from the group including SEQ ID NOS: 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151, 154, 157, 160, 163, 166, 169, 206, 209, 212, and combinations thereof.

In some embodiments, the at least one forward primer is selected from the group including SEQ ID NOS: 17, 20, 23, 26, 29, 32, 35, 38, 41, 44, 47, 50, 53, 56, 59, 62, and combinations thereof. In some embodiments, the at least one forward primer is selected from the group including SEQ ID NOS: 17, 23, 29, 35, 41, 47, 53, 59, and combinations thereof. In some embodiments, the at least one forward primer is selected from the group including SEQ ID NOS: 20, 26, 32, 38, 44, 50, 56, 62, and combinations thereof. In some embodiments, the at least one reverse primer is selected from the group including SEQ ID NOS: 18, 21, 24, 27, 30, 33, 36, 39, 42, 45, 48, 51, 54, 57, 60, 63, and combinations thereof. In some embodiments, the at least one reverse primer is selected from the group including SEQ ID NOS: 18, 24, 30, 36, 42, 48, 54, 60, and combinations thereof. In some embodiments, the at least one reverse primer is selected from the group including SEQ ID NOS: 21, 27, 33, 39, 45, 51, 57, 63, and combinations thereof. In some embodiments, the at least one probe is selected from the group including SEQ ID NOS: 19, 22, 25, 28, 31, 34, 37, 40, 43, 46, 49, 52, 55, 58, 61, 64, and combinations thereof. In some embodiments, the at least one probe is selected from the group including SEQ ID NOS: 19, 25, 31, 37, 43, 49, 55, 61, and combinations thereof. In some embodiments, the at least one probe is selected from the group including SEQ ID NOS: 22, 28, 34, 40, 46, 52, 58, 64, and combinations thereof.

In some embodiments, the at least one forward primer is selected from the group including SEQ ID NOS: 65, 68, 71, 74, 77, 80, 83, 86, 89, 92, 95, 98, 101, 104, 107, 110, 113, 116, 119, 122, 125, 128, 131, 134, 137, 140, 143, 146, 149, 152, 155, 158, 161, 164, 167, and combinations thereof. In some embodiments, the at least one reverse primer is selected from the group including SEQ ID NOS: 66, 69, 72, 75, 78, 81, 84, 87, 90, 93, 96, 99, 102, 105, 108, 111, 114, 117, 120, 123, 126, 129, 132, 135, 138, 141, 144, 147, 150, 153, 156, 159, 162, 165, 168, and combinations thereof. In some embodiments, the at least one probe is selected from the group including SEQ ID NOS: 67, 70, 73, 76, 79, 82, 85, 88, 91, 94, 97, 100, 103, 106, 109, 112, 115, 118, 121, 124, 127, 130, 133, 136, 139, 142, 145, 148, 151, 154, 157, 160, 163, 166, 169, and combinations thereof.

In some embodiments, the at least one forward primer is selected from the group including SEQ ID NOS: 204, 207, 210, and combinations thereof. In some embodiments, the at least one reverse primer is selected from the group including SEQ ID NOS: 205, 208, 211, and combinations thereof. In some embodiments, the at least one probe is selected from the group including SEQ ID NOS: 206, 209, 212, and combinations thereof.

In some embodiments, the at least one probe includes a reporter, quencher, or combination thereof attached thereto. In some embodiments, the rotavirus is equine rotavirus B. In some embodiments, the primers and probes are specific to a segment of the rotavirus selected from the group consisting of segments 1, 2, 3, 4, 5, 6, 7, 8, 9, 10, and 11.

Also provided herein, in some embodiments, is a method for detecting rotavirus, the method including extracting viral ribonucleic acid (RNA) from a sample; quantifying the viral RNA through polymerase chain reaction (PCR); and determining whether the sample is rotavirus positive based upon the quantification of the viral RNA; where the quantifying step includes the set of primers and probes according to one or more of the embodiments disclosed herein.

Further features and advantages of the presently-disclosed subject matter will become evident to those of ordinary skill in the art after a study of the description, figures, and non-limiting examples in this document.

DEFINITIONS

Figure 1:
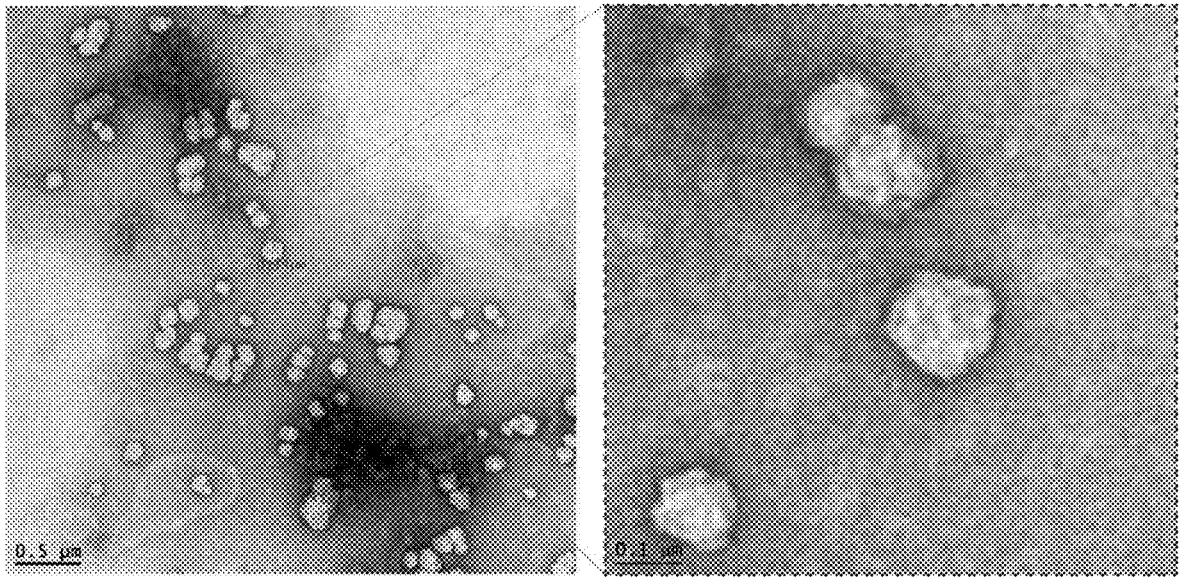
FIG. 1 shows images illustrating transmission electron microscope (TEM) examination of diarrhea samples from two diseased foals revealing single and clusters of round particles (~0.1 μm ø) with electron-dense "surface holes" characteristic of rotavirus particles.

Unless defined otherwise, all technical and scientific terms used herein have the same meaning as commonly understood by one of ordinary skill in the art to which the disclosure belongs. Any methods and materials similar to or equivalent to those described herein can be used in the practice or testing of the present disclosure, including the methods and materials are described below.

Following long-standing patent law convention, the terms "a," "an," and "the" refer to "one or more" when used in this application, including the claims. Thus, for example, reference to "a cell" includes a plurality of cells, and so forth.

The terms "comprising," "including," and "having" are intended to be inclusive and mean that there may be additional elements other than the listed elements.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration, percentage, or the like is meant to encompass variations of in some embodiments ±50%, in some embodiments ±40%, in some embodiments ±30%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

All combinations of method or process steps as used herein can be performed in any order, unless otherwise specified or clearly implied to the contrary by the context in which the referenced combination is made.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E1Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used herein, the terms "optional" or "optionally" means that the subsequently described event or circumstance can or cannot occur, and that the description includes instances where said event or circumstance occurs and instances where it does not.

As used herein, the term "patient" refers to a subject afflicted with a disease or disorder. A patient includes human and veterinary subjects.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. It is also contemplated that, in certain aspects, unless expressly indicated to the contrary, individual substituents can be further optionally substituted (i.e., further substituted or unsubstituted).

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

DETAILED DESCRIPTION

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Provided herein are articles and methods for detecting Rotavirus (RV). In some embodiments, the method includes detecting Rotavirus Group B (RVB), Equine Rotavirus (ERV), and/or Equine Rotavirus Group B (ERVB) in a sample. In some embodiments, the method includes detecting RV through a polymerase chain reaction (PCR) test such as, but not limited to, real-time quantitative PCR (qRT-PCR). For example, in some embodiments, the method includes extracting viral RNA from a sample, detecting and/or quantifying the viral RNA using qRT-PCR, and determining whether the sample is RV positive based upon the detection and/or quantification of the viral RNA.

The viral RNA may be extracted from any suitable sample, such as, but not limited to, fecal samples and/or fecal swabs. For example, in one embodiment, extracting the viral RNA from a bulk fecal sample includes i) preparing a clarified fecal suspension in a solution, such as phosphate-buffered saline (PBS), by centrifuging (e.g., 5,000 rpm for 5 min); ii) selecting a suitable amount of the clarified fecal suspension for viral RNA extraction (e.g., 200 µl); iii) extracting the viral RNA according to the PureLink Viral RNA/DNA mini kit (or other suitable kit) protocol for RNA extraction; and iv) eluting the extracted RNA in elution buffer or nuclease free water. In another embodiment, extracting the viral RNA from fecal and/or rectal swabs includes i) resuspending dry swabs in serum-free DMEM media, briefly vortexing, and centrifuging (e.g., 2000 rpm for 5 min); ii) selecting a suitable amount of the supernatant for viral RNA extraction (e.g., 200 μl); iii) extracting the viral RNA according to kit protocol (e.g., PureLink Viral RNA/DNA mini kit) for RNA extraction; and iv) eluting the extracted viral RNA in elution buffer or nuclease free water.

After extraction, the viral RNA may be detected and/or quantified using any suitable PCR, such as, but not limited to, one-step qRT-PCR or two-step RT-PCR (cDNA preparation and qPCR). For example, in one embodiment, detection and/or quantification with qRT-PCR includes setting up a one-step RT-PCR mixture and then running the mixture in the PCR system. In some embodiments, the one-step RT-PCR mixture includes RNA template; a forward primer, a reverse primer, and a probe (Tables 1 and 2); TaqMan fast virus 1 step Master Mix; and nuclease free water for desired volume. In some embodiments, the thermal cycling conditions include 55° C. for 30 minutes (Reverse transcription step); 95° C. for 10 minutes (Polymerase activation step); and 40 cycles at 95° C. for 15 seconds and 60° C. for 1 minute. In another embodiment, detection and/or quantification with two-step RT-PCR includes preparing cDNA from the extracted viral RNA; setting up a reaction mixture; and running the mixture in the PCR system. In some embodiments, preparing the cDNA includes breaking the dsRNA by incubating RNA with dnTPs and Random hexamers at elevated temperatures (e.g., 95° C. for 5 minutes) and then incubating at decreased temperatures (e.g., on ice for 2 min); adding other reagents after denaturation step; and incubating for 10 minutes at 25° C., 120 minutes at 37° C., and 85° C. for 5 minutes. In some embodiments, the reaction mixture includes undiluted cDNA; forward primer, reverse primer, and probe (Tables 1 and 2); TaqMan Universal PCR Master Mix; and nuclease free water for desired volume. In some embodiments, the thermal cycling conditions for the two-step RT-PCR include 50° C. for 2 minutes; 95° C. for 10 minutes; 40 cycle of 95° C. for 15 seconds and 60° C. for 1 minute. In some embodiments, following PCR, samples with Ct values less than 36 will be considered as a positive.

TABLE 1

Sequences of Primers and Probes Targeting 8 Segments of RV

| Segment | Assay Set | Related Sequence | S.No | I.D.* | Primer/Probe (5'-3') | SEQ ID NO: |
|---|---|---|---|---|---|---|
| 1 | 1 | SEQ ID NO: 1 | ERV1 | VP1-UT01-F | CGTGAATGTTACTCGGAAGG | 17 |
| | | | ERV2 | VP1-UT01-R | CAAGCTGCATGTATTACTTTGG | 18 |
| | | | ERV3 | VP1-UT01-P | TGGATAGGAAATGGTCGCACACCA | 19 |
| | 2 | SEQ ID NO: 2 | ERV4 | VP1-UT02-F | GTTAGATTTGGTGGAGGTAACG | 20 |
| | | | ERV5 | VP1-UT02-R | TGAGAGAAGAAGGAGGATGG | 21 |
| | | | ERV6 | VP1-UT02-P | ACGCTCATTGCGTCAAGCACGT | 22 |
| 2 | 1 | SEQ ID NO: 3 | ERV7 | VP2-UT03-F | CGACAGCAGAACATGGTATAG | 23 |
| | | | ERV8 | VP2-UT03-R | TACCTCTGTTGGAGCGTTA | 24 |
| | | | ERV9 | VP2-UT03-P | TGCCATACCCACGACCATTCAACA | 25 |
| | 2 | SEQ ID NO: 4 | ERV10 | VP2-UT04-F | CAAATGCGTTGGTTTGTCC | 26 |
| | | | ERV11 | VP2-UT04-R | ATGAAGAAACGATGCCTACG | 27 |
| | | | ERV12 | VP2-UT04-P | TGCGTTTGACGAACGTTGGCCT | 28 |
| 3 | 1 | SEQ ID NO: 5 | ERV13 | VP3-UT05-F | TGGCTTACACAATGTCTCC | 29 |
| | | | ERV14 | VP3-UT05-R | TGATACTGTCTCCCAAATATGC | 30 |
| | | | ERV15 | VP3-UT05-P | TGCGGTGGGCTAACAGAGCGTT | 31 |
| | 2 | SEQ ID NO: 6 | ERV16 | VP3-UT06-F | TCATCACAACGCAGAAGC | 32 |
| | | | ERV17 | VP3-UT06-R | ATAACGGTCTGAGATGAAAGC | 33 |
| | | | ERV18 | VP3-UT06-P | TCTGTGTTCCTGCAGCTCGGT | 34 |
| 4 | 1 | SEQ ID NO: 7 | ERV19 | VP4-UT07-F | ATCAGGAATAAAGCGGGTAAAG | 35 |
| | | | ERV20 | VP4-UT07-R | TCGACCGTAGCACTCAAA | 36 |
| | | | ERV21 | VP4-UT07-P | ACGCAGGATCTTACACTGGCATGG | 37 |
| | 2 | SEQ ID NO: 8 | ERV22 | VP4-UT08-F | CGAGCAGGAAGATGGATTT | 38 |
| | | | ERV23 | VP4-UT08-R | CTGAGTCTACGAGCCAATTC | 39 |
| | | | ERV24 | VP4-UT08-P | AAACCATACGGCACAATGGGAGGG | 40 |
| 6 | 1 | SEQ ID NO: 9 | ERV25 | VP6-UT09-F | ACTTGACACTCCATCATTGG | 41 |
| | | | ERV26 | VP6-UT09-R | CGAGGTACATCGTGAAACG | 42 |
| | | | ERV27 | VP6-UT09-P | AGGCAGCCAGCGGTGTCTTTCA | 43 |
| | 2 | SEQ ID NO: 10 | ERV28 | VP6-UT10-F | ACAGGCCTCAAATAGAATGG | 44 |
| | | | ERV29 | VP6-UT10-R | CAGGGAGAATCAGATCTTAGC | 45 |
| | | | ERV30 | VP6-UT10-P | AATCGCAATGCTAGTCGCAGCA | 46 |
| 5 | 1 | SEQ ID NO: 11 | ERV31 | NSP1-UT11-F | AGAAAGATCTCATACCAACATACC | 47 |
| | | | ERV32 | NSP1-UT11-R | TTCACCTGCCACAAATGG | 48 |
| | | | ERV33 | NSP1-UT11-P | TGTACCCGTCCTCCATTCGTGA | 49 |
| | 2 | SEQ ID NO: 12 | ERV34 | NSP1-UT12-F | AACTGTGTGTGTCTGAACG | 50 |
| | | | ERV35 | NSP1-UT12-R | TCTGAAAGGTGAACATGAAGG | 51 |
| | | | ERV36 | NSP1-UT12-P | TGTGGAAAGAAGGTGCGTTGGT | 52 |
| 8 | 1 | SEQ ID NO: 13 | ERV37 | NSP2-UT13-F | GATGAGCTGGAAGCGATAG | 53 |
| | | | ERV38 | NSP2-UT13-R | TTCTGTTTGGCTTGTGTTATG | 54 |
| | | | ERV39 | NSP2-UT13-P | CAGTGGACCGCGAGTGATGACTTC | 55 |
| | 2 | SEQ ID NO: 14 | ERV40 | NSP2-UT14-F | AGAGCTACCGACGATTCT | 56 |
| | | | ERV41 | NSP2-UT14-R | CTGACAGTGGGTACAGTTTAT | 57 |
| | | | ERV42 | NSP2-UT14-P | CCGGAACATTTGCGATGTGGAAGA | 58 |

TABLE 1-continued

Sequences of Primers and Probes Targeting 8 Segments of RV

| Segment | Assay Set | Related Sequence | S.No | I.D.* | Primer/Probe (5'-3') | SEQ ID NO: |
|---------|-----------|------------------|------|-------|----------------------|-----------|
| 7 | 1 | SEQ ID NO: 15 | ERV43 | NSP3-UT15-F | TCAACACTTCAGTCTCCATATT | 59 |
|  |  |  | ERV44 | NSP3-UT15-R | GCAATGAAAGATTGTGGTATGA | 60 |
|  |  |  | ERV45 | NSP3-UT15-P | TATGCATCGCGCCAATTGTCCAAC | 61 |
|  | 2 | SEQ ID NO: 16 | ERV46 | NSP3-UT16-F | CTGGCTGACAAAGCTAATTTAC | 62 |
|  |  |  | ERV47 | NSP3-UT16-R | GGTCAGCCAATCTCATATCTC | 63 |
|  |  |  | ERV48 | NSP3-UT16-P | AGTTGTTACTAGACGCGACGTCCG | 64 |

*F = Forward Primer; R = Reverse Primer; P = Probe

TABLE 2

Sequences of Primers and Probes for
Equine Rotavirus Group B

| Set Number | Type | Sequence | SEQ ID NO: |
|-----------|------|----------|-----------|
| 1 | Forward primer | AACAGGCATTCAGGGCTTTG | 65 |
|  | Reverse primer | CTTTGCCTCTGGAGATTGGC | 66 |
|  | Probe | TGAACTTACCACCTCGGTCATGGTGTT | 67 |
| 2 | Forward primer | GGCACCTCAACCGCTAATTT | 68 |
|  | Reverse primer | CTCCCGACGTGTTGAGAAAC | 69 |
|  | Probe | TGCTATCAAGACGGCGCCTACTGT | 70 |
| 3 | Forward primer | CTGTGCAAGTCTGGGAAACC | 71 |
|  | Reverse primer | TGCCTTGCAAGTGTATGCTC | 72 |
|  | Probe | AGCTGGACTGGCTGCTTCCCA | 73 |
| 4 | Forward primer | TCCGGTGACAGGTATGATCG | 74 |
|  | Reverse primer | ATCGCTTCCAGCTCATCACT | 75 |
|  | Probe | TCTCATGTATCACGGGCACGGACA | 76 |
| 5 | Forward primer | GTGCTCGCCGATGAAGAAAT | 77 |
|  | Reverse primer | GTCGCGCTTATCTTCTAGCC | 78 |
|  | Probe | TTTGCTTCAGCTGACAAATTGGCCAGA | 79 |
| 6 | Forward primer | AACGCTTTCGGAGCATGTTT | 80 |
|  | Reverse primer | AATCGTCGGTAGCTCTCACA | 81 |
|  | Probe | ACATTGCACTTGCCCTCCGTGACA | 82 |

TABLE 2-continued

Sequences of Primers and Probes for
Equine Rotavirus Group B

| Set Number | Type | Sequence | SEQ ID NO: |
|-----------|------|----------|-----------|
| 7 | Forward primer | CTGCTCGCAGTGAGAAACTT | 83 |
|  | Reverse primer | GTAGTATGCATCGCGCCAAT | 84 |
|  | Probe | ACGCAACAGCGTTCAGAGCCA | 85 |
| 8 | Forward primer | GATGTTGAAGAGCGTTGTGC | 86 |
|  | Reverse primer | GACGTCGCGTCTAGTAACAA | 87 |
|  | Probe | TGTCAGCCAGTCCTTTGATCAGTCGT | 88 |
| 9 | Forward primer | GAACGCTGTTGCGTCAATTC | 89 |
|  | Reverse primer | AGCCATTGTTGTACCAGTCA | 90 |
|  | Probe | TGCATCGCGCCAATTGTCCAGCA | 91 |
| 10 | Forward primer | TCAACACCATGAGGAAGAGAAA | 92 |
|  | Reverse primer | TTGCACAACGCTCTTCAACA | 93 |
|  | Probe | TCTGAACTCCGTCTAGAGAACGGGACA | 94 |
| 11 | Forward primer | GCTGCATTAGCATCGCAGAA | 95 |
|  | Reverse primer | CACGCGGATCATACGCTAC | 96 |
|  | Probe | ACGTTCCCATCTCACAGCTGTCGC | 97 |
| 12 | Forward primer | GCCCTGAAATGTCTGAAGCA | 98 |
|  | Reverse primer | TCGGCTGAGTATACCGACAC | 99 |
|  | Probe | TGCGTCGCTACGACTTGATGTTTCAC | 100 |

TABLE 2-continued

Sequences of Primers and Probes for
Equine Rotavirus Group B

| Set Number | Type | Sequence | SEQ ID NO: |
|---|---|---|---|
| 13 | Forward primer | TCGGTATACTCAGCC GAGAC | 101 |
| | Reverse primer | GCTGTTATCCGAATG GTCGT | 102 |
| | Probe | TGGTTCACGTCTCAA CTTGTTGTACGC | 103 |
| 14 | Forward primer | ACGACCATTCGGATA ACAGC | 104 |
| | Reverse primer | TCTGATTAAACGCGG CATCA | 105 |
| | Probe | ACCGCAACGCAACCT GTTGGT | 106 |
| 15 | Forward primer | GCTGCATTAGCATCG CAGAA | 107 |
| | Reverse primer | CGCAGATCATACGCT ACGAC | 108 |
| | Probe | TCCCATCTCACAGCT GTCGCTTTGA | 109 |
| 16 | Forward primer | CCAATGGGAACGCGT AATGT | 110 |
| | Reverse primer | CTTCAGCGAATGACC CTTGG | 111 |
| | Probe | CCAGCCCGTCAGACT AGAGGCA | 112 |
| 17 | Forward primer | TACCAAGACGTTACC GCTGA | 113 |
| | Reverse primer | CATTACGCGTTCCCA TTGGT | 114 |
| | Probe | TGCTCTCGCCAACTC GTCAAACGG | 115 |
| 18 | Forward primer | GCCAGCCAACATAAC ACACA | 116 |
| | Reverse primer | TGCCTCTTGTATCAC GCTCA | 117 |
| | Probe | AGGCTCCTGGTCTTT CGACCATCC | 118 |
| 19 | Forward primer | GGATGGTTTCGTTGC TACCC | 119 |
| | Reverse primer | CCACAATGGGCTGAA CTGAG | 120 |
| | Probe | CGCAGATGCACGTTC TCCAGTGC | 121 |
| 20 | Forward primer | GCCAAGTACAACGCA TGTCT | 122 |
| | Reverse primer | AGATCTTCTGGCCGA ACACA | 123 |
| | Probe | CGCCGTCACGTCAAG ATTACGCA | 124 |

TABLE 2-continued

Sequences of Primers and Probes for
Equine Rotavirus Group B

| Set Number | Type | Sequence | SEQ ID NO: |
|---|---|---|---|
| 21 | Forward primer | ACCGACAGCAGAACA TGGTA | 125 |
| | Reverse primer | AGACATGCGTTGTAC TTGGC | 126 |
| | Probe | ACCTCTGTACCTCTG TCGGAGCGT | 127 |
| 22 | Forward primer | TAAAGCGGTTGAGGG CACTA | 128 |
| | Reverse primer | ATGGCCTCGTTTGTT GACAG | 129 |
| | Probe | TCCAACGTTCCAAAT CTGTTCCTCCCT | 130 |
| 23 | Forward primer | GGGATTACGTGCACA GACAC | 131 |
| | Reverse primer | TGGTCTACCACGCGT ATGTT | 132 |
| | Probe | AGCCATGGATACGCT TCTGTCCAGT | 133 |
| 24 | Forward primer | TTCGGAGGGTGATTG GAGAC | 134 |
| | Reverse primer | TGAAAGCGCGATCTT TACCG | 135 |
| | Probe | TGTCTCAGAATCTGT GTTCCTGCAGCT | 136 |
| 25 | Forward primer | ACTTCCTGCATCAGA ACGGA | 137 |
| | Reverse primer | TGAGGCTGACAACTG ACCAT | 138 |
| | Probe | TCCGTCTAAACCGGT GCATCCGT | 139 |
| 26 | Forward primer | AGCGGAGAGGTGACT AATGG | 140 |
| | Reverse primer | TCCGTTCTGATGCAG GAAGT | 141 |
| | Probe | ACGGAGATCCACCAT GTCAAACGGT | 142 |
| 27 | Forward primer | GTTGACGCCGGATCT TACAC | 143 |
| | Reverse primer | TCATCATAGCCAGCA GCGTA | 144 |
| | Probe | TGCACCGTTTCTGTA GTGCGTCCC | 145 |
| 28 | Forward primer | GATACCGCGCTTATC CAACC | 146 |
| | Reverse primer | GTTCTGCTTCCATGC CTGAG | 147 |
| | Probe | ACCTGACCATCTGCC AATCGCTGC | 148 |

TABLE 2-continued

Sequences of Primers and Probes for
Equine Rotavirus Group B

| Set Number | Type | Sequence | SEQ ID NO: |
|---|---|---|---|
| 29 | Forward primer | ACACGATACACGCAC CGATA | 149 |
| | Reverse primer | CTTCGACCAGCTGCT TTACC | 150 |
| | Probe | AGTGCGAATCGCCGC AGCCA | 151 |
| 30 | Forward primer | CTCGAGACCGGTTAG AGTGA | 152 |
| | Reverse primer | TGGATAAGCGCGGTA TCAGT | 153 |
| | Probe | TCGACCAGCTGCTTT ACCACTGGT | 154 |
| 31 | Forward primer | GTTGCCATTGCTTCT CGTCT | 155 |
| | Reverse primer | TTCCAATCACTAGCG TGCAG | 156 |
| | Probe | TCCAATCAGCAACCC GGAGATTTGTGT | 157 |
| 32 | Forward primer | CTCAGGGACGGTGTC AAGAG | 158 |
| | Reverse primer | GCTCGTGGCTCAAAG TTTCT | 159 |
| | Probe | ACCTGCGCAAATGTC TTGAAACCTGT | 160 |
| 33 | Forward primer | AGCGCATCAATGAAG ACAAA | 161 |
| | Reverse primer | ACCTGCGCAAATGTC TTGAA | 162 |
| | Probe | TGACACCGTCCCTGA GGCCG | 163 |
| 34 | Forward primer | TCCGGTGACAGGTAT GATCG | 164 |
| | Reverse primer | ATCGCTTCCAGCTCA TCACT | 165 |
| | Probe | TCTCATGTATCACGG GCACGGACA | 166 |
| 35 | Forward primer | GCGGTTGAGGGCACT AGATTC | 167 |
| | Reverse primer | GCAACATCCAACGTT CCAAA | 168 |
| | Probe | AATACTTAGGGAGAA ACAG | 169 |

Also provided herein, in some embodiments, are primers and probes for detecting RV. In some embodiments, the primers and probes include any one or more primers and/or probes according to Table 1 and/or Table 2, which are shown as two sets of primers and probes targeting each of the 8 segments of the RV discussed herein. In some embodiments, different sets or combinations of primers and probes target different regions of the RV for diagnosis. In some embodiments, the probe includes any suitable reporter and/or quencher attached thereto. Suitable reporters include, but are not limited to, FAM, TET, JOE, Yakima Yellow, HEX, Cy3, Cy5, or any other suitable reporter. Suitable quenchers include, but are not limited to, MGBNFQ, BHQ, IBFQ, Eclipse or any other suitable quencher. For example, in one embodiment, the probe according to SEQ ID NO: 17 includes the reporter 6FAM attached to the 5' end and the quencher MGBNFQ attached to the 3' end (e.g., 6FAM-AAACCATACGGCACAATGGGAGGG-MGBNFQ). Segment sequence information and various features of the primers and probes of Table 1 are shown in Table 3.

TABLE 3

Segment Sequence Information and Features of Primers and Probes

| I.D. | Start | Length | Tm | Gc Percent | Amplicon (bp) |
|---|---|---|---|---|---|
| VP1-UT01-F | 693 | 20 | 60.221 | 50 | 122 |
| VP1-UT01-R | 814 | 22 | 60.103 | 40.909 | |
| VP1-UT01-P | 730 | 24 | 67.735 | 50 | |
| VP1-UT02-F | 1611 | 22 | 60.538 | 45.455 | 131 |
| VP1-UT02-R | 1741 | 20 | 60.054 | 50 | |
| VP1-UT02-P | 1666 | 22 | 68.611 | 54.545 | |
| VP2-UT03-F | 1954 | 21 | 59.985 | 47.619 | 119 |
| VP2-UT03-R | 2072 | 19 | 59.949 | 47.368 | |
| VP2-UT03-P | 1993 | 24 | 67.64 | 50 | |
| VP2-UT04-F | 1394 | 19 | 59.958 | 47.368 | 123 |
| VP2-UT04-R | 1516 | 20 | 60.019 | 45 | |
| VP2-UT04-P | 1415 | 22 | 68.635 | 54.545 | |
| VP3-UT05-F | 1028 | 19 | 59.287 | 47.368 | 150 |
| VP3-UT05-R | 1177 | 22 | 59.878 | 40.909 | |
| VP3-UT05-P | 1049 | 22 | 69.659 | 59.091 | |
| VP3-UT06-F | 1396 | 18 | 60.003 | 50 | 143 |
| VP3-UT06-R | 1538 | 21 | 59.892 | 42.857 | |
| VP3-UT06-P | 1488 | 21 | 67.189 | 57.143 | |
| VP4-UT07-F | 237 | 22 | 60.666 | 40.909 | 117 |
| VP4-UT07-R | 353 | 18 | 60.722 | 50 | |
| VP4-UT07-P | 298 | 24 | 67.996 | 54.167 | |
| VP4-UT08-F | 638 | 19 | 59.752 | 47.368 | 119 |
| VP4-UT08-R | 756 | 20 | 59.862 | 50 | |
| VP4-UT08-P | 705 | 24 | 68.408 | 54.167 | |
| VP6-UT09-F | 798 | 20 | 59.746 | 45 | 130 |
| VP6-UT09-R | 927 | 19 | 59.874 | 52.632 | |
| VP6-UT09-P | 844 | 22 | 69.786 | 59.091 | |
| VP6-UT10-F | 977 | 20 | 59.597 | 45 | 119 |
| VP6-UT10-R | 1095 | 21 | 59.295 | 47.619 | |
| VP6-UT10-P | 1047 | 22 | 66.455 | 50 | |
| NSP1-UT11-F | 188 | 24 | 60.117 | 37.5 | 128 |
| NSP1-UT11-R | 315 | 18 | 60.106 | 50 | |
| NSP1-UT11-P | 272 | 22 | 66.246 | 54.545 | |
| NSP1-UT12-F | 715 | 19 | 59.889 | 47.368 | 137 |
| NSP1-UT12-R | 851 | 21 | 60.064 | 42.857 | |
| NSP1-UT12-P | 750 | 22 | 66.186 | 50 | |
| NSP2-UT13-F | 833 | 19 | 59.633 | 52.632 | 125 |
| NSP2-UT13-R | 957 | 21 | 59.577 | 38.095 | |
| NSP2-UT13-P | 876 | 24 | 67.873 | 58.333 | |
| NSP2-UT14-F | 587 | 18 | 59.661 | 50 | 103 |
| NSP2-UT14-R | 689 | 21 | 59.577 | 42.857 | 689 |
| NSP2-UT14-P | 629 | 24 | 66.969 | 50 | |
| NSP3-UT15-F | 838 | 22 | 59.663 | 36.364 | 127 |
| NSP3-UT15-R | 964 | 22 | 59.632 | 36.364 | |
| NSP3-UT15-P | 918 | 24 | 67.671 | 50 | |
| NSP3-UT16-F | 923 | 22 | 59.903 | 40.909 | 106 |
| NSP3-UT16-R | 1028 | 21 | 59.918 | 47.619 | |
| NSP3-UT16-P | 980 | 24 | 67.193 | 54.167 | |

The presently-disclosed subject matter is further illustrated by the following specific but non-limiting examples. The following examples may include compilations of data that are representative of data gathered at various times during the course of development and experimentation related to the presently-disclosed subject matter. Those skilled in the art will recognize, or be able to ascertain, using no more than routine experimentation, numerous equivalents to the specific substances and procedures described herein.

EXAMPLES

Example 1—Rotavirus Non-Coding Regions

There are eleven separate segments comprising the ds RNA genome of rotavirus. Specifically, segments 1-10 each code for a single protein, while segment 11 encodes two proteins as it contains two initiation codons located in different open-reading-frames (ORFs). Each ORF has 5' and 3' untranslated regions (UTR). Table 4 summarizes 5' and 3' UTRs for all 11 segments of a group A rotavirus (RVA/Simian-tc/ZAF/SA11-H96/1958/G3P5B). Each positive sense strand has a 5' cap but lacks 3' poly (A) tail. The terminal non-coding ends of all the eleven segments are variable in the sequence but exhibit a good homology within the first 10 nucleotides at either end. However, the sequence conservation is relatively high among homologous segments of different rotavirus strains within the same group but is low between groups. Numerous studies demonstrated that the terminal ends of each segment harbor packaging signals, which are required for incorporation of the segmented genome into budding virions during virus replication. The lack of RGS and in vitro assays over the past few decades has hindered the progress to defining the packaging signals in Rotavirus.

TABLE 4

Summary of nucleotide sequence information for the untranslated 5' and 3' regions of simian Rotavirus SA11*

| Genome Segment | 5' UTR Sequence | SEQ ID NO: | 3' UTR Sequence | SEQ ID NO: |
|---|---|---|---|---|
| 1 | GGCUAU UAAAGC UGUACA | 170 | AACGCU UAGAUG UGACC | 171 |
| 2 | GGCUAU UAAAGG CUCA | 172 | ACGCCA ACCCCA UUGUGG AGAUAU GACC | 173 |
| 3 | GGCUUU UAAAGC AGUACC AGUAGU GUGUUU UACCUC UGAUGG UGUAAA C | 174 | GCUAAA AACUUA ACACAC UAGUCA UGAUGU GACC | 175 |
| 4 | GGCUAU AAA | 176 | GUAAUU UCUAGA GGAUGU GACC | 177 |
| 5 | GGCUUU UUUUUG AAAAGU CUUGUG UUAGCC | 178 | AAUUAC UAAUGU CACUAU CUAAUU AUACAG UAUUUA GCCAUC ACAAGA CCGUCC | 179 |

TABLE 4-continued

Summary of nucleotide sequence information for the untranslated 5' and 3' regions of simian Rotavirus SA11*

| Genome Segment | 5' UTR Sequence | SEQ ID NO: | 3' UTR Sequence | SEQ ID NO: |
|---|---|---|---|---|
| | | | AGACUA GAGUAG CGCCUA GCUGGC AAAAUA CUGUGA ACC | |
| 6 | GGCUUU UAAACG AAGUCU UCAAC | 180 | GGACCA AGCUAA CAACUU GGUAUC CAACUU UGGUGA GUAUGU AGCUAU AUCAAG CUGUUU GAACUC UGUAAG UAAGGA UACGUA UACGCA UUCGCU ACACAG AGUAAU CACUCA GAUGGU AUAGUG AGAGGA UGUGAC C | 181 |
| 7 | GGCAUU UAAUGC UUUUCA GUGGUU GAUGCU CAAG | 182 | CCAUUUU GAUACA UGUUGA ACAAUC AAAUAC AGUGUU AGUAUG UUGUCA UCUAUG CAUAAC CCUCUA UGAGCA CAAUAG UUAAAA GCUAAC ACUGUC AAAAAC CUAAAU GGCUAU AGGGGC GUUAUG UGGCC | 183 |
| 8 | GGCUUU UAAAGC GUCUCA GUCGCC GUUUGA GCCUUG CGGUGU AGCC | 184 | UUCGCU AUCAAU UUGAGG AUGAUG AUGGCU UAGCAA GAAUAG AAAGCG CUUAUG UGACC | 185 |
| 9 | GGCUUU AAAAGA GAGAAU UUCCGU UUGGCU | 186 | GUAUAA CUUAGG UUAGAA UUGUAU GAUGUG | 187 |

TABLE 4-continued

Summary of nucleotide sequence information
for the untranslated 5' and 3'
regions of simian Rotavirus SA11*

| Genome Segment | 5' UTR Sequence | SEQ ID NO: | 3' UTR Sequence | SEQ ID NO: |
|---|---|---|---|---|
| | AGCGGU UAGCUC CUUUUA | | ACC | |
| 10 | GGCUUU UAAAAG UUCUGU UCCGAG AGAGCG CGUGCG GAAAG | 188 | GAGGUU GAGCUG CCGUCG ACUGUC CUCGGA AGCGGC GGAGUU CUUUAC AGUAAG CACCAU CGGACC UGAUGG CUGACU GAGAAG CCACAG UCAGCC AUAUCG CGUGUG GCUCAA GCCUUA AUCCCG UUUAAC CAAUCC GGUCAG CACCGG ACGUUA AUGGAA GGAACG GUCUUA AUGUGA CC | 189 |
| 11 | GGCUUU UAAAGC GCUACA GUG | 190 | GUCUGA CCUGGG AACACA CUAGGG AGCUCC CCACUC CCGUUU UGUGAC C | 191 |

*Sequence was obtained from NCBI (NC011500-NC011510)

The 5' and 3' consensus sequences are mostly 5'-GGC (A/U)6-8-3' and 5'-UGUGACC-3' respectively. The 3' consensus sequence of groups A, C, D, F has either 5'-UGUGACC-3' or 5'-UGUGGCU-3', whereas its counterpart of groups B, G, H is 5'-AAAACCC-3', 5'-AAGACCC-3', or 5'-UAUACCC-3'. Interestingly, the 3' consensus sequence contains cis-acting signals necessary for viral replication. Mutagenesis studies of the 3' consensus sequence of rotavirus showed that CC nucleotides at the terminal end are essential for minus-strand synthesis initiation. The final four nucleotides GACC at the 3' end, termed as translation enhancer, have been shown to stimulate protein expression in the virus infected cells. RV exploits eukaryotic translational machinery to benefit its own replication. In eukaryotes, the mRNA has a 5' cap and 3' poly (A) tail and the translation is initiated by the interaction of the 5' and 3' ends after binding of poly (A) binding protein (PABP), which is followed by binding of eukaryotic translation initiation factor 4G (eIF4G). Recognition of 5' cap structure by eIF4G is essential for initiation of translation.

Intriguingly, RV RNA lacks a 3' poly(A) tail. Recent studies revealed that poly(A) tail and the associated function have been substituted by a tetra nucleotide motif at the 3' end, which acts as a translation initiator for RV protein synthesis. The N-terminal region of RV NSP3 (segment 7) binds to the tetra nucleotide motif at the 3' end. The C-terminal region of NSP3 has binding domains for the translation initiation factor eIF4G. Thus, binding of NSP3's N-terminal region to the 3' tetra nucleotide sequence together with the engagement of eIF4G with its C-terminal region facilitates the formation of circularized mRNA molecule, which as a result, triggers initiation of viral protein translation. These data highlight that the 3' terminal sequence of RG segmented RNA genome is essential for the translation of RV proteins.

The 5'terminal end starts with the GG dinucleotide that is present in all segments of the RV ds RNA genome regardless of RV group. Mutational analysis of the consensus sequence for 5' ends revealed that the GG dinucleotide motif acts as a recognition signal for RNA-dependent RNA polymerase (RdRp) and cofactors. This base-specific recognition leads to the formation of an initiation complex necessary for the minus strand synthesis. The UTRs at both 5' and 3' ends are believed to undergo the complementary base-pairing that drives the energy-dependent folding of positive-strand RNA into a high-order panhandle structure. In this panhandle structure, the 3' terminal sequence is either unpaired or partially base-paired, which makes the 3' terminus of positive-strand RNA accessible to RdRp for subsequent viral RNA genome synthesis. In the T7 polymerase promoter-driven cDNA expression system for RV segments, 5' UTR can have inhibitory effects on viral protein synthesis. For RV strains SA11, such effects were observed for genome segments 3, 5-6, and 7-11. The presence of inhibitory motif on 5' UTR of certain genome segments has a negative impact on the rescue efficiency of recombinant RVs. Further investigations showed that the inhibitory motif is present in a form of six nucleotide long pyrimidine rich motif (5'-GGY(U/A) UY-3') located at the 5' terminus. Introduction of nucleotide G upstream to 5' UTR and switching U to A at $5^{th}$ nucleotide abolished the inhibitory motif, which in turn promoted rescue of infectious RVs in a helper virus free RGS system.

Example 2—Rotavirus Replication

Infectious RV particle has a triple-layered capsid (TLP) lattice that encases a dsRNA genome containing 11 separate segments. The TLP consists of VP7, VP6, and VP2 respectively, which is arranged spatially from external to internal orientation. The outermost glycoprotein VP7 layer is embedded with spike protein VP4. RV infection and replication occur mostly in enterocytes especially at the tips of the villi. Rotavirus uses glycan receptors for attachment and entry into cells. This attachment is mediated by the receptor-binding domain of VP8* that derives from VP4 spike protein through the proteolytic cleavage either by trypsin or other exogenous proteases. In addition to VP8*, this cleavage event also gives rise to VP5. Initially, the sialoglycans were considered as receptors for human and animal RVs. Recent studies, however, show that RV primarily infecting animals use sialoglycans as receptors, while RV infecting humans instead utilize histo-blood group antigen (HBGA), a non-sialylated glycan for virus entry. It is interesting to note that various other coreceptors or cofactors for RV entry have been also proposed such as integrins, heat shock proteins, and tight junction proteins.

After initial attachment, VP4 undergoes conformational change whereby VP5, hidden underneath the receptor-binding domain of VP8*, is exposed. VP8* binds to glycan receptor while VP5* interacts with coreceptors like integrins and heat shock protein. In the light of the fact that stepwise blocking each of these receptors and coreceptors (one at a time) reduced viral titers but did not completely prevent RV entry and replication, it has been speculated that RV may utilize an elusive receptor that is more critical to its entry than previously characterized receptor/coreceptors. Alternatively, it can be envisioned that RV may utilize multiple pathways for cell entry, which warrants further investigation. Following receptor binding, RV can enter a cell for replication by either clathrin-dependent or clathrin-independent endocytosis. Most of the human and animal RVs use clathrin-dependent endocytic pathways while simian RV is shown to utilize clathrin-independent endocytosis. Interestingly, the clathrin-independent endocytosis used by simian RV is dependent on the presence of certain molecules on the cell surface such as dynamin and other small Rho GTPases. It has been suggested that critical amino acid residues or domains of VP8*, not the glycan receptor, dictates the type of endocytic pathway that will be utilized by the virus. Following endocytosis, RV virion reaches early endosomes, then late endosomes, and ultimately to mature endosomes. A low concentration of calcium in endosomes causes a complete loss of the outer layer of TLP, which as a result, leads to the formation of a double-layered particle (DLP) which is transcriptionally active.

To date, the mechanism of RV replication and particle assembly remains incompletely understood. RNA synthesis in RV occurs in subviral particles. VP1 (RdRp)-VP3 (RNA capping enzyme) complex are tethered to VP2 (core shell) at each 12 five-fold axes of the icosahedron. Since there is a polymerase complex (PC) needed for each segment synthesis, it is yet unknown as to how these segment-specific polymerase complexes interact with each other to initiate replication of multiple segments almost simultaneously. The PC gives rise to 5' capped positive-sense single-stranded RNA transcripts from the negative sense single-stranded RNA template. These nascent transcripts exit into the cytosol where they leverage host translational machinery for the synthesis of viral proteins. Viral protein NSP2 and NSP5 colocalize near DLP to form an inclusion body termed as viroplasm. A highly-packed supramolecular complex comprising of eleven positive-sense single-stranded RNA and VP2 is believed to drive the synthesis and replication of negative-strand RNA. Upon the completion of RNA genome replication, the nascent virions exit viroplasm and enter the endoplasmic reticulum (ER) where viral maturation takes place. This process can get facilitated by interactions between NSP4 and VP6. In ER, DLP transiently obtains its envelope, which is then removed following the acquisition of the major outer capsid proteins VP7 and VP4. The origin and function of transiently enveloped particles remain unknown. It is also unclear about the precise mechanism for the physical acquisition of VP4 protein. VP4 is thought to be retained as a heterotrimer (through interacting with VP7 and NSP4) nearby the viroplasm and ER membrane. The VP4 is then internalized in the lumen along with VP7, which catalyzes the viral assembly process that may concomitantly occur with the removal of transiently acquired envelope. Since VP4 has been found to interact with lipid raft after exiting from ER, it is also suggested that the final assembly involving VP4 and VP7 may take place after egressing from the ER. Historical evidence has suggested that RV particles were released by cell lysis, a method commonly deployed by non-enveloped viruses. Some earlier studies showed that RV could exit from both non-polarized and polarized cells, indicating that mature virions (TLPs) can get released from infected cells either by cell lysis (mostly observed in non-polarized cells) or by budding (observed in polarized epithelial cells). Nevertheless, recent work demonstrated that RV can bud from non-polarized cells without obvious cell lysis. Specifically, these studies revealed that RV hijacks the cellular actin network to promote infectious particle release. VP4 protein was found to interact with actin filaments of the brush border in intestinal epithelial cells, leading to the formation of actin bodies. The actin bodies were thought to remodel the apical membrane and induce membrane curvature, which subsequently drives the release of rotavirus particles from infected cells. Further study is needed to further clarify the RV egress pathway towards better understanding the molecular mechanism that drives the production of infectious RV particles.

Example 3—Equine Rotavirus Group B Virus'
Partial Sequences

Rotavirus information: RV is a double-stranded RNA virus with segmented genomes under positive polarity. The virus has 11 genome segments each coding for at least one protein. RV genome codes for 6 structural proteins (VP) and 6 non-structural proteins (NSP). Specifically, segments 1, 2, 3, and 4 code for VP1, VP2, VP3, and VP4, respectively. VP4 is proteolytically cleaved into VP5* and VP8* during viral replication. Segments 6 and 9 express VP6 and VP7. Segment 5 encodes NSP1, while segments 7, 8, and 10 code for NSP3, NSP2, and NSP4. Segment 11 has two open reading frames that express NSP5 and NSP6, respectively. The total genome size is approximately 18.5 kb with individual genome segment sizes ranging from 667 to 3302 nucleotides in length.

Below are the partial or nearly complete sequences of segments 1-8:

```
Segment 1 (VP1 gene)
(5' to 3' direction in cDNA sequence)
                              (SEQ ID NO: 1)
CATAATGATGGCCAGGCTGTCTCCACCCGAGACTC

AGTGAAATTGAACTCGCTGTGAAGATGCAGTGTAC

CCGCGGCAAGACGGAAAGACCCCGTGATATCTGCC

GGAGCTCTGCAGATATCAAGTCAATATATACAAAT

CCAAAAATTGCGAAAATAGTTTTTAAAGAAGCTGA

CAGACTGTGGGAATCGAAAACACTAAACTCACAGA

CACCCGATGAAGTGTTAGATGAAATAGAAAAATTG

AAGAAATCAACTGAAGATATCGATAGTAAACTGGA

AAAATTACTCAGGTTAAGGTATTTAACCGTGTATG

TAGACGATAAATCTGACAAAAGAAAAATAGTGTTG

AAACTGATCGATAATGTAGTGAATCTAACATCTAC

AGGTGACGTATTCCATTCAATCAGGGCTATAGAAT

TTCAAGCTAAACAGTGGAGGACGAAAAATGCGTCT

GTGCTGAAACCATACCATTACAACATACCAATTTG

TGAATACATTCGAGATAATGAAATTGAATACATAG

ATACTGGTGATTACAAATGGCAATCGGATACATTG
```

-continued

CAAGGTTTGATGCCAAATTATTATCACAGAACGCA

TACACTGATTGGTTCAGTTGTATTATCAGTTCTCA

AAAGAATTTCAACATATAGTGACGAGGAAAAGAAA

GCTTTGAACTACCTGTTCACAACCATACGTGAATG

TTACTCGGAAGGATACTTAGAATTGTCATTGGATA

GGAAATGGTCGCACACCATTTCACAATTAAAGGAA

GCCACGTTTAGACTGTATAACACCAAAGTAATACA

TGCAGCTTGTGCGATGGTTTCACTACTCCACGCAT

CAAACATAATGCCAGAATTCCTTTGCCAAATAATA

GCTGTATACAAAATAATTCCTGCAAATGCAGCAAA

ATTACTATCGTCGCCAATGACGTTGTACATAGGCA

TAGCAACTTTTCCATCTAAGATGGTAGCATCAACT

GGTAACGCCTCAGAATGTGCTTCAATGGACTTGCC

AAATAATGTCTTTGTCGCCAAAGAACAGATTGAAG

AATGGAATGTGGCATTCAAAGATGATCCTTTAAAT

GAGTCGCTGTTACTTATAGAAATGAATAAGAATCT

GAAGACTGATGTCGACACGTTCGTAAAAATATTTA

ACTGTTTTTCGGCGACTTTTCATGTTGGACATAGA

ATCGATAATGCACAGGACGCGATAGTTGATCAGGT

AACGGTTCAGTACACCACAGACGTAGATCGTGAAA

TGTATGATATGTATTATTACAAACTGAAAAGTATG

TTGAAGACTGAAATTAAAAAGTATGTTGAGGATCA

TATACATCGTGACTACCAAGACGTTACCGCTGAGT

CGTTATCTGCTCTCGCCAACTCGTCAAACGGATTT

CAGAAAGAGGTATTCTTTATCGACAGAAAATAAA

AACAATCAAGAAATATTGCATCTCGATGCAGATT

TGTTGGAAGGAGATTTCAGAGATGTGCGTAAAGTC

ATGTCTAGAGGTATACCCATGGGAACGCGTAATGT

TCCAGCCCGTCAGACTAGAGGCATATTCATCTTAC

CATGGCAAGTAGCAGCAGTTCAACACACAATAGCG

GAATCTTTATACAAAACAGCAAAAAAAGGAGCGTA

CCAAGGGTCATTCGCTGAAGCTTACACTTCAAAGA

CCGCATCATTAACATATGGAGTATTGGCTGAAGAT

ACTTCTAAGGCTATGAAAATAATTCTTTATACGGA

CGTGTCACAATGGGACGCCAGCCAACATAACACAC

AACCATACAGATCAGCATGGATAAATGCAATTAAA

GAGGTGAGAGAAGAGGAGGATGGTCGAAAGACCA

GGAGCCAACCATGTTAGGCATAAACGTGCTTGACG

CAATGAGCGTGATACAAGAGGCATTGCTAAATTCA

ACGTTAATCGTTACCTCCACCAAATCTAACAGAAA

CATACTAACAATCAGATATCACGGGGTCGCGTCAG

-continued

GAGAAAAAACAACGAAGGTTGGTAACTCATTCGCG

AACGTGGCGTTGATTGAAACTGTACTAGATGTCAC

AAAACAAAAGATACCAGACATCGAAGTGACTCATC

TGAGAGTGGATGGGGACGATAACGTCGTGTCGATC

AACACAGCATGCAATATATCAAAACTACAAACTGT

AATCAAATCCAACTATCAAAAGTTAAATGCACGAG

TTAAGGCGCTTGCTTCTTACACAGGTCTTGAAATG

GCGAAACGATTTATTATATGTGGAAACATCTTTGA

AAGAGGTGCTATACCAATTTTTACTGCTGAAAGGC

CATATGGCACGGACGTCTCAATACAATCTATGACT

GGTTCATCAATCTACTCATCTGCCGTGAACGCATA

TAGAGCGTTTGGTGATAAGTACTTAAGCTTTATGA

TGGACGTGTTGGTACCTCCATCATCAACAGTGAGA

CTGACTGGCAGATTACGAGTGTTGCTATCGCCAAT

TACACTGTTTGCGACTGGACCTTTAAGCTTTGAAG

TGACTCAAAATGGATTAGGAGGAAGATGTAGACTG

TATACACCAAATAGCCGACTGATGCAATTATTTAA

GATGCTGACAGACACTGTGTCTGTAGCGGTAACAC

CAGAAGAAGTAAAATTATATGCAAAGACAAATCAA

TTCAAGGAAAGAGTGTCTGTTATGGCAAATAGTCT

CAACGCAAAAATTAAAACAAATGCTCCAGCCCTAG

TTGCGATATTACGGGAGAAAGAAGAACAGAAAACG

TTGGGAGTGCCAAACGTGCAGACGCAGAAGAACAG

GAAGCAGGTAAATGAGGCATTGAAGATACTATCTG

TTCCAGAAAGAAATGATCTAATTCCAAAAGGCTAC

TACCCAGAAGAGCTGTACACCTTAGTGTTATCTAA

CTCAAAAATCACATATAAGGATTTTTTACCAGTGC

ACAGTATTTACCACACGAATAACCATGCCGTCGCG

TTACTTCATAATCAATTAGGGGTAACGATAAGCGA

GTCAAAACCAATAACTAAACCAGTTAACCACTTGT

ACGACATTGTAAGCACACTATCACCAATTTCTATA

TCACCAAGTGATATTTTAAAGCAATCAAAGAGATA

TGACTTGACATCATACAATGGAAAGAAAAGGTTCT

TAAGTGACTTGGGATTAACGGGGAACACCTTAAAA

ACATATCTCGCATCGAAGATGTTATTCAGAGATCT

TTTATTGGCTAAATATGATGAATTATACAGTACAC

CAGGTTTTGGTGCAACGCAACTGACAACAATACCG

TTGAATATACATTCAGCTGAGCAGGTTTTCAGTAT

AAATGTCAAGCTGCCACCTCATCTGTATGAAATAA

TGATGTTAATGTTGCTTTATGAGTACGTCCACTAT

-continued

GTGTTCATGACAAAAAGGACTTACACCGCTGTACT

ATCACCGATATCTGCAGAGCTCCGGCAGATATCAG

CGGTGTAAGTCCTTTT

Segment 2 (VP2 gene)
(5' to 3' direction in cDNA sequence)
                                    (SEQ ID NO: 3)
TAAGAACAACATTATCAAAGACCCTATTCATAGAT
GTAGACGCCGAAGAGTACTCGGTTTATGTTCCTCT

AGAAGTGCAAAACATTTCACCTGTGGTGATTGACA

TTAGACCAATACAGACATATAAACCAAAAACTTTA
ATGTACAAAGATACGGCGATAATACCTTCAAACAA

TGACTTGGTGTCAGATCAATGGGGAGCGGACGAAA

TCCTATATGATTCACACATGTTTAACGACATTAAC

ATAGGCCAGATTGAAGATTTTGAAACATATTTGTT

AGAGAAAGCTGTAGAGATTAAAGACTCGCTGCCAA

ATATCAACCATATATCACAATTAAGTAAAGACACG

AATCCTTTCAATGTACACAACACACTATGTTTAGA

TTTTGGACAAAAGGAGTATTATAATCTAATTTCAG

ACAGAACGAACCAGTCATTTGTGGGGAGAAGACAA

GCGGTACAATTTGATAACGTTGTTGTGGACGGGAT

TGAACGTACAGCGCGCATATCGTTGAGACTTCATC

CATTCGATAACCAAATGCTAAACTTAATACCACTG

AATTTAATACATGAGCAGCCCATTATTGATGTAAT

TAGAGAGTACCAGCTAGTAGCGGCGGATGGTTTCG

TTGCTACCCCAAAAATAAGGCTTGACAAGGATGTG

ACTATAATCGCAGATGCACGGTCTCCAGTGCTTGC
AAGATTATGTGAATTATCGCCTTATTTGCATCGAA

CAAGAATCTTAGATTCAATGACTCAGTTCAGCCCA

TTGTGGAAGGTTAACGTTTTTTCAAGTTCGATAGA
GAATGCTAAAGACTCCATTTATAAGATGGCTGAGA

TTTCATTCACTGTAGCCGACTCTGTTACCTCAGCG

CTGTCAACGGTCAATGTAGCCTCAGCGCAACAAAC
CCTAACTGTTTTACTTAATTCATGTATATTCCGTC

TTGAGGTTGATCCGACTGGAAGTCAGTCGAACTTT

GGTGCTGCAATATCGGCAGCGATAATGCTTGTTTT
GTTCCCAACTGATGAAGAAACGATGCCTACGAATG

TTTTTGATAATCTATGCAACTTAGTGTATAACGAA

TTGATAGCTTGGACGGTCGACAGACCAACGTTCGT

CAAACGCACGGGACAAACTAACGCATTTGAAGCTA

ATGTTAATATCGGTGGGGGTAATATGAATAGAGAC

ATATTGGCTTACATCAGGTTTATACTACTCAGAAG

GCCATGGATTTTGTATCAACGGACATACGACGAGG

-continued

CATATGCGGCTGATATATTCATTCCAAACATTGAC

GAAGCCAACATAAATGACCAAGCTTATGTGTAGCTGT

AAATAGTTTATTCTCAGGCCTGATCCAGGCAGCAC

AGAGGAATCCGAACCCAGGGAGGCAAATCAGTGCG

AATTCTTTTAGAAAATTGCTAAAATCAATGAAAGA

TGTGTGTTCAAACAAATTGATGCCAATAGTTAGAT

TAATCAGGTATAATATTGAAAGGATGGCGAGAGTT

TATAGGTGGTTTCCATATTCAGCCGACTTCGCAAA

TCGTATACCGCACTTCCGCGATGAAAGGCTAAGGG

TTAAGGTTCCAATATCAGGTGTGCTCTCCATCATG

CTAGGGATAAATAAAGCGCCAGAGGCCTTCGACTG

GTATAACATTCTGAAGTTTGCTGATTCAATTAGAT

TGAAAAATTATGCAGAAATGGAATCAATAGAAATC

ATAATGTCTAAAGCTATAATTCGCAATGACATTAA

ACCATCAAGGTCAAAGAAGGATTACATAATTCAAA

ATTTAAAACCACCAACAAATGTTGTTGCAGCTATA

GCCAAAATGCCCTCAGCTACATTAACATCAATATT

GTCTGATCGGATTCTTGTCAATGGGGTCCGGTTAA

CTCAGTCCTTCGGAGTAATCAATAGGGTGATTGAT

GCCATTAGAGTTGCATTTGAGAACGTACCGACAGC

AGAACATGGTATAGCTAAGGGTGCTTTGTTATTGC

CATACCCACGACCATTCAACAGATCATCTGCTTAC

GTGCGTAAAGATAATGTTATATATAACGCTCCAAC

AGAGGTACAGAGATTTAATATATCTGATTTATTGG

AGGGAAGATTTTATCAAGGACTAATAGGTCAAGAT

ATCTGCCGGAGCTCTGCAGATATCGTGGGTATGGC

AATAA

Segment 3 (VP3 gene)
(5' to 3' direction in cDNA sequence)
                                    (SEQ ID NO: 5)
AATTCTTCTACACAACATGATTACAAAAAGCAATT

GTCATCTTTTTATCGTGAGAAAGTGGACTGGGATT

ACGTGCATAGACACAGATTGAAATTTGAAAATGCG

TTTTGCCATTTATTCTTGCATCATATAATCAAGAG

TAGGTCTTATTCAATAATCTATGTTAACACGCTCT

ATAACATTGGAAATTGGACAGAAGCGTATCCATGG

CTTAACATACGCGTGGTGGACCATATTCCTGTCAT

TCTAAACAACTCAGTAGTTTTTGGTTTTATGTTAT

CAACGAACGTGTGTTCATTCTCAGTGAATGTTGAT

AGTGATAAAGTTGTTTATTCACCGAAACCATACGA

TGATGAAAACAATGTTTGGACCGTTTCAATACTAG

GGGAGAATATAGGTGTGCCTTCAAATGAAGCAGAA

-continued

AGGATAGCAGCAAAGAAAAATGGACTGCCAAACTA

CATTTACGGTGGGGTGAAGTTTGATGTCGAAGCGC

TTGATTTTAATTATATTACAGTTGGTCTGTATTCA

CTATCCAATGTCATAAACTCCCCAGAGCTAATCAA

AGCTACTTTATCTTATGATCACATTTTTACCTTTC

CAACATATTCAGAGGGTGATTGGAGACTCGAGATT

GAGAAAACAAACAAAATTTTCATTACAACGCAGAA

GCAATTCAAATTCAATGATTGGATAATTGATGCGA

AAAATCTTTCTCTGGAAATGGACACTGAGGTTGTC

TCAGAATCTGTTTTCCTGCAGCTTGGTAAAGATCG

CGCTTTCATCTCAGATCGTTATCAACACATGGTCG

CATTTCGATTTAAACAAAAAAACTATTACTCAGAC

AAATATATGTCACATCTGGGAATAAGACAACCATC

AATTTTCAACAGGGACAGATTTCTGACGTCACGTC

TATCTGCGTACATCGACAGACAATTGACACTCAAT

TCGGATTTGTCTTCAATAGAGAAAAACCACTTTTC

AGGGTTTTCAGGACACTTGATTGCAGTCGAAAAAT

ATTTTCATGCACTGGCTTACACAATGTCTCCAATG

CGGTGGGCTAACAGAGCGTTGTCTGACGCAATTTA

CAAAAAAACTGACAGGTGGACCAATGCTGTTGGTG

AGCGCCATTCGATTCAAGACTTTAGAAATACGTAT

GCATATTTGGGAGACAGTATCAATCCAATATTTCG

ATCCAATCTGGTGACTAACAAATATGCGGATAAGC

CAACTTACTGTATCCAATTATTAAGTAAGAAGAAC

CACATCACGCTACAACTCACAACTACATCACCGGA

TAGAGCCATGCCTCTAATAATTAAAGCGGTTGAGG

GCACTAGATTCAAATATTTAGGGAGAAACAAATTT

GGAACGATGGATGTTGCA

Segment 4 (VP4 gene)
(5' to 3' direction in cDNA sequence)
(SEQ ID NO: 7)
CCGACGGGCAAAGCGGGAATTAACCAATCATGGAG

ACCGGCAACAGACTACAACGGACAGTATGTCTGCA

TGCAACCAGGCGATATGTTTTCGGTTTGGTATTTT

GAAGATAGGTGGCAGATAAATCAGGCAATATACGC

TAAAAATTTCCAGTCAGATTCAAGAGCTGAAGGCG

AGTTAGAAAATACGGGAAGTTTGATATTTAGAATG

AATTATATACCAAGTCTAGCTGGAATCAGGAATAA

AGCGGGTAAAGTTAAATACAGGTATATAAATGGGG

GCTTTGCGCAGGTTGACGCAGGATCTTACACTGGC

ATGGCAATAATATTAAATTTTGAGTGCTACGGTCG

AAAATTTTATGCTGATTCAAACAACTATCCGGTTG

-continued

ACAACACTTTGAATCCATATATATGTTACATAGGA

GATGACTATACAGTAGGAGGGACGCACTACAGAAA

CGGTGCATGCTCAGGCTACGCTGCTGGCTATGATG

ACACAATATTGGAACATGATATGACTATATCATAT

ACGGTAATGAAACCATCAGATCCAGATTTTGTCAC

AGGGGGAGAAAGCTACGGACAGAGTATAACGTCGG

GACTAGAAGTGTCAGTCCGCAATCTACAAGATCAG

ATAAACTCAATATTAGCGGAACTGAATATACAGCA

AGTTACGTCTGCGGTGTTTTCAGCGGTTACGTCAG

TTGGAGACCTACCAAATCTATTTTCGAATGTTACC

AAGATTTTCAGTAAGACGAAGGACGCTTTAGCGAA

ATTGAAAGGAAGAAAGGTGGCTAAAACGGAACCTG

TTAAAGCTACAATGATTATAGATAAGTCTAACATC

GATGTGCCAAATGTATCTATAGTTAACAAAATGCC

AGAAGAATACGAACTGGGGGTCATCTATAATTCAA

TGCGCCAAGCGAGACTGCAAAGGGAGGGTAAGCAC

GATTTTCCGACATTCGCACTAGCAACCGAGATGAA

GTTGCCGTACATACAAAATACCAACACATTAACGC

CTAAATTCAAAAAATACTTGAGTGATAGAGGTTTG

CTGTGTGATGACACCGCAGCCGTTCAATTTGATCC

TATGGATCTAACGTTTTCAACACTACGAAAGAGAA

ACGCGGACATTCTGAAGTATAAGATTGATCCGGAG

ATAGCACATGAAGTGCTTTCAGAGATGTCGACAAC

AGCCACAAGATCACTGTTTTCACTGAATGTGAGGA

AACAGATAAGTACGAATAACGAATTTGGATCTCCG

ACATATGAACAGATAATCAACAGAATCCTCGATGA

TAGAGAAATTCTTGATATCATGGGGAAATTAAACA

GGCAAACCGTAGGGAACTTATTCCAAGAATTTTTA

GATAGAACGAAAGACATGCTGTCCAACTACGTCTA

AAGGAATGAGCGGCGGACGGGTGAGTAA

Segment 5 (NSP1 gene)
(5' to 3' direction in cDNA sequence)
(SEQ ID NO: 11)
ACTCGAGCATACACTTGCAGGGCACTTCAACCGCC

AATTTCACAACGCAACACATTATTTTAACAGTAGG

CGCTGTCTTGATAGCACTACTTTTAACATCTCTCA

TTTTCAGCTGTATTTGCAATTGTTATCTCTACTCT

AAACTACGAAATGGATTTCAAACAGTTTCTCAGCA

CGTCAGGAGGAAAGAAAGATCTCATACCAACATAC

CAGGGCAACAAATTCGACCAGACATGTATGTCTAA

GAAACCGTGGAAAACGGAAAAAACTCATGTACCCGT

CCTCCATTCGTGAAACACCATTTGTGGCAGGTGAA

-continued

TCCATATTGATTGAAGACGTATGTCCTTTTAATCA

TGAACACTTTTGTGGCGCCATTCACATTCCAACAC

AGAGCAATATGAAACCAAAAGGAAGGACTTCGCAT

GTGACGGCTGATAAAATTGCATGGCCATGTGGTAT

AGAATCAATCAGTGTGGACGGAAAAGTGATCTCTG

GATCCGAATTTGTCAAATGCAGATGTGGCAACCTA

TATCCAACAGTTATTAACGAAGTTACAGACTTCTT

CATTCTGACATGTTGCTCACATGACACGAAATCAA

TCCAACTGTGTGTGTCTGAACGTTATGACTGTGCC

AATTGTGGAAAGAAAGTGCGTTGGTATACTTCAGG

AAAAGGCATTCTCACTAAACACAAATTTTATCTGC

CATCTAAGATTTGCCCTTCATGTTCACCTTTCAGA

GATTTGATTTCCACAATGTCCATGCTTAATAAAGT

TGAGTTCATTGGTCCAGACTTCAGGAAGATGCAAG

ACAACTATCAATGGAAACATGCGCTGGAAAATGGA

TGTGAACAAGCATTCAGGGCCTTGAATTCACCACA

TATTCTGAGTAAGATTTCAATCATCTCTAAGATTA

ATCCATCACTTAATGTTAACACCGTGACCGAGGTG

ATAAGTTCATTTAACAGAGAATGGCCATATAACAT

TGTCATGACACCAATCTCTAGAGGCAAAGTTGCAA

TCACTAATAATTACTCTAGGACAATTATAACTTTC

AACAGTAACACGGAATTGTTCAGATCAGTTAACAT

GCTTTTGTTCAAATGGCGGCTTGCTTGAACATAGA

ATGAGAGTTCCAGATCTCTAACCGGACGCGATATC

TGCAGAGCTCCGGCAGATATCGTCAGCCAATCTCA

TATCTCTGAACGGACGTCGCGTCTAGTAACAACTC

ACTTGAGTCATCTTTGTTTACGAAATGTCAACCTG

TAAATTAGCTTTGTCAGCCAGTCCTTTGATCAGTC

GT

Segment 6 (VP6 gene)
(5' to 3' direction in cDNA sequence)
(SEQ ID NO: 9)

TTACGCCCAATAAATCCGGATAACGCTTGCACCCT

ACGTATTACCGCGGCTGCTGGCACGTAGTTAGCCG

GTGCTCTGCAGATATCCCCTTACACGATACACGCA

CCGATAATTTCGCTGGCCGTTAGAATATCTACTGA

TGATTATGATGACATGAGAAATGGAGTTGAGTCTA

TACTAGATTGTTTGGCTGCGGCGATTCGCACTGAA

GGCTCGAGACCGGTTAGAGTGATTGAACGTAGAGT

TATTGAACCAGTGGTAAAGCAGCTGGTCGAAGATC

TGAAGTTAAAAAGTCTGATTTCTGAAATCTCAATT

GCCAATTTCGCTGCTACTGATACCGCGCTTATCCA

-continued

ACCAGAAGTAGTAGAAACTGAAAATCCATTGATAG

TTGGTATCATAGAACAGGTGGTTGTAAGACAACCA

GCCAGTCTAAATGGTGGCAATATTAGAGCAGCGAT

TGGCAGATGGTCAGGTAATAAAGGCTCAGTCACAT

GTGTCTCAGGCATGGAAGCAGAACATATGTTCTTC

GTGGAACTAAAAGCTAGGACGTGTGGTGTACTGAA

CGTCGTTTATCTGCCAGCCCCAGGAGTTATAATGG

TGCCTATGCCGCAAGGACGCAACAGAGAAAGTGTT

ATACTTGACGTATCCGCAGAGATGACAGCAGATGA

TTTTATAATCGATTTCTTTGATGATAACAACATTG

TCCATACGGAAAGAGGGAGTTGGCCTATTTTCATTT

CCAATGTGTACCAGAATTAGATTTAGAGTTACACC

ATGGACACAACAAAAATCTCAGAATGGACTTGACA

CTCCATCATTGGCTACGTGGGCGAACGGTACGTCT

CCGAGGCAGCCAGCGGTGTCTTTCATGTTTGAATT

AAGAAGAACCTTCACTGAAAACGATTATAAATTCG

TTTCACGATGTACCTCGAAAGTTCAATACATATTG

GATACCAACTTCCCAGAGACATCATTTATTAACAG

GCCTCAAATAGAATGGAACGTACAAGAGATGATTA

CTTCTGACACAGACACAGTATGGTCACGTAAAATC

GCAATGCTAGTCGCAGCATTTGCTGCTAAGATCTG

ATTCTCCCTGAGCCCGGGAGCCGGGTTGCTCTAGA

GGATGAAAAAAATAGCACTAAAAACCCCCGGATAT

CTGCAGAG

Segment 7 (NSP3 gene)
(5' to 3' direction in cDNA sequence)
(SEQ ID NO: 191)

GATATCTGCTCGCAGTGAGAATCTTACACTATGGC

TCTGAACGCTGTTGCGTCAATTCTAGGATCTGTGT

TGTCTAAACATGAAATTGATGATCAGTTGAAAATC

ATTGAAGATTTCATTCATGCAATGAAAGATTGTGG

TATGATGTTGGACAATTGGCGCGATGCATACTACA

AACTGAGGATTCCAAAACCAATGACCGGTACAACA

ATGGCTATACAGTTGAAAAAATATGGAGACTGAAGT

GTTGAGGTTGAGACATGAATCTTGGAAGAATGGTG

AAACGATGAAAGACAGACTACTACAATCATTTGAT

GTTGGCAAGAAGAATGGATATACTGTACTTCTACC

GAAAACAAGAAACGCAGAAGTGGTTCTACTAAACT

CTACTGTTGACATGAAATTAAACCCATTTCCTTCT

GATGTAGTTGATGATTTGATTAAAAAAAAATTCGGA

ACTCGAAAACAGCATTAAAACAATACAGGAAGAAG

CAAACACAAAAATGAGATATCAAGAAGAGCTAATT

-continued
GAGGAAAGGGACAGAATCATGAGTGAAATGAACCA

ACAGATTATAATGCTGAGAAAGAAGATTACGTTCC

TACGTGAGAATCACAGAGAAAGACTTGAGTTGGTT

AATCAACACCATGAGGAAGAGAAAAAGATCTACAA

AAGAGAGATATCTGAACTCCGTCTAGAGAACGGGA

CATTGAATTTGACCATTTCAACGTTGAACAAGCAG

TTTGACAACATGTCACTTGATCATATGAAAGATAT

CCAAGTCTTAATTGAACATGTTTCTGATGTTGAAG

AGCGTTGTGCAAAGTTGTCCAGTGAGAATGTTGTA

CTTAGAGAAGAGCAAGATGAACATATACGACTGAT

CAAAGGACTGGCTGACAAAGCTAATTTACAGGTTG

ACATTTCGTAAACAAAATGACTCAAGTGAGTTGTT

ATTAGACGCGACGTCCGTTCAGAGATATGAGATTG

GCTGACCACCAATTAATAAAAACCTCATAAAGAAC

GTCGTAGTCCGGATTGGAGTCTGCAACTCGACTCC

ATGAAGTCGGAATCGCTAGTAATCGTGGATCAGA

Segment 8 (NSP2 gene)
(5' to 3' direction in cDNA sequence)
                         (SEQ ID NO: 13)
GGGTTCTTATCGGTACAAAAAAACGTAATAAGTGT

GTCGTGAGAGGGTCACCCATCCCCTGGTCGCCATG

ACGCAGTCTATTTCGATCGCAGATTTCATCGTGAA

AACTGAAGATGGTTTTATGCCTTCAGATAGAGAAA

ATATTGTGTTAGATCGCTACTTGTCTAAAGAACTA

AAAGAACTAAGAGATAAATATAAAGATGAGAAGAA

TGATAGAGCATCACTTCGTATTAAAATGTTTTTGA

CGCCAGCGCCATCACGTCGCTTCACTCAAAGAGGA

GTAGTGCCAATGAGAGAACTCAAAACTACGTCTGA

TCTCACAACTTCAATGTTCAACTTGATTACTGACT

GGCTACTATCTGTGCTCGCCGATGAAGAAATGGCT

GAATCTTTTGAACAATTCATTGAGAGCAAATTTCC

AGACATTTTTGCTTCAGCTGACAAATTGGCCAGAT

TTGCTCAAAGGCTAGAAGATAAGCGCGACATTATG

CATAGAAATCCATCAAAGGCTTTGAACGCTTTCGG

AGCATGTTTTTGGGCAGTCAAACCGACATATGTCA

CGGAGGGCAAGTGCAATGTTGTGAGAGCTACCGAC

GATTCTATTATACTAGAATTTGAGCCAATTCCGGA

ACATTTGCGATGTGGAAGAACAAGATCAACTTTCT

ATAAACTGTACCCACTGTCAGAAGAAGCTCCGGTG

ACAGGTATGATCGCATTACGAGGCGTTGCAGGTAA

TCAATTTCTCATGTATCACGGGCACGGACATATTA

GAACAGTTCCCTATCATGAAATGAGTGACGCAATC

-continued
AGGTCTTTTGCAAAGAAAAAGAGTGATGAGCTGGA

AGCGATAGCGAAGTCATCACTCGCGGTCCACTGTG

GTCAGAAATTCATGAACATGCTTGATCAGATTAGA

TCAAAACAGAAAATCGAAGATATCATAACACAAGC

CAAACAGAATGATCGAAAGAAATAGATTGTGACAA

ATCCACCATTGCGTTTTTAACCGATAAGAACCCCC

GATATCTGCAGA

Example 4—Probe Based qRT-PCR Protocol for Detection of Equine Rotavirus from Clinical Fecal Samples or Fecal Swabs Materials and Reagents:
  1×PBS (pH 7.2)
  PureLink Viral RNA/DNA mini kit (Cat:12280050)
Trizol LS
  TaqMan fast virus 1 step Master Mix (Cat: 4444434)
  Applied biosystem TaqMan Universal PCR mastermix (Cat: 4304437)
  Applied biosystem high capacity reverse transcription kit (Cat: 4368814)
  MicroAmp™ Fast Optical 96-Well Reaction Plate, 0.1 mL (Cat:4346907)
  Primers (working concentration of 10 μm)
  Probes (Working concentration of 10 μm)
  Nuclease free water
Instrument: Viia 7 or QuantStudio 6 or 7 Real-Time PCR System
Procedure:
1. Extract Viral RNA from Fecal Swab or Bulk Fecal Sample
  a) From Bulk Fecal Specimen
  I. Prepare clarified fecal suspension (10% w/v) in 1×PBS by centrifuging at 5,000 rpm for 5 min.
  II. Use 200 μl of clarified fecal suspension for RNA extraction.
  III. Follow PureLink Viral RNA/DNA mini kit protocol for RNA extraction. Note: Trizol LS can be used for viral RNA extraction. Start with a larger volume if using Trizol LS.
  IV. Elute in 50-60 μl of Elution buffer or Nuclease free water.
  b) From Fecal/Rectal Swabs
  I. Resuspend dry swabs in serum-free DMEM media. Vortex briefly, centrifuge at 2000 rpm for 5 min.
  II. Take 200 μl of supernatant for viral RNA extraction.
  III. Follow kit protocol for RNA extraction.
  IV. Elute in 50-60 μl of Elution buffer or Nuclease free water.
  2. The Viral RNA Extracted in Step 1 can be Directly Used for One Step RT PCR or can be Used for cDNA Preparation and qPCR.
  3. For One Step qRT-PCR
  Take 2-4 μl of RNA extracted in step 1 and setup One step RT-PCR mixture as follows: RNA template: 2-4 μl (denature at 95° C. for 5 minutes followed by 2 min incubation in ice to disrupt double strands of RV RNA before using as template); Forward Primer: 500 nM-800 nM (final concentration); Reverse Primer: 500 nM-800 nM (final Concentration); Probe: 250 nM-500 nM (final concentration); TaqMan fast virus 1 step Master Mix: Final concentration of 1×; Add nuclease free water to bring final mixture to desired volume. Thermal cycling conditions: 55° C. for 30 minutes (Reverse transcription step); 95° C. for 10 minutes (Polymerase activation step); and 40 cycles at 95° C. for 15 seconds and 60° C. for 1 minute.

4. For Two-Step RT-PCR

I. Prepare cDNA from RNA extracted in step 1. Make sure to break dsRNA by incubating RNA with dnTPs and Random hexamers at 95° C. for 5 min and incubating on ice for 2 min. Add other reagents after denaturation step. Incubate 10 min at 25° C., 120 min at 37° C. and 85° C. for 5 min.

II. Use 0.5-1 μl of undiluted cDNA in qPCR mixture.

III. Set up reaction mixture as following: Forward Primer: 500 nM-800 nM (final concentration); Reverse Primer: 500 nM-800 nM (final Concentration); Probe: 250 nM-500 nM (final concentration); TaqMan Universal PCR Master Mix: Final concentration of 1×; Add nuclease free water to bring final mixture to desired volume. Thermal cycling conditions: 50° C. for 2 minutes; 95° C. for 10 minutes; 40 cycle of 95° C. for 15 seconds and 60° C. for 1 minute. The RT-qPCR reactions will be performed in duplicates using Viia 7 or QuantStudio 7 Real-Time PCR Systems. Relevant controls (No template control (NTC), No RT control, positive control) will be included in every run.

5. Interpretation of the Results:

Samples with Ct values less than 36 will be considered as positive.

Example 5—RVB Gene Sequences

```
RVB/Horse-wt/USA/KY1518/2021 VP1 gene
                             (SEQ ID NO: 193)
AGAATTCAAGAGGAACCTATCTTACATCAAGTCAA

TATATACAAACCCCAAAATTGCGAAAATAGTTTTT

AAAGAAGCTGACAAACTGTGGGAATCGAAAACACT

AAACTCACAGACACCCGATGAAGTGTTAGATGAAA

TAGAAAAATTGAAGGAATCAACTGAAGATATCGAT

AGTAAACTGGAAAAATTACTAAGGTTAAGGTATTT

AACCGTGTATGTAGACGATAAATCTGACAAAAGAG

AAAATAGTGTTGAAACTGATCGATAATGTAGTGAAT

CTAACATCTACAGATGACGTATTCCATTCAATCAA

GGCTATAGAATTTCAAGCTAAACAGTGGAGGACGA

AAAATGCGTCCGTGCTGAAACCATACCATTACAAC

ATACCAATCTGTGAATACATTCGAGATAATGAAAT

TGAATACATAGATACTGGTGATTACAAATGGCAAT

CGGATACATTGCAAGGTTTAATGCCGAATTATTAT

CACAGAACGCATACACTAATTGGTTCAGTTGTATT

ATCAGTTCTCAAAAGAATTTCAACATATAGTGACG

AGGAAAAGAAAGCTTTGAACTACCTGTTTACAACC

ATACGCGAATGTTACTCGGAAGGATACTTAGAATT

GTCATTGGATAGGAAATGGTCACATACCATTTCAC

AATTAAAGGAAGCCACGTTTAGACTGTATAACACC

AAAGTAATACATGCAGCTTGTGCGATGGTTTCACT

ACTCCACGCATCAAACATAATGCCAGAATTCCTTT
```

```
GCCAAATAATAGCTGTATACAAAATAATTCCTGCA

AATGCAGCAAAATTACTATCGTCGCCAATGACGTT

GTACATAGGCATAGCAACTTTTCCATCTAAGATGG

TAGCATCAACTGGTAACGCCTCAGAATGTGCTTCA

ATGGACTTGCCAAATAATGTCTTTGTCGCCAAAGA

ACAGATTGAAGAATGGAATGTGGCATTCAAAGATG

ATCCTTTAAATGAGTCGCTGTTACTTATAGAAATG

AATAAGAACCTGAAGACTGATGTCGACACGTTCGT

AAAAATATTTAATTGTTTTTCGGCGACTTTTCATG

TTGGACATAGAATCGACAATGCACAGGACGCGATA

GTTGATCAGGTAACGGTTCAGTACACCACAGACGT

AGATCGTGAAATGTATGATATGTATTATTACAAAC

TGAAAAGTATGTTGAAGGCTGAAATTAAAAAATAT

GTTGAGGATCATATACATCGTGACTACCAAGACGT

TACCGCTGAGTCGTTATCTGCTCTCGCCAACTCGT

CAAACGGATTTCAGAAAGAGGTACTCTTTATCGAC

AGAAAAATAAAAACAACCAAGAAAATATTGCATCT

CGATGCAGATTTGTTAGAAGGAGATTTCAGAGATG

TGCGTAAAGTCATGTCTAGAGGTATACCAATGGGA

ACGCGTAATGTTCCAGCCCGTCAGACTAGAGGCAT

ATTCATCTTGCCATGGCAAGTAGCAGCAGTTCAAC

ACACAATAGCGGAATCTTTATACAAAACAGCCAAG

AAAGGAGCGTACCAAGGGTCATTCGCTGAAGCTTA

TACTTCAAAGACCGCGTCATTAACATATGGAGTAT

TGGCTGAAGATACTTCTAAGGCTATGAAGATAATT

CTTTATACAGACGTGTCACAATGGGACGCCAGCCA

ACATAACACACAACCATACAGATCAGCATGGATAA

ATGCAATTAAAGAGGTGAGAGAAGAAGGAGGATGG

TCGAAAGACCAGGAGCCTACTATGTTAGGCATAAA

CGTGCTTGACGCAATGAGCGTGATACAAGAGGCAT

TGCTAAATTCAACGTTAATCGTTACCTCCACCAAA

TCTAACAGAAACATACTAACAATCAGATATCACGG

GGTCGCGTCAGGAGAAAAAACAACGAAGGTTGGTA

ACTCATTCGCGAACGTGGCATTGATTGAAACTGTA

CTAGATGTCACAAAACAACAGATACCAGACATCGA

AGTGACTCATCTGAGAGTGGATGGGGATGACAACG

TCGTGTCGATCAACACAGCATGCAATATATCAAAA

CTACAAACTGTGATTAAATCCAACTATCAAAAGTT

AAATGCACGAGTTAAGGCGCTTGCGTCTTACACAG

GTCTTGAAATGGCGAAACGATTTATTATATGTGGA
```

-continued

```
AACATCTTTGAGAGAGGTGCTATACCAATTTTTAC

TGCTGAAAGACCATATGGCACGGACGTCTCAATAC

AATCTATGACTGGTTCATCAATCTACTCATCTGCC

GTGAACGCATATAGAGCGTTTGGTGATAAGTACTT

AAGCTTTATGATGGACGTGTTGGTACCTCCATCAT

CAACAGTGAGACTGACTGGCAGATTACGAGTGTTG

CTATCGCCAATTACGTTGTTTGCGACTGGACCTTT

AAGCTTTGAAGTGACTCAAAATGGATTAGGAGGAA

GATGTAGACTGTATACACCAAATAGCCGACTGATG

CAATTATTTAAGATGCTGACAGACACTGTATCCGT

GGCGGTAACACCAGAAGAAGTAAAATTATATGCAA

AGACAAATCAATTCAAGGAAAGAGTGTCTGTTATG

GCAAATAGTCTCAACGCAAAAATTAAAACAAATGC

TCCAGCCCTAATTGCGATATTACGAGAGAAAGAAG

AACAGAAAACATTGGGAGTGCCAAACGTGCAGACG

CAGAAGAACAGGAAGCAGGTGAATGAGGCATTGAA

GATACTATCTGTTCCAGAAAGAAATGATCTAATTC

CAAAAGGCTATTACCCAGAAGAGTTGTACACCTTA

GTGTTATCCAACTCGAAAATCACATATAAGGATTT

TTTACCAGTGCACAGTATTTACCACACGAATAACC

ATGCCGTCGCGTTACTTCATAATCAATTAGGAGTA

ACGATAAGCGAGTCAAAACCAATAACTAAACCAGT

TAACCACTTATACGACATTGTAGTCACACTATCAC

CAATTTCTATATCACCAAGTGATATTTTGAAGCAA

TCAAAGAGATATGACCTGACATCATACAATGGAAA

GAAAAGATTCTTAAGTGACTTGGGATTAACGGGGA

ACACCTTAAAAACATATCTCGCCTCGAAGATGTTA

TTCAGAGATCTTTTATTGGCTAAATATGATGAATT

ATACAGTACACCAGGTTTTGGTGCAACGCAACTGA

CAACAATACCGTTGAATATACATTCAGCTGAGCAG

GTTTTCAGTATAAATGTCAAGCTGCCACCTCATCT

GTATGAAATAATGATGTTAATGTTGCTTTATGAGT

ATGTCCACTATGTGTTCATGACAAAAAGAACTTAC

ACCGCTGTACTATCACCGATGTCGCAGGATCAATC

GGTTAAACTATCTAGTTTAATATTGAAAATGCTTG

ATAATATTAAACTTGATGTGGTGTCATTCTCTGAT

GACGCCTGGTAAACCATACATATAAAAACCCAGAT

CTG
```

RVB/Horse-wt/USA/KY1518/2021 VP2 gene
(SEQ ID NO: 194)

```
GGAAGATATGATGGGTGATTTAGATCTAATCACTT

CTGCTTCACAAGCAATACAAGCTACGAATGATAAA
```

-continued

```
AACGACAAACAAAAGATTTTTGATCAGTTGGTCAA

TGACTTGAAAAGACTGAGTAAGGGCGTCCTACAAC

CGGACGTCCAATCCAAACTATTGGAACTATCCAAT

ATAAATGGTCTAGTATTCAACGTAGAGGTACAAGA

AGATGTGGTTAACACGATCAATGACCAACCGGATC

CAACGTCTATATTCACACAAAACGTTTTCCAACTA

AGAACGACATTATCAAAGACTCTATTCATAGATGT

GGACGCCGAAGAGTATTCGGTTTACGTTCCTCTAG

AAGTGCAAAACATTTCACCTGTGGTGATTGACATT

AGACCAATACAAACATATAAACCAAAAACTTTAAT

GTACAAAGATACGGCGATAATACCTTCAAACAATG

ACTTGGTGTCAGATCAATGGGGAGCGGACGAAATC

CTATATGATTCGCACATGTTTAACGACATTAACAT

AGGCCAGATTGAAGATTTTGAAACGTATTTGTTAG

AGAAAGCTGTAGAAATTAAAGATTCGCTGCCAAAT

ATCAACCATATATCACAATTAAGCAAAGACACGAA

TCCTTTCAATGTGCACAACACACTATGTCTAGATT

TTGGACAAAAGGAGTATTATAATCTAATTTCAGAC

AGAACGAACCAGTCATTTGTGGGGAGAAGACAAGC

GGTACAATTTGATAACGTTGTTGTGGATGGGATTG

AACGTACAGCGCGCATATCGTTGAGACTTCATCCA

TTCGATAACCAAATGCTGAATTTAATACCCCTGAA

TTTAATACATGAGCAGCCCATTATTGATGTAATTA

GAGATTACCAGCTAGTAGCGGCGGATGGTTTCGTT

GCTACCCCAAAAGTAAGGCTCGACAAGGATGTGAC

TATAATCGCAGATGCACGTTCTCCAGTGCTTGCAA

GATTATGTGAATTATCGCCTTACTTGCATCGAACA

AGGATCTTAGATTCAATGACTCAGTTCAGCCCATT

GTGGAAGATTAACGTTTTTTCAAGTTCGATAGAGA

ATGCTAAAGACTCCATTTATAAGATGGCTGAGATT

TCATTCACTGTGGCCGACTCCGTTACCTCAGCGCT

GTCGACGGTTAATGTAGCCTCAGCGCAACAAACCC

TGACTGTTTTACTTAATTCATGTATATTCCGTCTT

GAGATTGATCCGACTGGAAGTCAGTCGAACTTTGG

TGCTGCAATATCGGCAGCGATAATGCTTGTTTTGT

TCCCAACTGATGAAGAAACGATGCCTACGAATGTT

TTTGATAATCTATGCAACTTAGTGTATAACGAATT

GATAGCTTGGACGGTCGACAGGCCAACGTTCGTCA

AACGCACGGGACAAACCAACGCATTTGAAGCTAAT

GTTAATATCGGTGGGGGTAATATGAATAGAGACAT
```

-continued

ATTAGCTTACATCAGGTTTATACTACTCAGAAGAC

CATGGATTTTGTATCAACGGACATACGACGAGGCA

TATGCGGCTGATATTTTCATTCCAAACATTGACGA

AGCCAACATAAATGACCAAGCTTATGTAGCTGTAA

ATAGTTTATTCTCAGGCCTGATCCAGGCAGCACAG

AGGAATCCGAACCCAGGGAGGCAAATCAGTGCGAA

TTCTTTTAGAAAATTGCTAAAATCAATGAAAGATG

TGTGTTCAAACAAATTGATGCCAATAGTTAGATTA

ATCAGGTATAATATTGAAAGGATGGCAAGAGTTTA

TAAGTGGTTTCCATATTCAGCCGACTTCGCAAATC

GTATACCGCACTTCCGCGATGAAAGGCTAAGGGTT

AAAGTTCCAATATCAGGTGTGCTCTCCATCATGCT

AGGAATAAATAAAGCGCCAGAGGCTTTCGACTGGT

ATAACATTCTGAAATTTGCTGATTCAATTAGATTG

AAAAATTATGCAGAAATGGAATCAATAGAAATCAT

AATGTCCAAAGCTATAATTCGCAATGACATTAAAC

CGTCAAGGTCAAAGAAGGATTACATAATTCAAAAT

TTAAGACCACCAACAAATGTTGTTGCAGCTATAGC

CAAAATGCCCTCAGCGACATTAACATCAATATTGT

CTGATCGGATTCTTGTCAATGGGGTTCGGTTAACT

CAGTCCTTCGGAGTAATCAATAGGGTGATTGATGC

TATTAGAGTTGCATTTGAGAACGTACCGACAGCAG

AACATGGTATAGCTAAGGGTGCTTTGTTATTACCA

TATCCACGATCATTCAACAGATCATCTGCTTACGT

GCGTAAAGATAATGTTATATATAACGCTCCGACAG

AGGTACAGAGGTTTAATATATCTGATTTATTGGAG

GGAAGATTTTATCAAGGACTAATAGGCCAAGTACA

ACGCATGTCTCCATTTGTCATAAATGGTCCATTAC

AAGTGCGTAATCTTGACGTGACGGCGATTGAATCG

GTAACTTCAGGATACTTGACGATGTCATCTCCATA

CGATGCATGTGTTCGGCCAGAAGATCTAAGGCATA

ATAAAATAGTTTCACCACCTACAGTAGACCATTAT

AGCGATTCAAACATTCAGAGGCCGAACACACAATT

TGAACAGCTGCTGTCAAAAACATCAGTCTTCATCA

TTGATGCGCCAAAAATCGCCGTACAGCAAGATTCG

ACCGTTTACGCATTCCAGTATAGGGACATACAAAT

CAACACATCCGTAGTGGATAAGTTGGAATTTACTT

CAGTTAAACCTCCTGATGTGACGCTCTTCAATGGA

TTGCTTGTGTTTGAGGATTAGATCAGATATACAGA

CACTAAAAACCCTGATATGGATAAGTTGGAATTTA

CTTCAGTTAAACCTCCAGA

-continued

RVB/Horse-wt/USA/KY1518/2021 VP3 gene (SEQ ID NO: 195)

ATGTCGAAGCTCATTGAGTTTTCTGACCTGGGCAT

CGAGGTCACAAACCGTGAGCAGCTGTTCAAAATAT

CAAACAATACATCCTCATACGAAACAATTAGACCA

AGCAAAGATATAGAAGATTACATCAGAGAAAGCTC

TCACTACGTGGTAATTGATAAGAGAAGAAATGAAC

CATTTGTTGAAGTATTTACTCAATTGTTTCCTTCT

TCAATTGTTTATAACCATAAGGAAGGTTATAAGTC

TGGTGGCTGTAGACATCTTCTTAACAATGTTTTAC

ATGTTAGTAACTATATGCACACTTATTGCAACAGT

GATACTAGAAATCTCGCTCCTGATGGTTGGACCAT

TGACAAGGCTGATGGATTTGATGATCCAATTGGTG

ACTACATTCTTCGCTCAATGGTGAATGATTGTTCA

ATAGAGAATAAAGCGCAGCACAGGAATAAACCAAA

CGGAGTTTACCCGAAACTCCTAAACATAAATGAAT

ATTTTGTTAAAACCCTAAAAAAAATGATAACTCCC

GTTAGTAATGTTGATTTTCAATCATATCATTACCT

GAACCAAAGAAGACAGATAGGCACATTAGTTAGAA

ATACAATATTCGAACTAATCGCAAATAATAATTGG

AATGTCAATTATATTGGACCAGAATTTGAGTCATT

TAGAAATATTTGCGAGTTGCTACTGAATAGAAATT

ATACAGGGAAAATAAGATTTTTTACCTTCAATTCT

TCTACACAACATGATTACAAAAAGCAATTGTCATC

TTTTCATCGTGAGAAAGTGGACTGGGATTACGTGC

ACAGACACAGATTGAAATTTGAAAACGCGTTTTGC

CATTTATTCTTGCATCATATAATTAAGAGTAGGTC

TTATTCAATAATCTATGTTAACACGCTTTACAACA

TTGGAAACTGGACAGAAGCGTATCCATGGCTTAAC

ATACGCGTGGTAGACCATATTCCTGTAATTCTAAA

CAACTCAGTAGTTTTTGGTTTTATGTTATCGACGA

AAGTGTGTTCGTTCTCAGTGAATGTTGACAGTGAT

AAAGTTGTTTATTCACCGAAACCATACGATGATGA

GAACAATGTTTGGACCGTTTCAATACTAGGGGAAA

ATATAGGTGTGCCTTCAAATGAAACAGAAAAGATA

GCAGCAAAGAAAAATGGACTGCCAAACTACATTTA

CGGTGGGATGAAGTTTGATGTCGAAGCGCTTGATT

TTAACTATATTACAGTTGGTCTGTATTCACTATCA

AATGTCATAAACTCCCCAGAACTAATTAAAGCTAC

TTTATCTTATGATCACATTTTTACTTTTCCAACAT

ATTCGGAGGGTGATTGGAGACTCGAGATTGAGAAA

-continued

ACGAACAAAATTTTCATCACAACGCAGAAGCAATT

CAAATTCAATGATTGGATAATTGATGCGAAAAATC

TTTCTCTGGAAATGGATACTGAGGTTGTCTCAGAA

TCTGTGTTCCTGCAGCTCGGTAAAGATCGCGCTTT

CATCTCAGACCGTTATCAACACATGGTCGCATTTC

GATTTAAACAAAAAAACTATTACTCAGACAAATAT

ATGTCACATCTGGGAATAAGACAACCATCAATTTT

CAACAGGGACAGATTTCTGACGTCACGTCTATCTG

CGTACATCGACAGACAATTGACACTTAATTCAGAT

TTGTCTTCAATAGAGAAAAACCACTTTTCAGGGTT

TTCAGGACACTTGATTGCAGTTGAAAAATATTTTC

ATGCACTGGCTTATACAATGTCTCCAATGCGGTGG

GCTAACAGAGCGTTATCTGACGCAATTTACAAAAA

AACTGACAGGTGGACCAATGCTGTTGGTGAACGCC

ATTCGATTCAAGACTTCAGGAATACGTATGCATAT

TTGGGAGACAGTATCAATCCAATATTTCGATCTAA

TCTGGTGACTAACAAATATGCGGATAAGCCAACTT

ACTGTATCCAATTATTAAGTAAGAAAAACCACATC

ACGCTACAGCTCACAACTACATCACCAGATAGAGC

TATGCCTCAAATAATTAAAGCGGTTGAGGGCACTA

GATTCAAATACTTAGGGAGGAACAGATTTGGAACG

TTGGATGTTGCACTGTATCAAACAGATGGTATGAC

ACAATATGAAATTGTGAACATTCTGAGAACAATGG

ACATTCCCTGTCAACAAACGAGGCCATACATAATG

CATATGACGATCAAAGATCAAAGTGACATACCATC

GACGATCGTTGCTAATTCGAATAACGTTAAAGTCA

AAGAAATTAGATGCTGAGCTGACATATGATCCACG

AGACTATCGTCGTCTACGGTAGGTGGGGAG

RVB/Horse-wt/USA/KY1518/2021 VP4 gene
(SEQ ID NO: 196)
GGTATTTAATCACTAGGCATGATTTCCTATCTAAG

ACGTGAGTGGCAGTCTTATGGGGAGACTGTGCTGC

AGATATCGTTCGAAGATGAGGACGCAGTGGCAGCA

AGAAACGGTTCAGATACAACTTCAGAAAGAGATGT

ACCGACCAAAGCGGACGGGAGGTACTGCTATAAAG

CAGAGGTGAATAAATCAAATTATACTACCGAAGTG

CGCGGGTTTGCACTGGGGGAAGCGGATGAACGTGT

AAGTGCGGAGCAATTCCAGGTTTATAGCGGAGAGG

TGACTAATGGTTACACATTCATAAACGGAGATCCA

CCATGTCAAACGGTAATACGTATTTACTTGAATGT

AACAGGTGAAATTACGATAGACGGGCAGAGTGTTC

AAGGAATATATTTCGAGGCTACTTCCTGCATCAGA

-continued

ACGGATAATGGTTATAACCTGCATGCGTATAGAGA

TCGTAGTGTGGTACCAACTGAGGCACAATGGAAAT

TAATAACGCGTGCTTTCTCAAAAAACGGATGCACC

GGTTTAGACGGAAATGGTCAGTTGTCAGCCTCAGT

TTCAATTAAAAATGAAAAGGAATGGTCGTATGATA

TTAGCGGAGAGACTGAGTTAAACATGTACTCTTGG

TCAGATTTATGTCAACAGTCACGAACAACTATGAG

TAATGCAGAACAGAGTTCTCGAATAATCATATACG

AGCAGGAAGATGGATTTTGGAAAATATTGACTGAA

ACACTATGGATCAAATTGAAACCATATTTTAAACC

ATACGGCACAATGGGAGGGGCTTTTAAGAATTGGC

TCGTAGACTCAGGATTTGAGAAATACGAATACAGT

TATACGTACACGAGGGATGGAAAAGTGGTCAACGC

AACAACAGTGACATACCCAAAACCGACGGGCAAAG

CGGGAATTAACCAATCGTGGAGACCGGCGACAGAC

TACAACGGACAGTACGTCTGCATGCAACCAGGTGA

TATATTTTCGGTTTGGTATTTTGAAGATAGGTGGC

AGATAAATCAGGCAATATACGCTAAAAATTTCCAG

TCAGATTCAAGAGCTGAAGGCGAGTTAGAAAACAC

GGGAGGTTTGATATTTAGAATGAATTATATACCAA

GTCTAGCTGGAATCAGGAATAAAGCGGGCAAAGTT

AAATACAGGTATATAAATGGGGGCTTTGCACAGGT

TGACGCCGGATCTTACACTGGCATGGCAATAATAT

TAAATTTTGAGTGTTACGGTCGAAAGTTCTATGCT

GATTCAAACAACTATCCGGTTGACAACACTTTGAA

TCCATATATATGTTACATAGGAGACGACTATACGG

TAGGAGGGACGCACTACAGAAACGGTGCATGCTCA

GGCTACGCTGCTGGCTATGATGACACAATATTGGA

ACATGATATGACTATATCATATACGGTAATGAAAC

CATCAGATCCAGATTTTGTTACAGGGGGAGAAAGC

TACGGACAGAGTATAACGTCGGGACTAGAAGTGTC

AATCCGCAACCTACAAGATCAGATAAACTCGATAT

TAGCGGAACTGAATATACAGCAAGTTACGTCTGCG

GTATTTTCAGCGGTTACGTCAGTTGGAGACCTACC

AAATCTATTTTCGAATGTTACCAAGATTTTCAGTA

AGACGAAGGATGCTTTAGCGAAATTGAAAGGAAGA

AAGGTGGCTAAAACAGAACCTGTTAAAGCTACAAT

GATCATAGACAAATCTAACATCGATGTACCAAATG

TGTCTATAGTTAACAAAATGCCAGAAGAATACGAA

CTGGGGGTCATCTATAATTCAATGCGCCAAGCGAG

-continued

ACTGCAAAGGGAGGGTAAGCACGATTTTCCGACAT

TCGCACTAGCAACTGAGATGAAACTGCCGTACATA

CAAAATACCAATACACTAACTCCTAAATTCAAAAA

ATATTTGAGTGATAGAGGTTTACTGTGTGATGACA

CCGCAGCTATTCAATTTGATCCTATGGATCTAACG

TTTTCAACATTACGAAAGAGAAACGCGGACGTTCT

GAAGTATAAGATTGATCCGGAGATAGCACATGAAG

TGCTCTCAGAGATGTCGACAACAGCCACAAGATCA

CTGTTTTCACTGAATGTGAGGAAACAGATAAGTAC

GAATAATGAATTTGGATCTCCGACATATGAACAGA

TAATCAACAGAATCCTCGATGATAGAGAAATTCTT

GACATTATGGGGAAATTGAACAGGCAAACCGTAGG

GAACTTATTCCAAGAATTTTTAGATAGAACGAAAG

ACATGCTGTCCAACTATGTCTAAAGGAATGAGCCA

GTGGTGAATGTAAT

RVB/Horse-wt/USA/KY1518/2021 NSP1 gene
                                (SEQ ID NO: 197)
ACCATCTGTGCAAGTCTGGGAAACCTATGGGAAGC

AGCCAGTCCAGCTTGCAATCTCAGGTACATAGCAC

CAATATCCATTCTCAACACTCGAGCATACACTTGC

AAGGCACCTCAACCGCTAATTTCACAACACAACAC

ATTATTTTAACAGTAGGCGCCGTCTTGATAGCACT

ACTTCTGACATCTCTCGTTTTCAGCTGTATCTGCA

ATTGCTACCTCTACTCTAAACTACGAAATGGATTT

CAAACAGTTTCTCAACACGTCGGGAGGAAAGAAAG

ATCTCATACCAACATACCAGGACAACAAATTCGAC

CAGACATGTACGTCTAAGAAACCGTGGAAAACGGA

AAAACTCATGTACCCGTCCTCCATTCGTGAAACAC

CATTTGTGGCAGGTGAATCCATATTGATTGAGGAC

GTATGTCCTTTTAATCATGAACATTTTTGTGGCGC

CATTCACATTCCAACACAGAGCAATATGAAACCAA

AAGGGAGGACTTCGCATGTGACGGCTGATAAAATT

GCATGGCCATGTGGTATAGAATCAATCAGTGTGGA

CGGAAAAGTGATCTCTGGATCCGAATTTGTCAAAT

GCAGATGTGGCAACCTATATCCAACAATTATTAAC

GAAGTTACAGACTTCTTCATTCTGACATGTTGCTC

ACATGACACAAAATCAATCCAACTGTGTGTGTCTG

AACGTTATGACTGTGCCAATTGTGGAAAGAAGGTG

CGTTGGTATACTTCAGGAAAAGGCATTCTCACTAA

ACACAAATTTTACCTGCCGTCAAAGATTTGCCCTT

CATGTTCACCTTTCAGAGATTTGATTTCCACAATG

TCTATGCTTAATAAAGTTGAGTTCATTGGTCCAGA

-continued

CTTCAGGAAGATGCAAGAAAACTATCAATGGAAAC

ATGCGTTGGAAAATGAATGTGAACAGGCATTCAGG

GCTTTGAATTCACCACATATTCTGAGTAAGATTTC

AATCATCTCCAAGATTAATCCATCACTTAATGTTA

ACACCATGACCGAGGTGGTAAGTTCATTTAACAGA

GAATGGCCATATAACATTGTCATGACGCCAATCTC

CAGAGGCAAAGTTGCAATTACTAATAATTACTCCA

GGACAATTATAACTTTCAATAATAATGCGGAATTG

TTCAGATCAGTTAACATGCTTTTGTTCAAATGGCG

GCTTGCTTGAACATAGAATGAGAGTTCCAGATCTC

TAACCGGACGCAGTTGATCACTATAAT

RVB/Horse-wt/USA/KY1518/2021 VP6 gene
                                (SEQ ID NO: 198)
GTGTACGAGCATGGATCTGATCGAAACGGTGAACG

CTTGCGTCAGATTGCAGAAAAGAGTATTATCACTA

GCTCCAAACACAAACTTGAACACTGCAGGTCAGTC

AATTCTCAATGATTATAATGCTATAGCATCCAGAG

TGAATGGGAAGACTTATGCTCTTTTGGACCAAACA

GCAATATTATCCCCTTACACGATACACGCACCGAT

AATTTCGCTGGCCGTTAGAATATCTACTGATGATT

ATGATGACATGAGAAATGGAGTTGAGTCTATACTA

GATTGTTTGGCTGCGGCGATTCGCACTGAAGGCTC

GAGACCGGTTAGAGTGATTGAACGTAGAGTTATTG

AACCAGTGGTAAAGCAGCTGGTCGAAGATCTGAAG

TTAAAAAGTCTGATTTCTGAAATCTCAATTGCCAA

TTTCGCTGCTACTGATACCGCGCTTATCCAACCAG

AAGTAGTAGAAACTGAAAATCCATTGATAGTTGGT

ATCATAGAACAGGTGGTTGTAAGCAACCAGCCAG

TCTAAATGGTGGCAATATTAGAGCAGCGATTGGCA

GATGGTCAGGTAATAAAGGCTCAGTCACATGTGTC

TCAGGCATGGAAGCAGAACATATGTTCTTCGTGGA

ACTAAAAGCTAGGACGTGTGGTGTACTGAACGTCG

TTTATCTGCCAGCCCCAGGAGTTATAATGGTGCCT

ATGCCGCAAGGACGCAACAGAGAAAGTGTTATACT

TGACGTATCCGCAGAGATGACAGCAGATGATTTTA

TAATCGATTTCTTTGATGATAACAACATTGTCCAT

ACGGAAAGAGGGAGTTGGCCTATTTTTCATTTCCAAT

GTGTACCAGAATTAGATTTAGAGTTACACCATGGA

CACAACAAAAATCTCAGAATGGACTTGACACTCCA

TCATTGGCTACGTGGGCGAACGGTACGTCTCCGAG

GCAGCCAGCGGTGTCTTTCATGTTTGAATTAAGAA

-continued

GAACCTTCACTGAAAACGATTATAAATTCGTTTCA

CGATGTACCTCGAAAGTTCAATACATATTGGAGAC

CAACTTCCCAGAGACATCATTTATTAACAGGCCTC

AAATAGAATGGAACGTACAAGAGATGATTACTTCT

GACACAGACACAGTATGGTCACGTAAAATCGCAAT

GCTAGTCGCAGCATTTGCTGCTAAGATCTGATTCT

CCCTGAGCCCGGGAGCCGGGTTGCTCTAGAG

RVB/Horse-wt/USA/KY1518/2021 NSP3 gene
                              (SEQ ID NO: 199)
GTTCAGAGCCATAGTGTTCGTTTCAGAAGCTGCTC

GCAGTGAGAAACTTACACTATGGCTCTGAACGCTG

TTGCGTCAATTCTAGGATCTGTGTTGTCTAAACAT

GAAATTGATGATCAGTTGAAAATCATTGAAGATTT

CATTCATGCAATGAAGGATTGTGGTATGATGCTGG

ACAATTGGCGCGATGCATACTACAAACTGAGGATT

CCAAAACAAATGACTGGTACAACAATGGCTATACA

GTTGAAAAACATGGAAACTGAAGTGCTGAGGTTGA

GACATGAATCTTGGAAAAATGGTGAAACGATGAAA

GATAGACTGCTGCAATCATTTGATGTTGGCAAAAA

GAATGGATATACTGTACTTCTACCGAAAACAAGAA

ACGCAGAAGTGGTCCTACTAAACTCTACTGTTGAC

ATGAAATTAAACCCATTTCCCTCTGATGTAGTTGA

TGATTTGATCAAGAAAAATTCGGAACTCGAAAACA

GCATTAAAACAATACAAGAGGAAACAAGCGCAAAA

ATAAGATATCAAGAGGAACTAATTGAGGAAAGGGA

CAGAATCATGAGCGAAATGAATCAGCAGATTACAA

TGCTGAAAAGAAGATTACATTCCTACGTGAGAAT

CACAAAGAAAGACTTGAGTTGATTAATCAACACCA

TGAGGAAGAGAAAAAAATTTACAAAAGAGAGATAT

CTGAACTCCGTCTAGAGAACGGGACATTGAATTTG

ACCATCTCAACGTTGAACAAACAATTTGACAACAT

GTCACTTGATCATATGAAAGACATCCAAGTCTTGA

TTGAACATGTTTCTGATGTTGAAGAGCGTTGTGCA

AAATTGTCCAATGAAAATGTTGTACTTAGGGAAGA

ACAAGACGAACATATACGACTGATCAAAGGACTGG

CTGACAAAGCTAATTTACAGGTTGACATTTCGTAA

ACAAAGATGACTCAAGTGAGTTGTTACTAGACGCG

ACGTCCGTTCAGAGATATGAGATTGGC

RVB/Horse-wt/USA/KY1518/2021 NSP2 gene
                              (SEQ ID NO: 200)
TGAGAGGGTCACCCATCCCCTGGTCGCCATGACGC

AGTCTATTTCGATCGCAGATTTCATCGTGAAAACT

GAAGATGGTTTTATGCCTTCAGATAGAGAAAATAT

-continued

TGTGTTAGATCGCTACTTGTCTAAAGAACTAAAAG

AACTAAGAGATAAATATAAAGATGAGAAGAATGAT

AGAGCATCACTTCGTATTAAAATGTTTTTGACGCC

AGCGCCATCACGTCGCTTCACTCAAAGAGGAGTAG

TGCCAATGAGAGAACTCAAAACTACGTCTGATCTC

ACAACTTCAATGTTCAACTTGATTACTGACTGGCT

ACTATCTGTGCTCGCCGATGAAGAAATGGCTGAAT

CTTTTGAACAATTCATTGAGAGCAAATTTCCAGAC

ATTTTTGCTTCAGCTGACAAATTGGCCAGATTTGC

TCAAAGGCTAGAAGATAAGCGCGACATTATGCATA

GAAATCCATCAAAGGCTTTGAACGCTTTCGGAGCA

TGTTTTTGGGCAGTCAAACCGACATATGTCACGGA

GGGCAAGTGCAATGTTGTGAGAGCTACCGACGATT

CTATTATACTAGAATTTGAGCCAATTCCGGAACAT

TTGCGATGTGGAAGAACAAGATCAACTTTCTATAA

ACTGTACCCACTGTCAGAAGAAGCTCCGGTGACAG

GTATGATCGCATTACGAGGCGTTGCAGGTAATCAA

TTTCTCATGTATCACGGGCACGGACATATTAGAAC

AGTTCCCTATCATGAAATGAGTGACGCAATCAGGT

CTTTTGCAAAGAAAAAGAGTGATGAGCTGGAAGCG

ATAGCGAAGTCATCACTCGCGGTCCACTGTGGTCA

GAAATTCATGAACATGCTTGATCAGATTAGATCAA

AACAGAAAATCGAAGATATCATAACACAAGCCAAA

CAGAATGATCGAAAGAAATAGATTGTGACAAATCC

ACCATTGCGTTTTTAA

RVB/Horse-wt/USA/KY1518/2021 VP7 gene
                              (SEQ ID NO: 201)
GAAATAATCAGAGATGGCGTTGCCATTGCTTCTCG

TCTTTGCTGCTTGTGCAAAAGCTCAATTAGTGATT

ACTCCAATCAGCAACCCGGAGATTTGTGTGCTGCA

CGCTAGTGATTGGAATGTGAATAGTTTCGGAGACA

ACTTTACAAATATTTTTGAAACGTATAATTCAGTG

ACTCTATCCTTTTACCAGTATGATAGTACAAACTA

TGATGTGATTGATATTATATCTAAGAGAGATTATT

CGTTGTGTCATATATTGGCAATAGACGTTATAAGG

CCAGAAATGGATTTCATTACGTTCCTTCAATCAAA

CAATGAGTGTTCGAAGTATGCAGGACAGAAAATAC

ACTATCAAAAACTCTCAACAAACGAAGAATGGTTT

GTTTATTCAAAGAATTTGAAGTTTTGTCCACTATC

TGACAGTCTAATTGGATTGTATTGCGATACGCAGA

TAAATGGTACATATTTTCCATTGTCAGAGAATGAG

-continued

AAATACGATGTTACGGATCTACCAGAATTTACAGA

AATGGGTTACGTTTTTTACTCGAATGATGACTTTT

ACATTTGTAAGCGCATCAATGAAGACAAATGGGTA

AATTATCATCTTTTCTACAGAGAATATTCGGCCTC

AGGGACGGTGTCAAGAGCTATCAGTTGGGACAATG

TATGGACAGGTTTCAAGACATTTGCGCAGGTTGTA

TATAAAATACTAGACATCTTTTTCAACAATAGAAG

AAACTTTGAGCCACGAGCATAAAGAAGACTAGGCG

AAA

RVB/Horse-wt/USA/KY1518/2021 NSP4 gene
                        (SEQ ID NO: 202)
AATTTCAGCCATCTTTGAATATCAAAGATGGCTGA

AATTAATGAAAGCATTAGCAATGTGTTAAATGTTT

TCGAAACACTTCAACATGAGACAATACATAACGTG

ATAAAGAACACGGCTTCGTCAAAATTACTAACGAA

TTGTGCACTGTCACTACTATCGATAGTCACTGTTG

CATTGGCAAAGAACAAAGTCAAATTACCGATTACA

AACAAAATACGTAGTAATATCAGGCACATCGCTGA

ATCAATTGTTTGGAGAGCTGAAACAACAATTAGAG

AAATCGTTAATGATGTTATTTCAAAGAATGACATT

TTCAAAGACATTATACATTTAACCGAAGAAGTTGA

AAGAATTAAACAATCTATATCCAAAATTAAGGGAA

TGGACGTGACTAAGGAAATTTTTGACTTATGTGAA

CGAAAAATGAGAGCAATCGATGATAAAATAGATGA

TGTGCAGAAATCATGTGAAAGGAGAATTAAAGATT

ATGACTGGAAAATCGCTGCATTAGCATCGCAGAAT

TTAAAATCAGTAGAAGCGCATGTTAGTATACAGAA

CCAAACAGCTGAGGTTATTAATGATGATGAGATGA

CAAAAAATAATATTGTTAGACAAGCAAGAACAAAA

TTGAATTCAAAGCGACAGCTGTGAGATGGGAACGT

CGTAGCGTATGATCTGCGTGTGCGATGTTCCG

RVB/Horse-wt/USA/KY 1518/2021 NSP5 gene
                        (SEQ ID NO: 203)
GGCAGTGGCTGGAAACGCTGCACTGTCCGCACTCT

GCCCTGAAATGTCTGAAGCATCTGAGTTTAGGTTT

CCAAGTGGAAATAGGAAAAGGGATAAGGTGAGCAA

AACGAGCAACAAGAAAATGCCTTCTGATTCTACGT

CAACTAAAAGTGAAAGTGAAACATCAAGTCGTAGC

GACGCAGTGTCGGTATACTCAGCCGAGACTATAAA

CTCTGAATACGAAGAAGCGTACAACAAGTTGAGAC

GTGAACCAGTTATAGAAGAAAGTAACGACTCTTGC

TGTTTGGATGAGTCTTTTCCAGCAATTGAAACTGT

TAAAAAAACGAGGCCGAAAAGAATTACTGAGGTCA

-continued

GATACGACCATTCGGATAACAGCGATATACTTGAA

AAGTTGTCTGAGTTAACCTTGGAACTTGAAAAGCT

GAAAACCGCAACGCAACCTGTTGGTGTTGATGCCG

CGTTTAATCAGATATTACGGAATGTCGACAATTTA

AATACTAAACAGAAGCAAGCACTAGTAAACGCTAT

TGTTAATTCAATGAACTAACTTGATAATAGATATG

AACATTCGTACAACAACGACATACTTAAGAAGCTA

TCTGAGTTAACTTTGGAACTTTAGATGTTGAAAAC

TGCAACGCAACTTGTTAGTGCTGACGCCGCGTTTA

ATTAGATATTGAGGAATGTTAATAATTTAAATGCT

AAATGAAAGCAAGCACTAGTAAACTATATTGTTAA

TTCAATGAACTAACTTAATCAGATTGTGG

Example 6—Primer and Probe Sequences for EqRVB

TABLE 5

EqRVB Primer and Probe Sequences

| EqRV B Target Gene | Primer and Probe ID | Primer/Probe Sequence 5'-3' | Position of the Primer and Probe | SEQ ID NO: |
|---|---|---|---|---|
| VP6 | VP6-UT02-F | GCGCTTATCCAACCAGAA | 440-457 | 204 |
| | VP6-UT02-R | GCCAATCGCTGCTCTAATA | 541-559 | 205 |
| | VP6-UT02-P | 6FAM-ACCAGCCAGTCTAA ATGGTGGCA-BHQ | 517-539 | 206 |
| NSP3 | NSP3-UT04-F | GCAATGAAGGATTGTGGTA TG | 148-168 | 207 |
| | NSP3-UT04-R | CCATTGTTGTACCAGTCAT TTG | 217-238 | 208 |
| | NSP3-UT04-P | 6FAM-CTGGACAATTGGC GCGATGCAT-BHQ | 172-193 | 209 |
| VP7 | VP7-UT06-F | TCAGTTGGGACAATGTAT GG | 651-670 | 210 |
| | VP7-UT06-R | TATGCTCGTGGCTCAAAG | 739-756 | 211 |
| | VP7-UT06-P | 6FAM-CAGGTTTCAAGAC ATTTGCGCAGGT-BHQ | 672-696 | 212 |

Example 7—Identification of a Ruminant Origin Group B Rotavirus Associated with Diarrhea Outbreaks in Foals Equine rotavirus group A (ERVA) is one of the most common causes of foal diarrhea. Starting in February 2021, there was an increase in the frequency of diarrhea cases in neonatal foals at 24-72 hours of age in Central Kentucky whose dams had been immunized with a commercial inactivated ERVA vaccine. Diagnostic investigation of fecal samples collected from seven foals with severe watery to hemorrhagic diarrhea failed to detect evidence of diarrhea-causing pathogens including ERVA. Based on Illumina-based metagenomic sequencing, we identified a novel equine rotavirus group B (ERVB) in fecal specimens from the affected foals in the absence of any other known enteric pathogens. We determined the complete protein-coding sequence of the ERVB. Interestingly, the sequence of all 11 segments had greater than 96% protein sequence identity with group B rotaviruses previously found in calves and goats. Furthermore, phylogenetic analysis demonstrated clustering of the ERVB with group B rotaviruses of ruminant origin, particularly with caprine and bovine strains from the USA. Subsequent analysis of 33 foal diarrheic samples by RT-qPCR identified 23 rotavirus B-positive cases (69.69%). These observations suggest that the ERVB originated from ruminants. It is in circulation in U.S. horses in which it has been associated with outbreaks of neonatal foal diarrhea in the 2021 foaling season in Kentucky. Emergence of the ruminant-like group B rotavirus in foals clearly warrants further investigation due to the significant impact of the disease in neonatal foals and its economic impact on the equine industry.

Introduction

Rotavirus (RV) is a common enteric pathogen associated with diarrhea in newborn children, animals, and birds.[1,2] Globally, rotavirus is the leading cause of diarrhea in children less than 5 years old.[3] The virus is a non-enveloped, double-stranded RNA virus, that belongs to the Reoviridae family.[4] The RV genome comprises 11 segments with each segment dedicated to coding for one protein (segment 11 is an exception; it codes for two non-structural proteins; NSP5 and NSP6). In most rotaviruses, segments 1, 2, 3, 4, 6, and 9 code for VP1, VP2, VP3, VP4, VP6, and VP7 respectively, while segments 5, 8, 7, 10, and 11 code for non-structural proteins NSP1-NSP6.[5] During viral replication, proteolytic enzymes like trypsin, cleave VP4 into VP5* and VP8*, which drives viral maturation and allows the virus to spread among exposed host species. The numbering of genome segments is based on the migration pattern of RNA segments in analytical gels that can vary between strains.[6]

The RV virion is an icosahedral, triple-layered particle (TLP). The innermost capsid layer is formed by VP2 protein, while VP6 forms the middle capsid layer. VP7 forms the outermost capsid layer in which the spike protein VP4 is embedded.[7] VP6 is most conserved among different strains within a RV group.[8] As a result, its sequence-based demarcation has been used extensively for RV group classification.[9] Based on the VP6 sequence, the RV genus is divided into species (also called groups/serogroups); currently there are 9 groups, namely A, B, C, D, F, G, H, I, J.[10] The outer capsid protein VP7 and spike protein VP4 are the major viral antigens that elicit neutralizing antibody responses, and which form the basis of the dual classification system for rotavirus group A (RVA). Based on serological assays and nucleotide sequences of outer capsid protein VP7 and spike protein VP4, RVA is further classified into G and P serotypes.[11] So far, 36 G serotypes and 51 P genotypes have been reported (Rotavirus Classification Working Group).

Although RVA is the most important causative agent associated with gastroenteritis and severe diarrhea in both children and newborn animals, rotavirus groups B (RVB), C (RVC), and H (RVH) can also cause clinical diarrhea in both humans and animals[2,12-14] Rotavirus groups D (RVD), F (RVF), and G (RVG) have been associated mainly with avian disease.[15] Interestingly, unlike RVA, RVB has the ability to cause outbreaks of a 'cholera-like diarrhea' in adults, as well as infants.[16-18] Sporadic or epidemic out-breaks of diarrhea associated with RVB were also reported in calves, adult cows, lambs, kids and adult goats, and piglets.[19] Zoonotic transmission of RVA has been well established with frequent reports of interspecies transmission.[20,21] The segmented nature of its genome allows for both genomic reassortment and recombination which can lead to the emergence of new antigenic variants.[22,23] Increasing evidence indicates reassortment events are not constrained among animal strains and that reassortment between animals and human strains can occur.[24-27] It is generally believed that RVA reassortants can jump species and infect and spread in new host species. Thus, continuous surveillance and monitoring of RVs in both animals and humans are essential for the prevention of future diarrhea outbreaks as well as for the implementation of timely countermeasure strategies.

Equine rotavirus group A (ERVA) is one of the most common causes of severe dehydrating diarrhea in foals less than 3 months old, and their prevalence can vary from 20% to as high as 77% in outbreaks of the disease.[28] To date, 6 G types (G3, G14, G5, G8, G10, G13) and 6 P types (P[1], P[3], P[7], P[11], P[12], P[18]) have been reported to be associated with outbreaks of clinical diarrhea in foals.[29-36] Of these genotypes, G3P[12] and G14P[12] are the most prevalent genotypes around the world. Equine G3P[12] genotypes were isolated in 1975, whereas equine G14P[12] genotypes were discovered in 2005.[28,37,38] In addition to posing a significant health concern to the equine industry, ERVA, especially those G3 genotype-derived reassortants, has been found to spread and cause clinical diarrhea in children.[39] Cross-species transmission has also been described for infrequently occurring equine rotavirus A strains like G5P[7] and G3P[3] involving spillover events from pigs and cats to horses, respectively.[40-42] Intriguingly, despite frequent detection of RVB in human diarrhea cases as well as in a variety of agricultural animal species, including calves and goats, research on RVB and the associated diarrhea in horses is very limited. To date, only a single study reported on the presence of RVB in horses in Germany.[43] This early work with a focus on the detection of rotavirus species A, B, and C in domestic animals found that one out of a total of 37 equine samples (2.7% detection rate) tested positive for RVB in an RT-PCR assay. The associated disease status in that RVB-positive horse and viral genome sequence were not investigated in that study.

In this study, we investigated the causative agent(s) of a series of diarrhea outbreaks that occurred in the 2021 foaling season in Kentucky, USA, in neonatal foals at approximately 24-72 hours of age. Other clinical signs included inappetence, mild colic, and transient ileus. Affected foals were largely born to mares that received prior immunization with a commercial inactivated equine rotavirus group A G3P[12] vaccine (Zoetis). ERVA and other significant diarrhea-causing pathogens were negative in most cases of diarrhea in the course of this investigation. Using next-generation sequencing, we identified a novel group B rotavirus in feces and fecal swabs from foals suffering from watery diarrhea. Furthermore, we determined the complete genome sequence of this ERVB from pooled fecal/swab samples, except for small portions of non-coding sequences at the 5' and 3' ends. Interestingly, the genomic analysis demonstrated that the novel virus exhibited more than 96% overall amino acid identity to ruminant RVB, indicating the possibility that the virus was ruminant in origin. These findings confirm for the first time the circulation of a group B rotavirus in horses in which it can be associated with enteric disease.

Material and Methods

Ethics statement. Foal feces or fecal swab samples were collected as part of a routine diagnostic investigation by licensed veterinarians and submitted to the University of Kentucky's Veterinary Diagnostic Laboratory or the Gluck Equine Research Center, Lexington, USA.

Fecal sample collection and viral metagenomic Sequencing. Feces were collected from three neonatal foals (2-7 days of age) with severe watery to hemorrhagic diarrhea. Approximately 1 gram of feces from each foal was pooled together and used for metagenomic sequencing. In addition, fecal swabs were collected from four neonatal foals between 2-6 days old that suffered from diarrhea, and a pooled sample from these four fecal swabs was also included in the metagenomic sequencing analysis. Note that these fecal samples were derived from five equine farms affected with foal diarrhea during the 2021 foaling season which are located in proximity to Lexington, Kentucky, USA.

The standard Illumina MiSeq-based metagenomic sequencing method was used for the identification of the causative agent likely responsible for the outbreaks of idiopathic foal diarrhea. Briefly, clarified feces and fecal swab pooled samples were treated with nucleases followed by nucleic acid isolation. Reverse transcription and second-strand synthesis were performed with barcoded random hexamers followed by amplification with barcode primers. Sequencing libraries for each of the pooled samples were constructed with a Nextera XT library preparation kit (Illumina) followed by sequencing on a MiSeq instrument. Approximately 0.9-1.2 million paired 151 base pair (bp) reads were generated per pooled sample. Contigs were assembled de novo using CLC Genomics and analyzed by BLASTX using the BLAST2Go plugin and the non-redundant protein sequence database in May 2020.

Genome sequencing and analysis. Contigs encoding proteins with homology to ruminant RVB were identified by BlastP analysis. The genome sequence of segments 1-11 of RVB/Horse-wt/USA/KY/1518 was submitted to Genbank under accession no. MZ327688-MZ327698, respectively. Phylogenetic analyses were performed using MEGA X software [51]. Evolutionary analyses were conducted using the Maximum Likelihood algorithm, and tree topology was verified by performing 1000 bootstrap replicates.

Transmission Electron Microscopy: Fecal samples from two foals suffering from watery diarrhea were resuspended in distilled water (10% suspension) and lysed in tissue-lyser with beads. Following low-speed centrifugation, the supernatant was passed through a 450 nm filter. A total of 190 μl of the filtrate was subjected to ultracentrifugation ($199 \times 10^3$ g for 2 h) using an Airfuge air-driven ultracentrifuge (Beckman-Coulter, Indianapolis, IN). Pellets (20 μl) were resuspended and negatively stained with 1.3% phosphotungstic acid followed by examination on a JEOL JEM 1400 transmission electron microscope (JEOL USA Inc, Peabody, MI).

Detection of equine rotavirus group B genome in clinical samples. Forty-two feces and fecal swab samples (n=42), originating from 22 equine farms in Central Kentucky, were analyzed for ERVB using RT-qPCR. Nine of the samples were from healthy foals, and 33 were from foals with watery or hemorrhagic diarrhea. Most of these neonatal foals were 2-7 days of age. We deployed two standard RT-qPCR assays for the molecular detection of ERVB in clinical samples. RT-qPCR assay I targeted the VP7 gene of ERVB with one pair of primers (forward, nucleotide region 651-670; reverse, nucleotide region 739-756) and a Taqman probe (nucleotide region 672-696, labeled with FAM dye at the 5' end and BHQ at the 3'end). RT-qPCR assay II involved NSP2-targeting primers (forward, nucleotide region 655-674; reverse, nucleotide region 788-807); and a probe (nucleotide region 703-725). The detailed sequences of primers and probes will be provided upon request.

Viral RNAs were extracted from clinical samples by using the PureLink viral RNA/DNA isolation kit (Invitrogen) according to the manufacturer's instructions. RT-PCR was performed using the applied biosystem TaqMan RNA-to-Ct one-step kit in the ViiA 7 Real-Time PCR instrument (Applied Biosystems) for Assay I and Path-ID™ Multiplex One-Step RT-PCR Kit for Assay II (Thermofisher, MA, USA).

Thermal cycling conditions were as follow: initial reverse transcription, 48° C. for 15 min; PCR activation, 95° C. for 10 min, followed by 40 cycles of 15 s at 95° C., 60 s at 60° C.

Results

Foal Diarrhea Outbreak

Foal diarrhea cases were increasingly being reported in newborn foals aged 2-7 days from different farms in Central Kentucky, USA, at the beginning of the 2021 foaling season (February and March). Mares were vaccinated with an inactivated monovalent ERVA vaccine during their pregnancy according to the manufacturer's recommendations (https://www.zoetisus.com). Foals developed diarrhea at approximately 48 hours of age and diarrheic episodes typically lasted 3-4 days. Farms experiencing diarrhea experienced up to 100% morbidity with each new foal born on the farm succumbing to disease following their index case suggesting a highly contagious nature of the disease. Farms able to break this pattern were those implementing strict biosecurity protocols. Foals required intensive medical care either on the farm or at referral hospitals in Lexington. The rapid and intense medical intervention provided by the veterinary care facilities in Central Kentucky enabled an extremely high survival rate in these cases. The clinical signs included inappetence, weakness, dehydration, severe electrolyte imbalance, watery yellow, and foul-smelling diarrhea. While hemorrhagic watery diarrhea was also noticed in some cases, there were no flecks of blood present in samples from affected foals. None of the dams of the foals developed diarrhea. Despite samples from foal diarrhea cases testing negative on an ERVA specific RT-qPCR assay, transmission electron microscope (TEM) examination of diarrhea samples from two diseased foals revealed single and clusters of round particles (~0.1 μm 0) with electron-dense "surface holes" characteristic of rotavirus particles (FIG. 1). The combination of TEM and RT-qPCR data indicated that a non-A rotavirus was implicated in causing the series of neonatal foal diarrhea outbreaks.

Seven representative foal diarrhea samples collected from five equine farms in the Lexington, Kentucky area were tested using a common enteric pathogens foal & neonate GI/Diarrhea panel (*Clostridium difficile* toxins A and B, equine coronavirus, *Lawsonia intracellularis, Salmonella* spp, *Cryptosporidium* spp, equine rotavirus group A, *Rhodococcus equi, Clostridium perfringens*). All seven samples tested negative for all of the agents included in the panel, except for three samples that were positive for *C. perfringens*. The detection of *Clostridium perfringens* in equine fecal samples may be insignificant as these bacteria can also be found in samples from non-diarrheic healthy foals (data not shown).

Identification of a Novel Group B Rotavirus by Next-Generation Sequencing

The afore-mentioned seven samples negative on testing with neonate GI/Diarrhea panel, were further investigated by lumina MiSeq-based deep RNA sequencing. Approximately 1 gram of feces, from each of three diarrheic foals, was pooled together and used for the metagenomic sequencing. In addition, fecal swabs from the other four neonatal foals were pooled together in the same experiment. Sequencing libraries were constructed for each pool individually using a Nextera XT library preparation kit followed by sequencing on a MiSeq instrument using paired 150-bp reads. Sequenced reads were trimmed of adapter sequences using onboard software before being exported to CLC Genomics and assembled de novo. Contig sequences were analyzed by BLASTX using the BLAST2Go plugin incorporated into that software package.

For pooled feces, approximately 1,194,168 reads were generated and 45.5% of the total sequence reads were mapped to ruminant RVB. Similarly, approximately 937,432 reads were generated for the fecal swab pool and 72% of the total reads mapping to RVB. In-depth analysis of sequence reads failed to identify RVA or other viral or bacterial enteric pathogens of known concern as a cause of foal diarrhea. Total sequencing reads from each pool were used to assemble the respective full-length genome sequence of the ERVB, except for certain non-coding sequences at the termini of a few segments. We focused on fecal swab-derived consensus full-genome sequence for further analysis in consideration of more reads generated for the rotavirus B sequence and additional validation by separate metagenomic sequencing. The virus was provisionally designated RVB/Horse-wt/USA/KY/1518/2021.

As summarized in Table 6, nucleotide blast analysis of RVB/Horse-wt/USA/KY/1518/2021 revealed that segment 1 (VP1), segment 2 (VP2), segment 3 (VP3), segment 5 (NSP1), and segment 7 (NSP3) aligned best with segment 1, segment 2, segment 3, segment 5, and segment 7 of RVB/Goat-wt/USA/Minnesota-1/2016 with 93.19%, 97.82%, 95.04%, 95.75%, and 97.84% sequence identity, respectively. Similarly, segment 4 (VP4), segment 6 (VP6), segment 8 (NSP2), and segment 11 (NSP5/NSP6) of the equine virus showed 97.40%, 96.34%, 97.90%, and 96.41% sequence identity, respectively, with its corresponding segments in a different caprine virus, RVB/Goat-wt/USA/CA22/2014. It is intriguing that segment 9 (VP7) of RVB/Horse-wt/USA/KY/1518 scored best in sequence alignment with a bovine virus, RVB/Cow-wt/USA/MN10-1/2010 G3P [X], with 96.37% sequence identity. Furthermore, segment 10 (NSP4) of the equine virus had the most homology with its counterpart in another bovine virus, RVB/Cow-wt/JPN/IS-1/1999/G3[P] with 94.26% sequence identity. In summary, the nucleotide BLAST analysis appears to indicate that the equine rotavirus B associated with the diarrhea outbreaks in foals may have evolved from ruminants.

TABLE 5

Blastn analysis of the eleven segments of RVB/Horse-wt/USA/KY1518/2021

| Segment¦ Gene¦ length (nt) | Best blastn hit virus¦ accession number¦ identity |
|---|---|
| 1 ¦ VP1¦ 3503 | RVB/Goat-wt/USA/Minnesota-1/2016 ¦KY689687.1¦ 93.19% |
| 2 ¦ VP2¦ 2889 | RVB/Goat-wt/USA/Minnesota-1/2016 ¦KY689688.1¦ 97.82% |
| 3 ¦ VP3¦ 2340 | RVB/Goat-wt/USA/Minnesota-1/2016 ¦KY689689.1¦ 95.04% |
| 4 ¦ VP4¦ 2324 | RVB/Goat-wt/USA/CA22/2014 ¦MG272136.1¦ 97.40% |
| 5 ¦ NSP1¦ 1252 | RVB/Goat-wt/USA/Minnesota-1/2016 ¦KY689691.1¦ 95.75% |
| 6 ¦ VP6¦ 1221 | RVB/Goat-wt/USA/CA22/2014 ¦MG272162.1¦ 96.34% |
| 7 ¦ NSP3¦ 1007 | RVB/Goat-wt/USA/Minnesota-1/2016 ¦KY689693.1¦ 97.84% |
| 8 ¦ NSP2¦ 961 | RVB/Goat-wt/USA/CA22/2014 ¦MG271985.1¦ 97.90% |
| 9 ¦ VP7¦ 773 | RVB/Cow-wt/USA/MN10-1/2010/G3P[x]¦JQ288103.1¦ 96.37% |
| 10¦ NSP4¦ 697 | RVB/Cow-wt/JPN/IS-I/1999/G3P[x] ¦LC185678.1¦ 94.26% |
| 11¦ NSP5¦ 764 | RVB/Goat-wt/USA/CA22/2014 ¦MG272051.1¦ 96.41% |

Table 6. Blastn analysis of the eleven segments of RVB/ Horse-wt/USA/KY1518/2021

De novo genome assembly and open reading frame (ORF) analysis found a single ORF for all 11 segments. Further protein sequence analysis showed that all segments had greater than 96% identity with ruminant group B rotaviruses represented by RVB/Goat-wt/USA/Minnesota-1/2016, RVB/Goat-wt/USA/CA22/2014, RVB/Cow/Nemuro, and RVB/Cow-wt/JPN/IS-2/2002/G3P[X] (Table 6). Segments with more than 99% homology to ruminant group B viruses were NSP3 (99.66%), VP7 (99.60%), NSP2 (99.33%), and VP2 (99.15%), while the most divergent segments were NSP1 (96.25%), and NSP4 (96.63%). Segments within 97-99% identity between equine and ruminant viruses included VP4 (97.10%), VP1 (97.15%), VP3 (97.38%), NSP5 (97.59%), and VP6 (98.98%). Comparative nucleotide and amino acid sequence analysis of all 11 segments supports the theory that the novel equine group B rotavirus originated from ruminants; this warrants further investigation.

TABLE 6

| Blastp analysis of the eleven putative open reading frames of RVB/Horse-wt/USA/KYl518/2021 | | |
| --- | --- | --- |
| Segment¦ Protein¦ ORF (aa) | Best blastp hit virus¦ accession number¦ identity | Protein Function |
| 1 ¦VP1 ¦1158 | RVB/Goat-wt/USA/Minnesota-1/2016¦ASV45167.1¦97.15% | RNA-dependent RNA polymerase (RdRp) |
| 2 ¦VP2 ¦937 | RVB/Goat-wt/USA/CA22/2014 ¦AUG44960.1¦99.15% | Outer core protein; essential for RdRp activity |
| 3 ¦VP3 ¦763 | RVB/Goat-wt/USA/Minnesota-1/2016¦ASV45169.1¦97.38% | Catalyzes the addition of 5' cap on vRNA |
| 4 ¦VP4 ¦759 | RVB/Goat-wt/USA/Minnesota-1/2016¦ASV45170.1¦97.10% | Essential for attachment to host cell |
| 5 ¦NSP1 ¦320 | RVB/Goat-wt/USA/CA22/2014¦AUG44808.1¦96.25% | Interferon antagonist |
| 6 ¦VP6 ¦391 | RVB/Goat-wt/USA/CA22/2014¦AUG45028.1¦98.98% | Essential for transcription of double layered particles |
| 7 ¦NSP3¦296 | RVB/Goat-wt/USA/Minnesota-1/2016¦ASV45174.1¦99.66% | Inhibits host mRNA translation; promotes vRNA translation |
| 8 ¦NSP2¦300 | RVB/Goat-wt/USA/CA22/2014¦AUG44851.1¦99.33% | Packaging of vRNA; viroplasm formation |
| 9 ¦VP7 ¦247 | RVB/Cow/Nemuro ¦BAA78609.1¦99.60% | Interacts with host cell receptor |
| 10¦NSP4¦208 | RVB/Cow-wt/JPN/IS-2/2002/G3P[x]¦BAW98439.1¦96.63% | Acts as viroporin; enterotoxin |
| 11¦NSP5¦166 | RVB/Goat-wt/USA/CA22/2014¦AUG44917.1¦97.59% | NSP5: interacts with VP2; viroplasm formation NSP6: interacts with NSP5 |

Phylogenetic Analysis

To further understand viral evolution, we performed phylogenetic analysis of the novel equine group B rotavirus, and representative group B viruses of various species acquired from the NCBI database (ncbi.nlm.nih.gov/nuccore/?term=Rotavirus+B, accessed Apr. 20, 2021) using MEGA X [44]. The evolutionary history of all the 11 segments of RVB/Horse-wt/USA/KY/1518/2021/GXP[X] was analyzed individually by constructing maximum likelihood trees, using the best nucleotide substitution models suggested by the goodness-of-fit criteria in MEGA X (FIGS. 2A-4E). The best substitution models inferred for the maximum likelihood trees were general time-reversible model with gamma distribution and invariant sites (GTR+G+I) for VP1, VP2, VP3, VP6, NSP1 segments; Hasegawa-Kishino-Yano model with gamma distribution and invariant sites (HKY+G+I) for VP4, NSP4; Tamura 3-parameter with gamma distribution and invariant sites (T92+G+I) for VP7; Tamura-Nei with gamma distribution and invariant sites (TN93+G+I) for NSP2, NSP3, and NSP5 segments. For the analyses, complete or near-complete nucleotide sequences of the RVB strains of swine, human, caprine, bovine and murine origin were included, while the gaps or missing data were removed during the analyses. For each taxon, the bootstrap value was determined from 1000 replicates to verify the tree topology. The total number (given in parentheses) of RVB sequences used for the phylogenetic analyses for each segment were VP1 (n=54), VP2 (n=48), VP3 (n=46), VP4 (n=51), VP6 (n=66), VP7 (n=70), NSP1 (n=57), NSP2 (n=58), NSP3 (n=59), NSP4 (n=55), and NSP5 (n=54).

Phylogenetic analyses of the genes encoding all the structural and non-structural proteins revealed a high level of divergence of ruminant RVB strains from the porcine, murine and human RVB (FIGS. 2A-4E), which is similar to what has been previously described [27,45]. In general, all 11 genes of this novel equine RVB strain clustered more closely with the RVB strains of ruminant origin than with those of porcine, or murine, or human strains, indicating the likelihood of a cross-species transmission event between ruminants and equines. The phylogenetic analyses also showed that the RVB/Horse-wt/USA/KY/1518/2021 shared a common ancestor with the bovine and caprine RVB strains. Moreover, for all RVB segments (FIGS. 2A-4E) except VP3 (FIG. 2C), NSP3 (FIG. 4C), and NSP4 (FIG. 4D), the novel ERVB is more closely related to the ruminant RVB strains from Japan and the USA than to the Indian bovine RVB cluster. The sequences for VP3, NSP3, and NSP4 segments of Indian bovine RVB strains were not available in the database and hence were not included in the phylogenetic analyses. Also, RVB/Rat/USA/IDIR clustered more closely with the human RVB strains than with the ruminant and porcine RVB strains for all 11 segments.

Figure 2A:
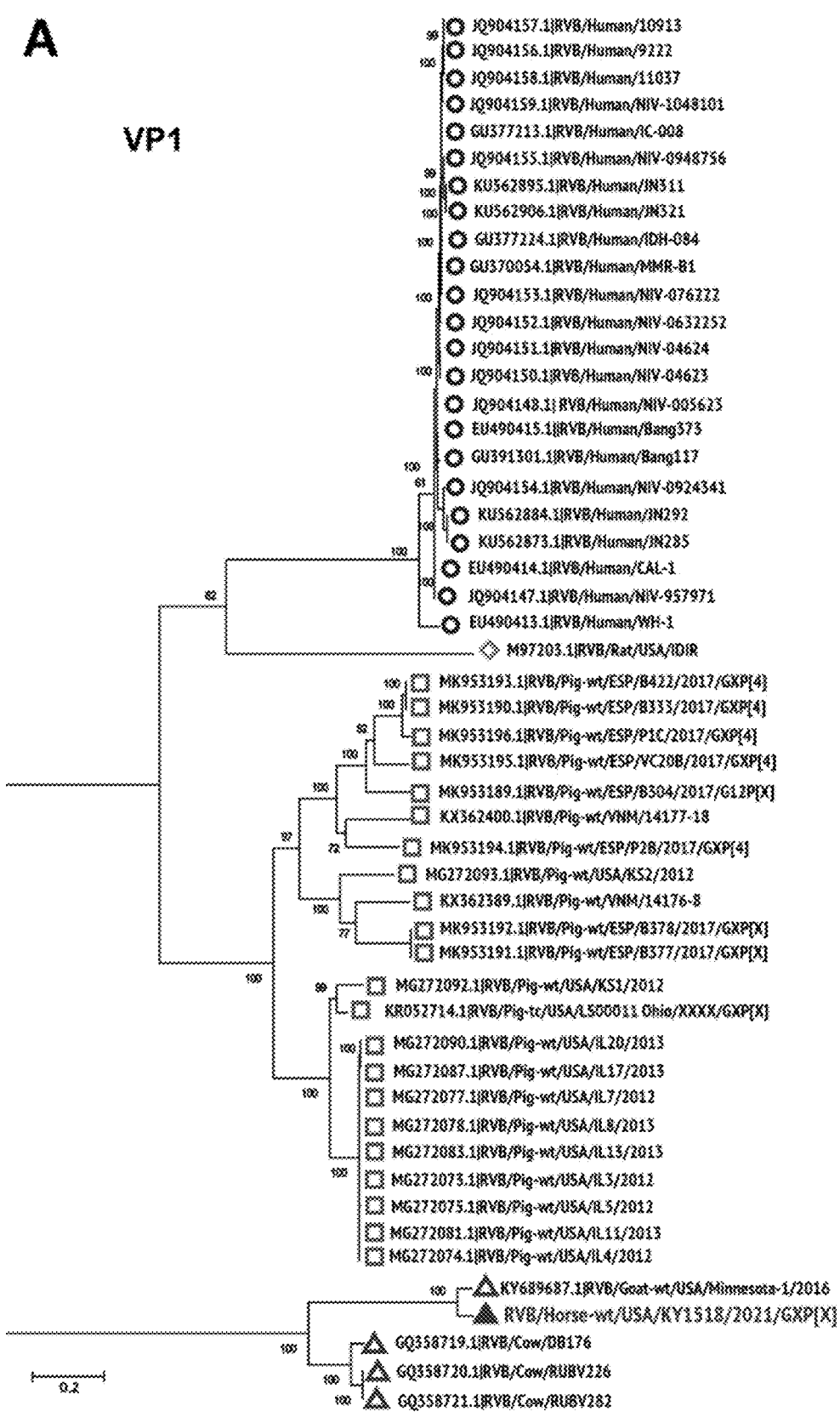
FIGS. 2A-C show images illustrating maximum likelihood trees for RVB genes VP1, VP2, and VP3. (A) Maximum likelihood tree for VP1 gene. (B) Maximum likelihood tree for VP2 gene. (C) Maximum likelihood tree for VP3 gene.
Figure 2B:
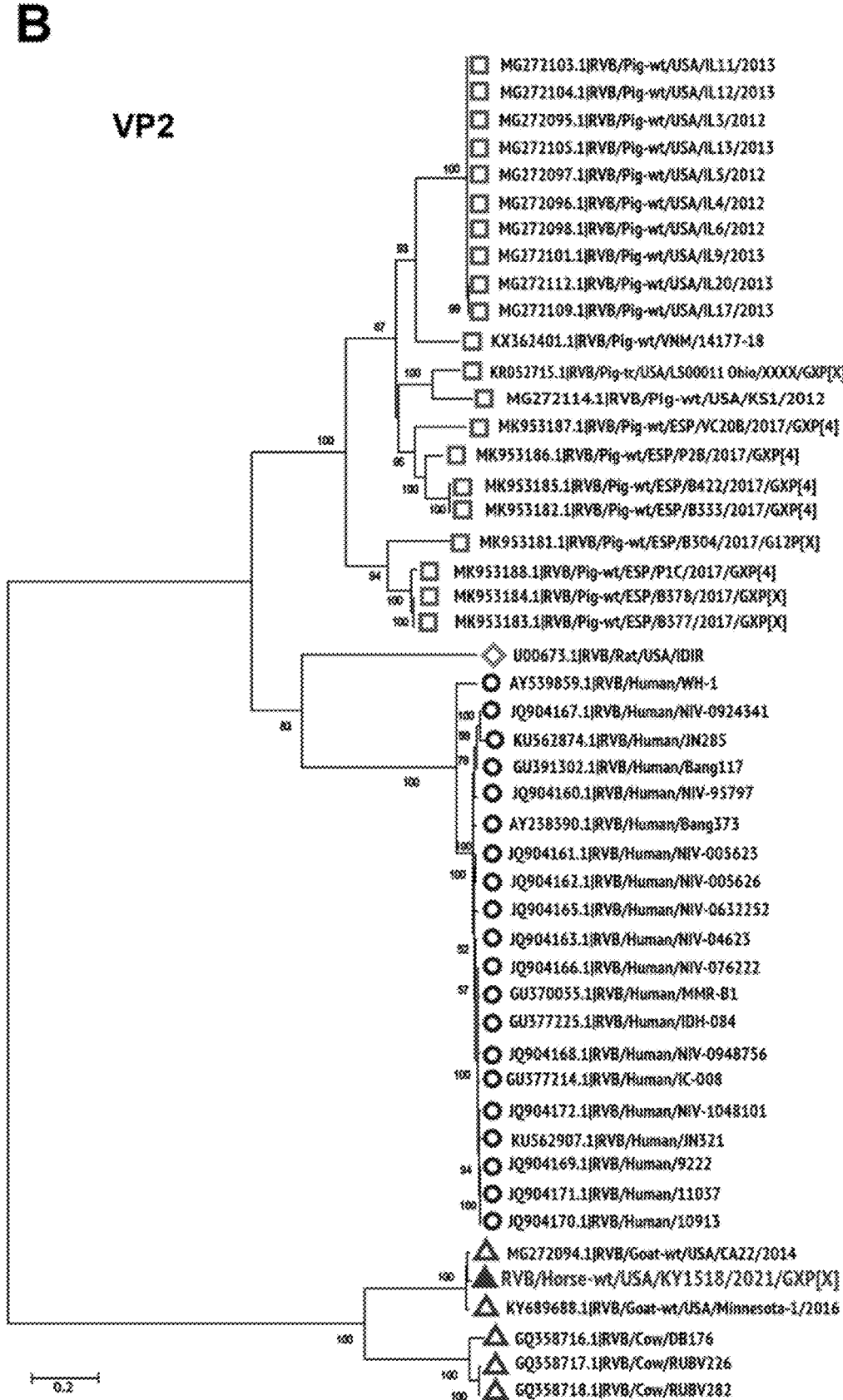
Figure 2C:
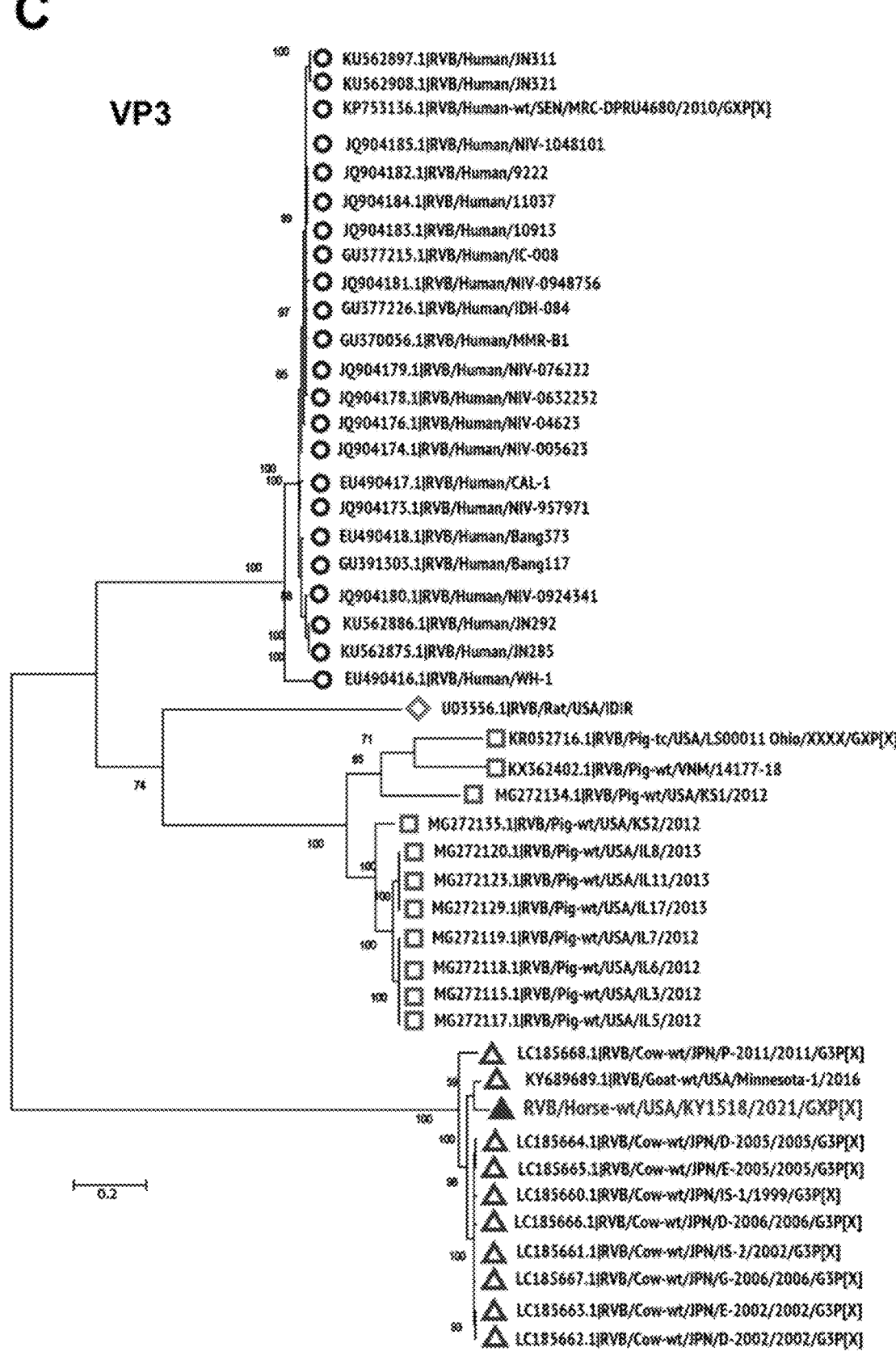

Phylogenetic characterization of the viral core assembly proteins VP1, VP2, and VP3 are shown in FIGS. 2A-C. The VP1 gene encoding RNA-dependent RNA polymerase (RdRp) protein is the largest protein that aids transcription and genome replication [46]. The VP1 gene of the RVB/Horse-wt/USA/KY/1518/2021 clustered more closely with a caprine RVB strain RVB/Goat-WT/USA/Minnesota-1/2016 originating from the USA, followed by three bovine strains (DB176, RUBV226, and RUBV282) from India (FIG. 2A). The VP2 gene encodes the most abundant structural protein that forms the outer core protein, which is essential for RNA binding and RdRp activity [47]. The gene encoding the VP2 segment of RVB/Horse-wt/USA/KY/1518/2021 shared a common ancestor with the bovine RVB strains of Indian origin and clustered more closely with two caprine strains from the USA, RVB/Goat-wt/USA/CA22/2014 and RVB/Goat-WT/USA/Minnesota-1/2016 (FIG. 2B). The VP1 protein forms an enzyme complex with the VP3 capping enzyme, which catalyzes the addition of a 5' cap on the viral RNA [48]. Similar to VP1, the VP3 segment of the RVB/Horse-wt/USA/KY/1518/2021 strain formed a group with RVB/Goat-WT/USA/Minnesota-1/2016, clustering with the Japanese RVB strains of bovine origin (FIG. 2C).

Figure 3A:
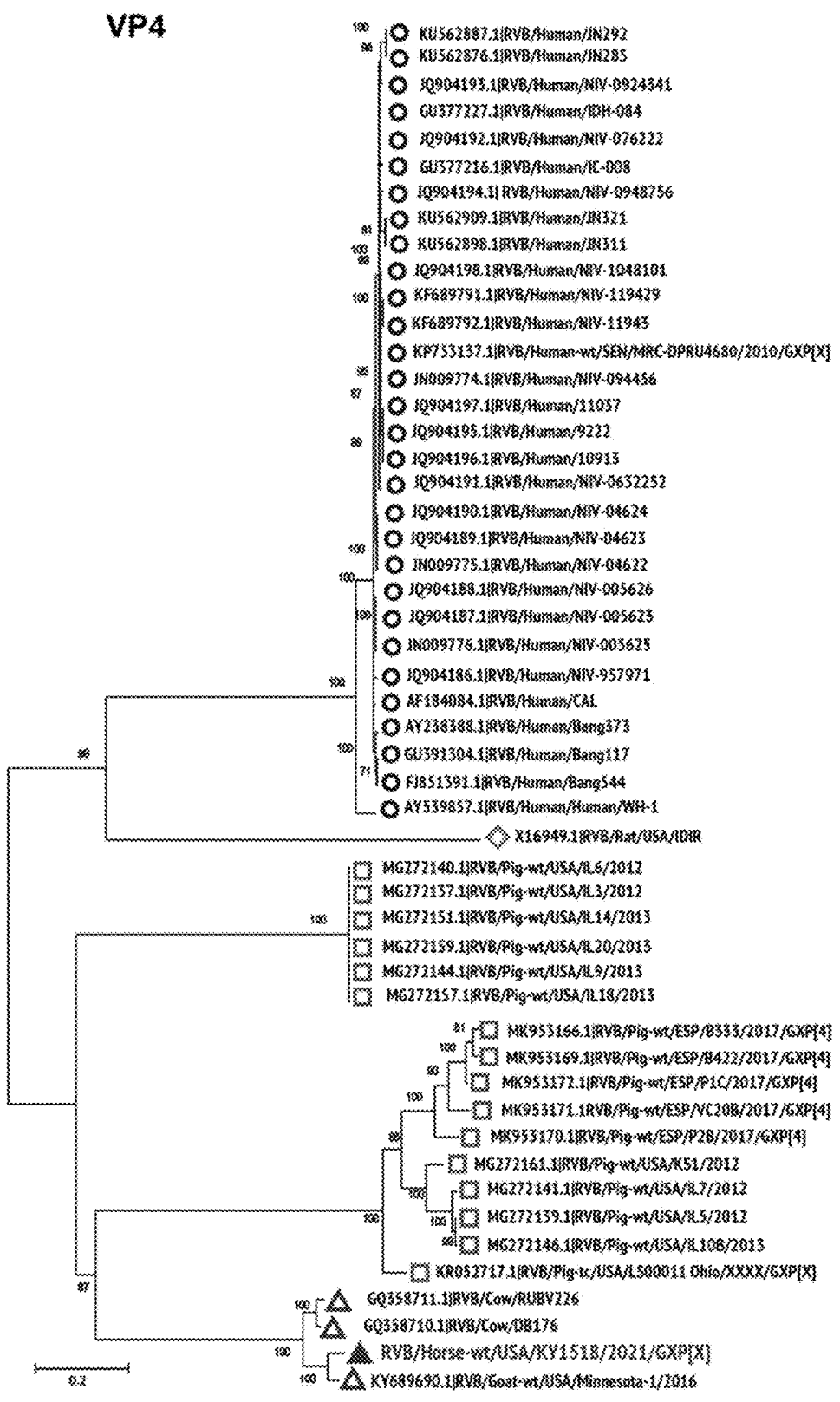
FIGS. 3A-C show images illustrating maximum likelihood trees for RVB genes VP4, VP6, and VP7. (A) Maximum likelihood tree for VP4 gene. (B) Maximum likelihood tree for VP6 gene. (C) Maximum likelihood tree for VP7 gene.
Figure 3B:
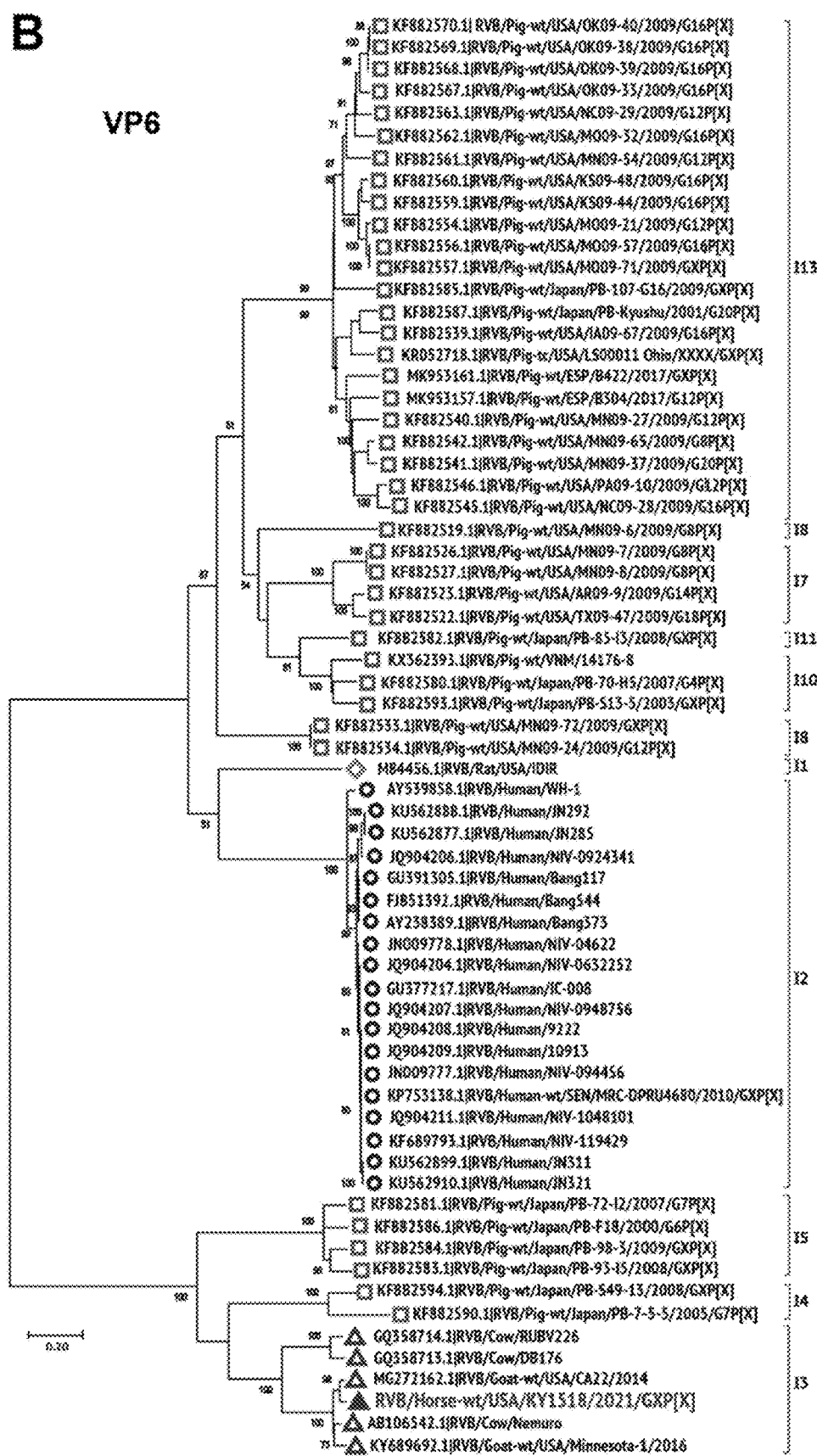
Figure 3C:
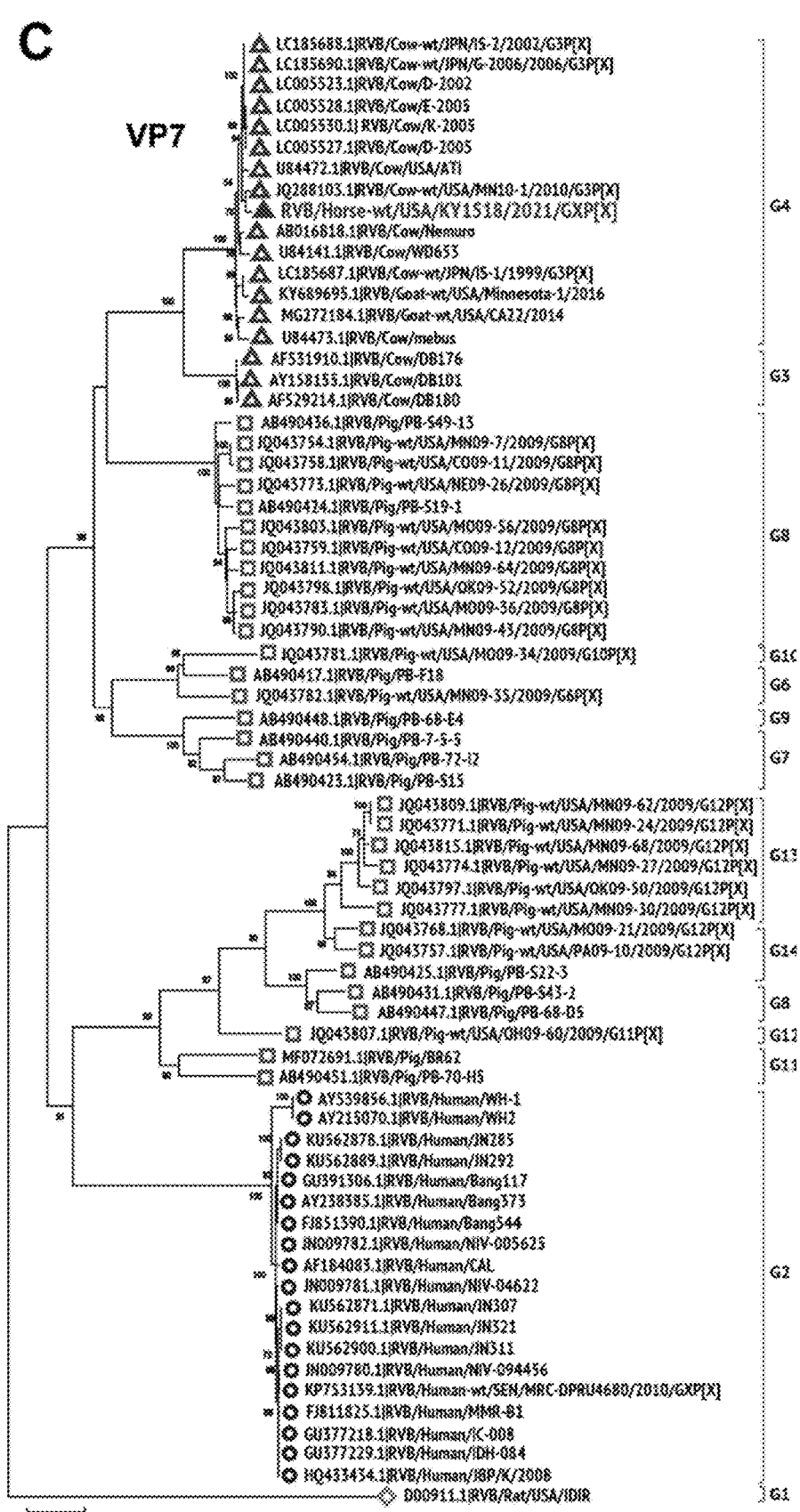

The outer capsid proteins VP4 and VP7, form the outermost layer of the rotavirus and possess diverse biological properties involved in receptor binding, tissue tropism, and immunogenicity [49-51]. These two proteins are also primary targets of virus-neutralizing antibodies. Like VP1 and VP3 genes, the VP4 segment of the RVB/Horse-wt/USA/KY/1518/2021 grouped with the caprine strain from the USA and bovine strains from India, clustering more closely with RVB/Goat-WT/USA/Minnesota-1/2016 (FIG. 3A). VP6, the inner capsid protein, is the most conserved protein across rotavirus groups and is the basis of group demarcation in the new Rotavirus classification system [9]. VP7 is the second most abundant protein that interacts with host cell receptors and elicits neutralizing antibody responses. While the inner capsid protein VP6 clustered more closely with the caprine strain RVB/Goat-wt/USA/CA22/2014 (FIG. 3B), the outer capsid protein VP7 shared a close phylogenetic relationship with bovine RVB strains, clustering more closely with RVB/Cow-wt/USA/MN10-1/2010/G3P[X] (FIG. 3C). The VP7 segment of the novel equine RVB strain is most closely associated with the bovine and caprine strains from the USA and Japan in the G4 group, followed by the Indian bovine strains that were initially designated G4 strains, but recently reclassified and placed into the G3 genotype (FIG. 3C) [27]. In the case of VP6, RVB/Horse-wt/USA/KY/1518/2021 belonged to the 13 genotype, along with the rest of North American, Japanese, and Indian ruminant RVB strains (FIG. 3B).

Similar to the structural proteins, the evolutionary history of the non-structural proteins of the RVB/Horse-wt/USA/

Figure 4A:
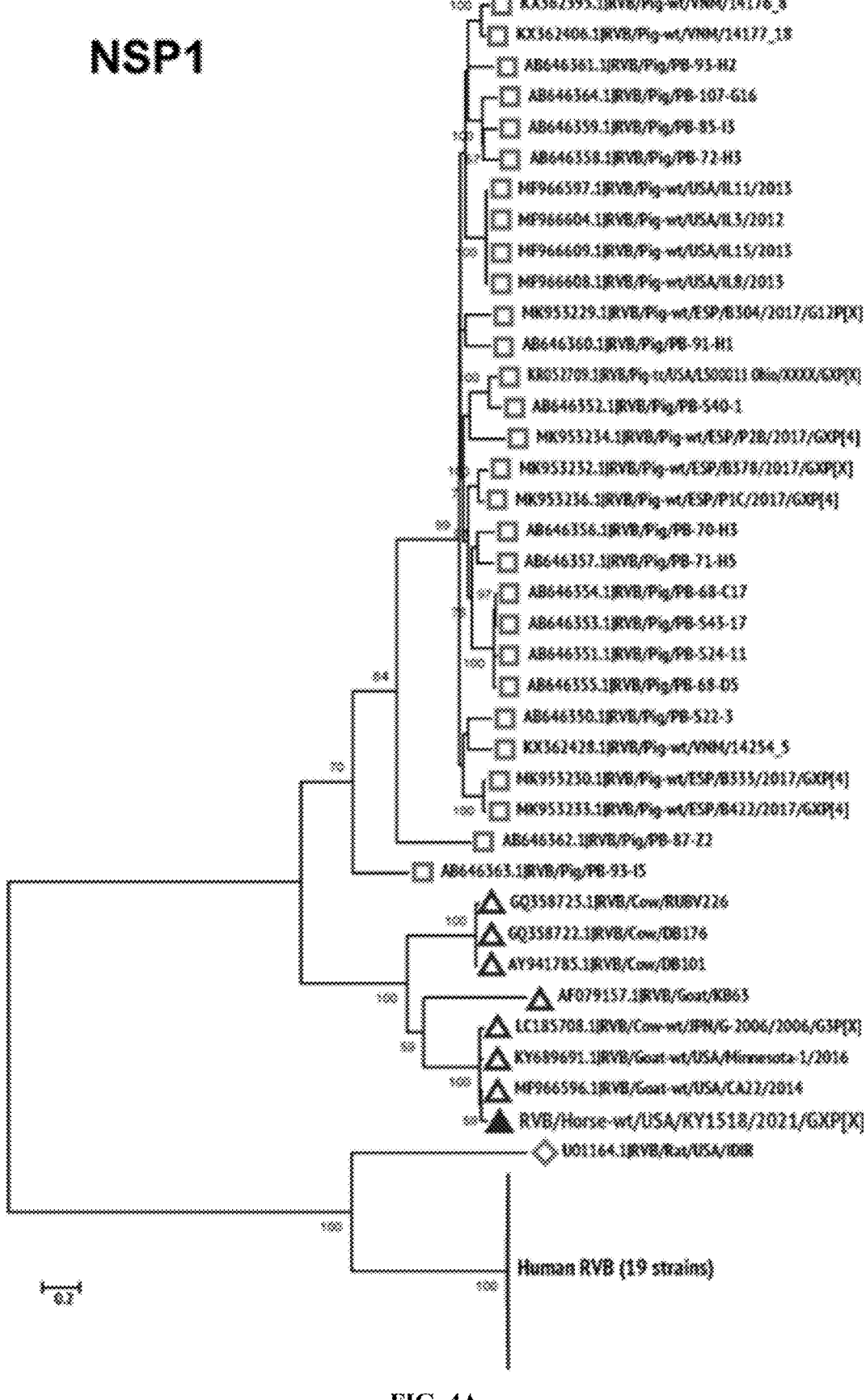
FIGS. 4A-E show images illustrating maximum likelihood trees for RVB genes NSP1, NSP2, NSP3, NSP4, and NSP5. (A) Maximum likelihood tree for NSP1 gene. (B) Maximum likelihood tree for NSP2 gene. (C) Maximum likelihood tree for NSP3 gene. (D) Maximum likelihood tree for NSP4 gene. (E) Maximum likelihood tree for NSP5 gene.
Figure 4B:
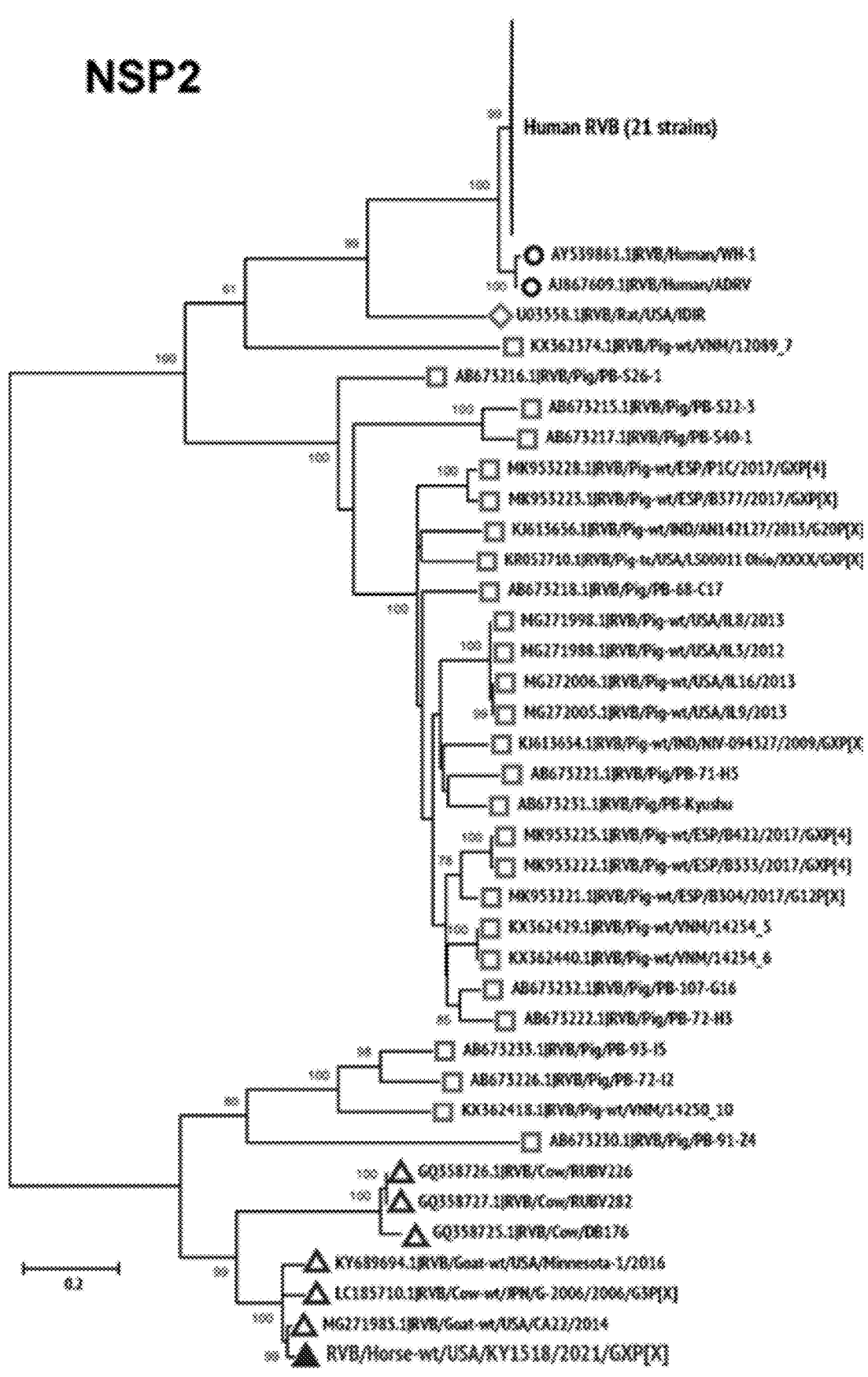
Figure 4C:
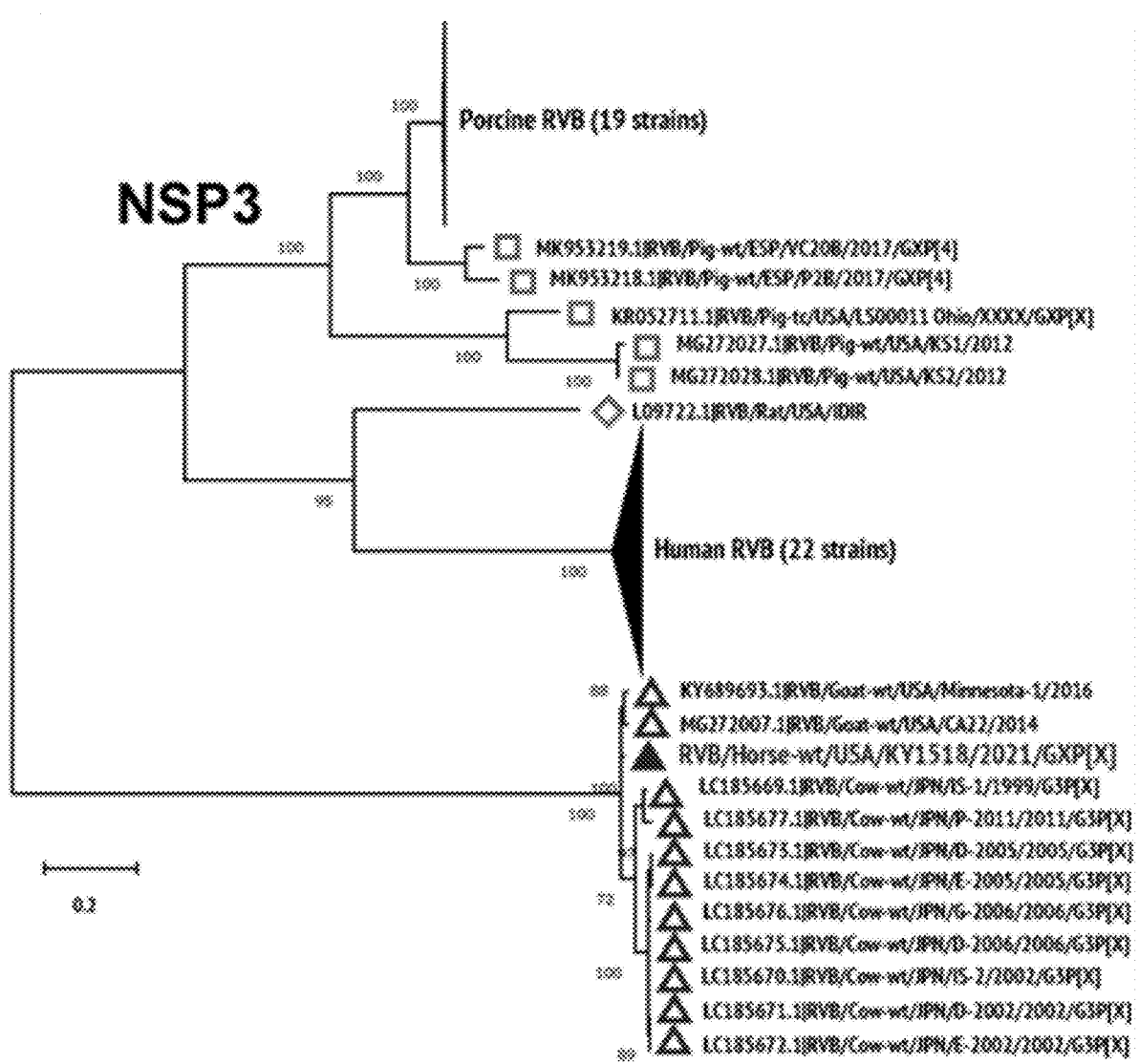
Figure 4D:
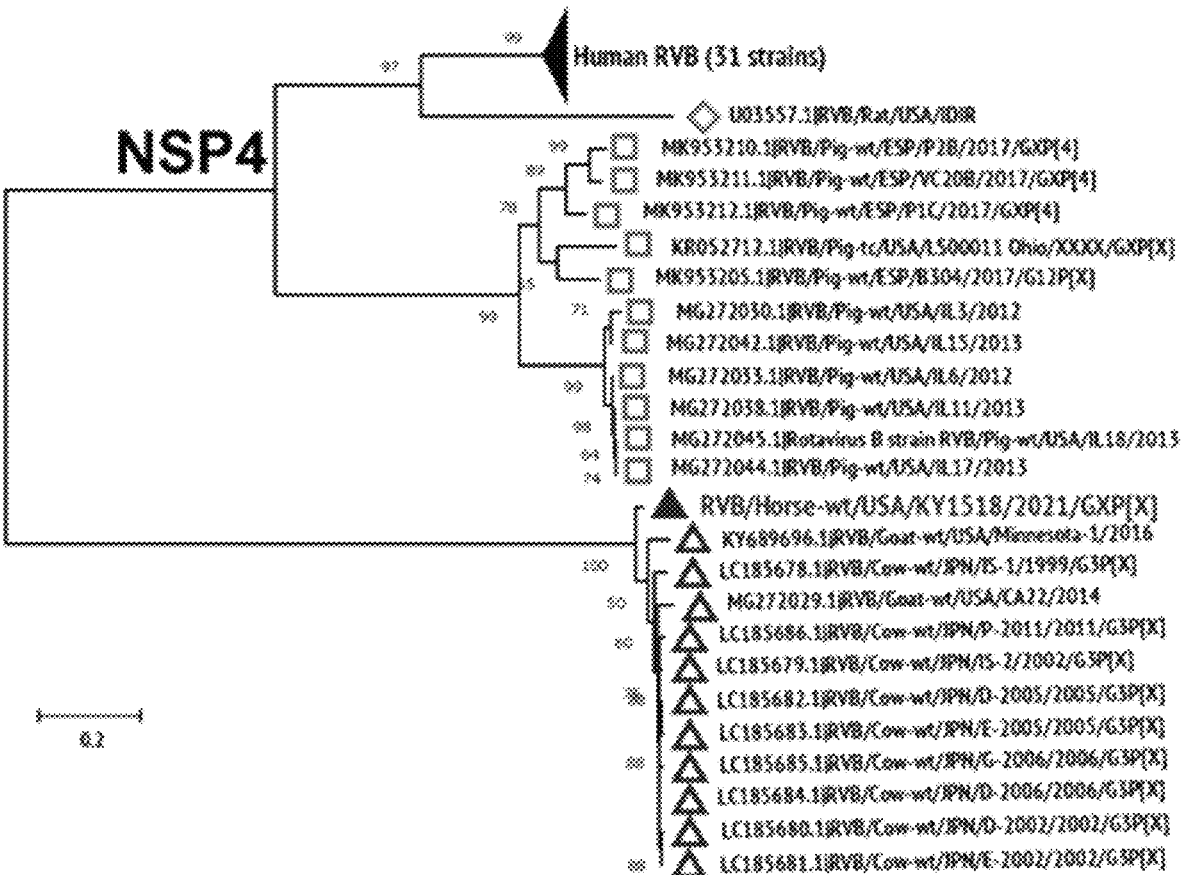
Figure 4E:
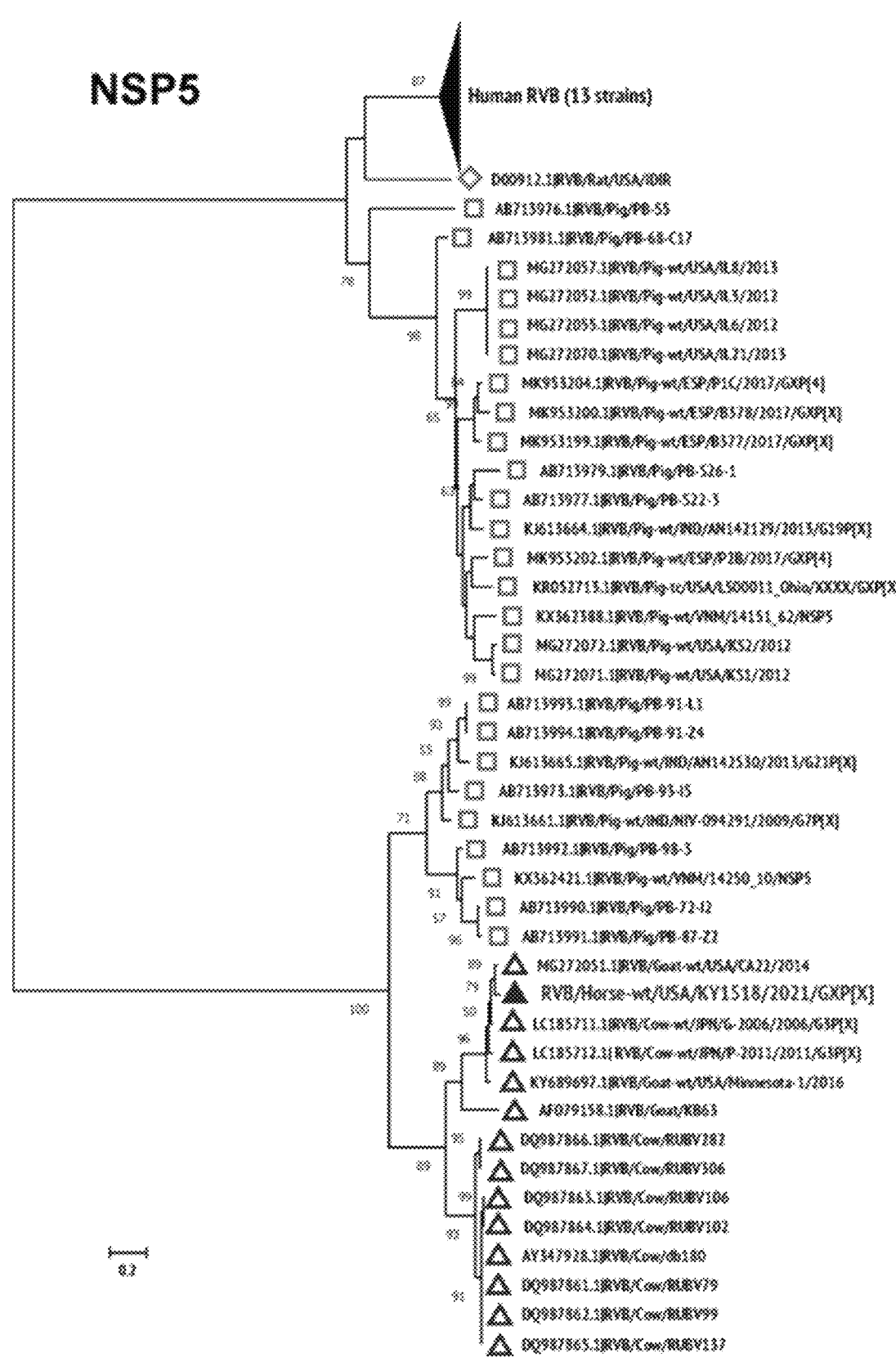

KY/1518/2021 also revealed that all five non-structural proteins (NSP1, NSP2, NSP3, NSP4, and NSP5) clustered more closely with the RVB strains of ruminant origin than with the porcine, murine and human RVB strains, thus supporting the proposition that RVB was transmitted from ruminants to the equine species (FIGS. 4A-E). Among the ruminant RVB strains, the strains from Japan and the USA were phylogenetically closer to RVB/Horse-wt/USA/KY/1518/2021 than the Indian strains (FIGS. 4A, B, and E). The non-structural protein NSP1 protein is the most variable of all the rotavirus proteins and is associated with inhibition of the host antiviral innate immune responses [52]. Here, NSP1 of the equine RVB virus shared a close phylogenetic relationship with caprine RVB strains, RVB/Goat-wt/USA/CA22/2014 and RVB/Goat-wt/USA/Minnesota-1/2016 (FIG. 4A). While NSP3 promotes the translation of viral RNA by inhibiting the host translation machinery, the NSP4 protein is an enterotoxin, which acts as a viroporin and is an important virulence determinant [5]. Both NSP2 and NSP5 are involved in the viroplasm formation and NSP5 interacts with both NSP2 and core replication complex VP2-VP1-VP3 aiding the RNA encapsidation and core assembly during the early replication phase [53]. The non-structural proteins NSP2, NSP3, NSP4, and NSP5 clustered closely with the RVB/Goat-wt/USA/CA22/2014 (FIGS. 4B-E). Overall, the phylogenetic analyses of the gene segments revealed that all 11 segments of RVB/Horse-wt/USA/KY/1518/2021 shared a common ancestor with the bovine and caprine strains originating from the USA, Japan, and India, that agree with our BLAST-based results (Tables 5 and 6).

Detection of Equine Rotavirus Group B by RT-qPCR

A standard RT-qPCR assay targeting the VP7 gene (Assay I) was designed and used to confirm the presence of ERVB in fecal samples derived from outbreaks of foal diarrhea. The detection limit was ~34 copies and the cut-off Ct is 34. Assay I did not detect VP7 gene product of rotavirus group A (simian RVA, SA11 strain), confirming the specificity of the assay (data not shown). The results showed that 23 (23 of 33, 69.69%) samples from diarrheic foals, derived from a total of 18 equine farms, were strongly positive for ERVB, with cycle threshold (Ct) values between 10.65 and 25.68 (Table 7). The fecal samples with higher viral loads (lower Ct values) seemed to come from foals of less than 3 days of age. In contrast, all 9 fecal samples from clinically healthy foals tested negative in the RT-qPCR assay. The VP7 gene-targeting RT-qPCR detection results were further validated by a separate RT-qPCR assay based on the NSP2 gene (Assay II), which are summarized in Table 7. Both assays were in complete agreement in the detection of the ERVB genome in these clinical samples qualitatively as well as quantitatively.

TABLE 7

Detection of ERVB in clinical fecal samples of foals by RT-PCR

| Farm | Foal | Ct (Assay I) | Ct (Assay II) | Age (days) | Clinical status |
|------|------|--------------|---------------|------------|-----------------|
| A | A1 | 20.9 | 21.0 | 3 d | Diarrhea |
|  | A2 | 13.1 | 13.9 | <5 d | Diarrhea |
| B | B1 | 24.5 | 28.8 | 2 d | Diarrhea |
|  | B2 | 18.0 | 19.8 | 2 d | Bloody diarrhea |
|  | B3 | 19.1 | 18.6 | 3 d | Diarrhea |
|  | B4 | 11.6 | 15.1 | 2 d | Diarrhea |
|  | B5 | 23.4 | 28.9 | 2 d | Diarrhea |
| C | C1 | 15.2 | 13.7 | <7 d | Diarrhea |
| D | D1 | 25.6 | 24.0 | <7 d | Diarrhea |
| E | E1 | ND | ND | <7 d | Diarrhea |
| F | F1 | ND | ND | <7 d | Diarrhea |

TABLE 7-continued

Detection of ERVB in clinical fecal samples of foals by RT-PCR

| Farm | Foal | Ct (Assay I) | Ct (Assay II) | Age (days) | Clinical status |
|------|------|--------------|---------------|------------|-----------------|
| G | G1 | ND | ND | <7 d | Diarrhea |
| H | H1 | 15.3 | 16.5 | <5 d | Diarrhea |
|   | H2 | ND | ND | <5 d | Diarrhea |
| I | I1 | 11.3 | 12.7 | <3 d | Diarrhea |
| J | J1 | 17.3 | 17.4 | 3 d | Diarrhea |
|   | J2 | 17.3 | 17.7 | <2 d | Diarrhea |
|   | J3 | 10.6 | 9.6 | <2 d | Diarrhea |
|   | J4 | 13.0 | 11.4 | <3 d | Diarrhea |
|   | J5 | 21.0 | 22.3 | 2 d | Diarrhea |
| K | K1 | 15.0 | 18.2 | <5 d | Diarrhea |
| L | L1 | ND | ND | 1 d | Normal |
|   | L2 | ND | ND | 3 d | Normal |
| M | M1 | ND | ND | <5 d | Normal |
|   | M2 | ND | ND | <5 d | Normal |
|   | M3 | ND | ND | <5 d | Normal |
|   | M4 | ND | ND | <5 d | Normal |
|   | M5 | ND | ND | <5 d | Normal |
| N | N1 | 13.0 | 11.9 | 1 d | Diarrhea |
|   | N2 | 20.1 | 19.1 | 3 d | Diarrhea |
| O | O1 | ND | ND | 12 d | Normal |
| P | P1 | ND | ND | <5 d | Normal |
| Q | Q1 | 15.5 | 15.3 | <7 d | Diarrhea |
| R | R1 | ND | ND | <19 d | Diarrhea |
| S | S1 | ND | ND | 4 d | Diarrhea |
|   | S2 | ND | ND | 4 d | Diarrhea |
|   | S3 | ND | ND | 3 d | Diarrhea |
|   | S4 | 30.3 | 28.1 | 4 d | Mucoid Diarrhea |
| T | T1 | 15.8 | 18.7 | 3 d | Bloody Diarrhea |
|   | T2 | 14.2 | 15.2 | <2 d | Diarrhea |
| U | U1 | ND | ND | <7 d | Diarrhea |
| V | V1 | ND | ND | <2 d | Diarrhea |

Discussion

Rotavirus groups A and B are significant enteric pathogens that cause diarrhea of variable severity in humans and domestic animals [12,16,23]. The horse is a unique species in which only group A rotaviruses are frequently found in diarrhea outbreaks worldwide especially in foals aged 60-90 days [32,42,54]. To date, only one previous study found a single horse testing positive for group B rotavirus (2.7% RVB-positive rate) [43]. Both ERVA G3P[12] and G14P[12] strains have been isolated from samples of affected foals, with some foals co-infected with both strains [37,38]. In this study, we present the first evidence that the rotavirus group B of ruminant-origin has emerged in horses and this novel virus can play an etiological role in outbreaks of diarrhea in neonatal foals, as demonstrated here. Linking rotavirus group B to this highly contagious series of outbreaks of foal diarrhea is also supported by the poor responses of the affected foals to antibiotic treatment, as well as seemingly ineffective vaccinated mare-derived ERVA-specific maternal antibodies in affected foals against this new virus. In this study, ERVB was detected in nearly 70% of foal diarrhea cases. Despite a small sample size, the prevalence of ERVB in diseased foals was similar to that reported in ERVA-associated foal diarrhea outbreaks [26,54-56], highlighting a critical need for further investigation due to the important impact of foal diarrhea on the equine industry.

RVB is genetically and antigenically distinct from RVA. In addition to horses, other established host species for RVB include humans, rats, swine, cattle, lambs, adult sheep, kids, and adult goats [16,27,57-60]. Among RBV of different species, human, porcine, and rat RVB lineages are more related to each other in their respective genome sequences, while RVB lineages from bovines, ovines, and caprines formed a distinctive group [27,45]. Sequence analysis in this study showed that the equine RVB is more closely related to ruminant RVB than to RVB isolates from humans, pigs, and rats. Like RVA, RVB can cause sporadic or epidemic diarrhea in humans and agricultural animals. RVA is thought to be more prevalent than RVB in humans with increased disease severity in infants and higher transmissibility [3]. Nevertheless, RVB appears to be associated with diarrhea in human adults and older children over 15 years of age [16,61,62]. These clinical features are also reproduced in agricultural animal species. For example, group B rotaviruses can cause an epidemic or sporadic diarrhea in both calves and adult cows [19,59]. RVB detection rate in clinical diarrhea samples appears to increase with age in pigs [63,64]. Overall, there has been an upward trend in the frequency of RVB-associated diarrhea outbreaks in farm animals especially piglets [58,65]. Along the same lines, two recent studies demonstrated that 49% and 71% of diarrheic piglets tested positive for RVB, respectively [58,64]. Despite lacking a recent update in small ruminants, RVB was proposed as one of the commonest causes of rotavirus diarrhea in neonatal lambs in England and Wales in the 1980s [60,66]. Widespread RVB infection in domestic animals has been further supported by serological evidence demonstrating a high incidence of RVB infection occurred in some farm animal species (97% for pigs, 71% for bovines, and 91% for small ruminants) [67]. Equine RVB is more closely related to ruminant group B rotaviruses in terms of its genome sequence. Whether equine RVB causes a high incidence of infection and clinical diarrhea in both foals and aged horses similar to what has been observed in RVB infections in ruminants needs to be investigated.

The combination of a large number of sequencing reads and a 69.69% detection rate in clinical samples from diarrheic foals suggests that ERVB is the causative agent for this extensive series of diarrhea outbreaks in neonatal foals. This assumption is also supported by the absence of other significant enteric pathogens in clinical fecal samples, and the rapid course and highly contagious nature of the disease that has been observed, with some farms experiencing a 100% morbidity. Nonetheless, we realize that neonatal foal diarrhea is a complex, multifactorial problem that often involves an interplay among pathogens, host immunity, and environmental factors [68]. In addition, successful recovery of diarrheic foals after medical therapy has prevented us from conducting histopathological studies and characterization of viral replication in the intestinal tract. Further animal challenge experiments and pathogenesis experiments are required to demonstrate the role of ERVB in foal diarrhea and to determine the disease severity and clinical importance of infection in horses.

Numerous studies have shown that group A rotaviruses have a huge potential for cross-species transmission and there were several reports on the emergence of equine-like or bovine/porcine-like rotaviruses in humans [69-73]. As such, zoonotic transmission of animal group A rotaviruses to humans has been widely appreciated in the field and these animal RVs can cause diarrhea in humans, especially in children [21,23]. In contrast, little is known about whether animal group B rotaviruses can jump to and cause diarrhea in humans. In addition, the inter-species transmission of rotavirus B has not been demonstrated previously. The phylogenetic characterization of structural and non-structural gene segments of this novel RVB/Horse-wt/USA/KY/1518/2021 GXP[X] revealed a close association between all 11 segments with those of ruminant RVB strains isolated from the United States, Japan, and India. Interestingly, the equine RVB appears to be more closely related to the caprine and bovine RVB strains in the United States than to strains from the Asian countries. Specifically, VP7 and NSP4 segments of the equine virus (FIGS. 3A-4E) grouped closely with cow strains, while its other 9 segments (FIGS. 2A-4E) related closely to caprine strains. It is possible that a reassortment event between cow and caprine strains may occur, which give rise to this ERVB, and as a result, enable the new virus jump host speices and cause enteric disease in neonatal foals. The work we have presented here suggests for the first case of mammalian-to-mammalian (ruminant-to-equine) host transfer event for RVB, highlighting the similarity between group A and B rotaviruses in terms of their evolution and potential for interspecies transmission. Further investigations are required to determine the zoonotic importance of group B rotaviruses as well as to define viral determinants that promote the emergence of ruminant RVB in horses.

The discovery of a novel group B rotavirus in diarrheic foals of the 2021 foaling season in central Kentucky provides little information about when the virus emerged in horses and whether virus infection might occur in other regions of the USA or in other countries. The widespread, high morbidity of ERVB infection in foals, as demonstrated in this study, may suggest that rotavirus B-associated diarrhea might be happening elsewhere, which warrants further investigation. It is intriguing to note that in the 1995 foaling season in Kentucky, there was a non-A rotavirus-associated diarrhea outbreak in foals reported as 24-48 hours of age that resembled what was observed in this year's outbreaks of foal diarrhea [74]. Samples were tested negative for group A rotavirus, coronavirus, and bacterial pathogens but rotavirus-like particles were visualized in fecal samples by electron microscopy. It should be noted that the 1990s was a decade when numerous cases of group B rotaviruses were detected in farm animals including calves and pigs [19,75]. Hence, it is possible that group B rotavirus may already have been circulating in horses around that time. This speculation seems to be further strengthened by the results of a clinical investigation of RVA, RVB, and RVC in horses in Germany involving samples collected from 1999 to 2013 in which one horse was found RT-PCR positive for rotavirus B [43]. A retrospective study on archived serum and fecal swabs is required to track down when and where this novel virus emerged in horses. In addition, despite the evidence presented in this study pointing out that transmission on the ruminant-equine interface is a probable driver for the observed foal diarrhea outbreak in central Kentucky, natural spillover from an unknown intermediate host such as wildlife species e.g. deer, should be included in parallel in establishing the origin of ERVB-associated foal diarrhea.

In summary, we identified a novel group B rotavirus that was associated with a widespread problem of diarrhea in neonatal foals.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Troeger C, Khalil I A, Rao P C, et al. Rotavirus Vaccination and the Global Burden of Rotavirus Diarrhea Among Children Younger Than 5 Years. JAMA pediatrics. 2018 Oct. 1; 172(10):958-965.

2. Dhama K, Chauhan R S, Mahendran M, et al. Rotavirus diarrhea in bovines and other domestic animals. Vet Res Commun. 2009 January; 33(1):1-23.

3. Anderson E J, Weber S G. Rotavirus infection in adults. Lancet Infect Dis. 2004 February; 4(2):91-9.

4. Crawford S E, Ramani S, Tate J E, et al. Rotavirus infection. Nat Rev Dis Primers. 2017 Nov. 9; 3(1):17083.

5. Hu L, Crawford S E, Hyser J M, et al. Rotavirus non-structural proteins: structure and function. Curr Opin Virol. 2012 August; 2(4):380-8.

6. Trojnar E, Otto P, Roth B, et al. The genome segments of a group D rotavirus possess group A-like conserved termini but encode group-specific proteins. J Virol. 2010 October; 84(19):10254-65.

7. Zhang X, Settembre E, Xu C, et al. Near-atomic resolution using electron cryomicroscopy and single-particle reconstruction. 2008; 105(6):1867-1872.

8. Tang B, Gilbert J M, Matsui S M, et al. Comparison of the rotavirus gene 6 from different species by sequence analysis and localization of subgroup-specific epitopes using site-directed mutagenesis. Virology. 1997 Oct. 13; 237(1):89-96.

9. Matthijnssens J, Otto P H, Ciarlet M, et al. VP6-sequence-based cutoff values as a criterion for rotavirus species demarcation. Arch Virol. 2012 June; 157(6):1177-82.

10. Walker P J, Siddell S G, Lefkowitz E J, et al. Changes to virus taxonomy and the International Code of Virus Classification and Nomenclature ratified by the International Committee on Taxonomy of Viruses (2019). Arch Virol. 2019 September; 164(9):2417-2429.

11. Hoshino Y, Kapikian A Z. Classification of rotavirus VP4 and VP7 serotypes. Archives of virology Supplementum. 1996; 12:99-111.

12. van der Heide R, Koopmans M P, Shekary N, et al. Molecular characterizations of human and animal group a rotaviruses in the Netherlands. J Clin Microbiol. 2005 February; 43(2):669-75.

13. Steele A, Geyer A, Gerdes G, et al. Infectious diseases of livestock. Eds) Coetzer J A W and Tustin R C, Oxford University Press, Southern Africa. 2004:1256-64.

14. Trovao N S, Shepherd F K, Herzberg K, et al. Evolution of rotavirus C in humans and several domestic animal species. Zoonoses Public Health. 2019 August; 66(5): 546-557.

15. Deol P, Kattoor J J, Sircar S, et al. Avian Group D Rotaviruses: Structure, Epidemiology, Diagnosis, and Perspectives on Future Research Challenges. Pathogens. 2017 Oct. 24; 6(4):53.

16. Sanekata T, Ahmed M U, Kader A, et al. Human group B rotavirus infections cause severe diarrhea in children and adults in Bangladesh. J Clin Microbiol. 2003 May; 41(5):2187-90.

17. Tao H, Changan W, Zhaoying F, et al. Waterborne Outbreak of Rotavirus Diarrhoea in Adults in China Caused by a Novel Rotavirus. The Lancet. 1984; 323 (8387):1139-1142.

18. Chen G-M, Hung T, Bridger J C, et al. Chinese Adult Rotavirus Is a Group B Rotavirus. The Lancet. 1985; 326(8464):1123-1124.

19. Chang K O, Parwani A V, Smith D, et al. Detection of group B rotaviruses in fecal samples from diarrheic calves and adult cows and characterization of their VP7 genes. J Clin Microbiol. 1997 August; 35(8):2107-10.

20. Nguyen T A, Khamrin P, Trinh Q D, et al. Sequence analysis of Vietnamese P[6] rotavirus strains suggests evidence of interspecies transmission. J Med Virol. 2007 December; 79(12):1959-65.

21. Cook N, Bridger J, Kendall K, et al. The zoonotic potential of rotavirus. J Infect. 2004 May; 48(4):289-302.

22. Muller H, Johne R. Rotaviruses: diversity and zoonotic potential—a brief review. Berl Munch Tierarztl Wochenschr. 2007 March-April; 120(3-4):108-12.

23. Martella V, Banyai K, Matthijnssens J, et al. Zoonotic aspects of rotaviruses. Vet Microbiol. 2010 Jan. 27; 140 (3-4):246-55.

24. Mukherjee A, Mullick S, Deb A K, et al. First report of human rotavirus G8P[4] gastroenteritis in India: evidence of ruminants-to-human zoonotic transmission. J Med Virol. 2013 March; 85(3):537-45.

25. Mukherjee A, Dutta D, Ghosh S, et al. Full genomic analysis of a human group A rotavirus G9P[6] strain from Eastern India provides evidence for porcine-to-human interspecies transmission. Arch Virol. 2009; 154(5):733-46.

26. Komoto S, Tacharoenmuang R, Guntapong R, et al. Reassortment of Human and Animal Rotavirus Gene Segments in Emerging DS-1-Like G1P[8] Rotavirus Strains. PLoS One. 2016; 11(2):e0148416.

27. Chen F, Knutson T P, Ciarlet M, et al. Complete genome characterization of a rotavirus B (RVB) strain identified in Alpine goat kids with enteritis reveals inter-species transmission with RVB bovine strains. J Gen Virol. 2018 April; 99(4):457-463.

28. Mino S, Adúriz M, Barrandeguy M, et al. Molecular Characterization of Equine Rotavirus Group A Detected in Argentinean Foals During 2009-2014. Journal of Equine Veterinary Science. 2017 2017 Dec. 1; 59:64-70.

29. Hoshino Y, Wyatt R G, Greenberg H B, et al. Serotypic similarity and diversity of rotaviruses of mammalian and avian origin as studied by plaque-reduction neutralization. J Infect Dis. 1984 May; 149(5):694-702.

30. Browning G F, Fitzgerald T A, Chalmers R M, et al. A novel group A rotavirus G serotype: serological and genomic characterization of equine isolate FI23. J Clin Microbiol. 1991 September; 29(9):2043-6.

31. Imagawa H, Tanaka T, Sekiguchi K, et al. Electropherotypes, serotypes, and subgroups of equine rotaviruses isolated in Japan. Arch Virol. 1993; 131(1-2):169-76.

32. Isa P, Wood A R, Netherwood T, et al. Survey of equine rotaviruses shows conservation of one P genotype in background of two G genotypes. Arch Virol. 1996; 141 (9):1601-12.

33. Imagawa H, Ishida S, Uesugi S, et al. Genetic analysis of equine rotavirus by RNA-RNA hybridization. J Clin Microbiol. 1994 August; 32(8):2009-12.

34. Browning G F, Chalmers R M, Fitzgerald T A, et al. Serological and genomic characterization of L338, a novel equine group A rotavirus G serotype. J Gen Virol. 1991 May; 72 (Pt 5):1059-64.

35. Hardy M E, Gorziglia M, Woode G N. The outer capsid protein VP4 of equine rotavirus strain H-2 represents a unique VP4 type by amino acid sequence analysis. Virology. 1993 March; 193(1):492-7.

36. Isa P, Snodgrass D R. Serological and genomic characterization of equine rotavirus VP4 proteins identifies three different P serotypes. Virology. 1994 June; 201(2):364-72.

37. Collins P J, Cullinane A, Martella V, et al. Molecular characterization of equine rotavirus in Ireland. J Clin Microbiol. 2008 October; 46(10):3346-54.

38. Carossino M, Barrandeguy M E, Li Y, et al. Detection, molecular characterization and phylogenetic analysis of G3P[12] and G14P[12] equine rotavirus strains co-circulating in central Kentucky. Virus Res. 2018 Aug. 15; 255:39-54.

39. Athiyyah A F, Utsumi T, Wahyuni R M, et al. Molecular Epidemiology and Clinical Features of Rotavirus Infection Among Pediatric Patients in East Java, Indonesia During 2015-2018: Dynamic Changes in Rotavirus Genotypes From Equine-Like G3 to Typical Human G1/G3 [Original Research]. Front Microbiol. 2019 2019 May 3; 10(940):940.

40. Ghosh S, Shintani T, Kobayashi N. Evidence for the porcine origin of equine rotavirus strain H-1. Vet Microbiol. 2012 Aug. 17; 158(3-4):410-4.

41. Mino S, Matthijnssens J, Badaracco A, et al. Equine G3P[3] rotavirus strain E3198 related to simian RRV and feline/canine-like rotaviruses based on complete genome analyses. Vet Microbiol. 2013 Jan. 25; 161(3-4):239-46.

42. Bailey K E, Gilkerson J R, Browning G F. Equine rotaviruses—current understanding and continuing challenges. Vet Microbiol. 2013 Nov. 29; 167(1-2):135-44.

43. Otto P H, Rosenhain S, Elschner M C, et al. Detection of rotavirus species A, B and C in domestic mammalian animals with diarrhoea and genotyping of bovine species A rotavirus strains. Vet Microbiol. 2015 Sep. 30; 179(3-4):168-76.

44. Kumar S, Stecher G, Li M, et al. MEGA X: Molecular Evolutionary Genetics Analysis across Computing Platforms. Mol Biol Evol. 2018 Jun. 1; 35(6):1547-1549.

45. Shepherd F K, Herrera-Ibata D M, Porter E, et al. Whole Genome Classification and Phylogenetic Analyses of Rotavirus B strains from the United States. Pathogens. 2018 Apr. 18; 7(2):44.

46. Lu X, McDonald S M, Tortorici M A, et al. Mechanism for coordinated RNA packaging and genome replication by rotavirus polymerase VP1. Structure. 2008 Nov. 12; 16(11):1678-88.

47. McDonald S M, Patton J T. Rotavirus VP2 core shell regions critical for viral polymerase activation. J Virol. 2011 April; 85(7):3095-105.

48. Patton J T, Chen D. RNA-binding and capping activities of proteins in rotavirus open cores. J Virol. 1999 February; 73(2):1382-91.

49. Diaz-Salinas M A, Romero P, Espinosa R, et al. The Spike Protein VP4 Defines the Endocytic Pathway Used by Rotavirus To Enter MA104 Cells. 2013; 87(3):1658-1663.

50. Lopez S, Arias C F. Multistep entry of rotavirus into cells: a Versaillesque dance. Trends Microbiol. 2004 June; 12(6):271-8.

51. Greenberg H B, Estes M K. Rotaviruses: from pathogenesis to vaccination. Gastroenterology. 2009 May; 136 (6):1939-51.

52. Barro M, Patton J T. Rotavirus NSP1 inhibits expression of type I interferon by antagonizing the function of interferon regulatory factors IRF3, IRF5, and IRF7. J Virol. 2007 May; 81(9):4473-81.

53. Eichwald C, Rodriguez J F, Burrone O R. Characterization of rotavirus NSP2/NSP5 interactions and the dynamics of viroplasm formation. J Gen Virol. 2004 March; 85(Pt 3):625-634.

54. Elschner M, Schrader C, Hotzel H, et al. Isolation and molecular characterisation of equine rotaviruses from Germany. Vet Microbiol. 2005 Jan. 31; 105(2):123-9.

55. Browning G F, Begg A P. Prevalence of G and P serotypes among equine rotaviruses in the faeces of diarrhoeic foals. Arch Virol. 1996 1996 Jun. 1; 141(6): 1077-89.

56. Tsunemitsu H, Imagawa H, Togo M, et al. Predominance of G3B and G14 equine group A rotaviruses of a single VP4 serotype in Japan. Arch Virol. 2001 October; 146 (10):1949-62.

57. Eiden J J, Nataro J, Vonderfecht S, et al. Molecular cloning, sequence analysis, in vitro expression, and immunoprecipitation of the major inner capsid protein of the IDIR strain of group B rotavirus (GBR). Virology. 1992 June; 188(2):580-9.

58. Miyabe F M, Dall Agnol A M, Leme R A, et al. Porcine rotavirus B as primary causative agent of diarrhea outbreaks in newborn piglets. Sci Rep. 2020 Dec. 15; 10(1): 22002.

59. Hayashi M, Murakami T, Kuroda Y, et al. Reinfection of adult cattle with rotavirus B during repeated outbreaks of epidemic diarrhea. Can J Vet Res. 2016 July; 80(3):189-96.

60. Theil K W, Grooms D L, McCloskey C M, et al. Group B rotavirus associated with an outbreak of neonatal lamb diarrhea. J Vet Diagn Invest. 1995 January; 7(1):148-50.

61. Joshi M S, Ganorkar N N, Ranshing S S, et al. Identification of group B rotavirus as an etiological agent in the gastroenteritis outbreak in Maharashtra, India. J Med Virol. 2017 December; 89(12):2244-2248.

62. Krishnan T, Sen A, Choudhury J S, et al. Emergence of adult diarrhoea rotavirus in Calcutta, India. Lancet. 1999 Jan. 30; 353(9150):380-1.

63. Kuga K, Miyazaki A, Suzuki T, et al. Genetic diversity and classification of the outer capsid glycoprotein VP7 of porcine group B rotaviruses. Arch Virol. 2009 2009 Oct. 11; 154(11):1785-95.

64. Marthaler D, Rossow K, Gramer M, et al. Detection of substantial porcine group B rotavirus genetic diversity in the United States, resulting in a modified classification proposal for G genotypes. Virology. 2012 Nov. 10; 433 (1):85-96.

65. Alekseev K P, Penin A A, Mukhin A N, et al. Genome Characterization of a Pathogenic Porcine Rotavirus B Strain Identified in Buryat Republic, Russia in 2015. Pathogens. 2018 Apr. 20; 7(2):46.

66. Papp H, Malik Y S, Farkas S L, et al. Rotavirus strains in neglected animal species including lambs, goats and camelids. Virusdisease. 2014; 25(2):215-22.

67. Holland R E. Some infectious causes of diarrhea in young farm animals. 1990; 3(4):345-375.

68. Magdesian K G. Neonatal foal diarrhea. Vet Clin North Am Equine Pract. 2005 August; 21(2):295-312, vi.

69. Arana A, Montes M, Jere K C, et al. Emergence and spread of G3P[8] rotaviruses possessing an equine-like VP7 and a DS-1-like genetic backbone in the Basque Country (North of Spain), 2015. Infect Genet Evol. 2016 October; 44:137-144.

70. Cowley D, Donato C M, Roczo-Farkas S, et al. Emergence of a novel equine-like G3P[8] inter-genogroup reassortant rotavirus strain associated with gastroenteritis in Australian children. J Gen Virol. 2016 February; 97(2): 403-410.

71. Perkins C, Mijatovic-Rustempasic S, Ward M L, et al. Genomic Characterization of the First Equine-Like G3 [8] Rotavirus Strain Detected in the United States. Genome Announc. 2017 Nov. 22; 5(47):e01341-17.

72. Martella V, Colombrita D, Lorusso E, et al. Detection of a porcine-like rotavirus in a child with enteritis in Italy. J Clin Microbiol. 2008 October; 46(10):3501-7.

73. Jeong S, Than V T, Lim I, et al. Whole-genome analysis of a rare human Korean G3P rotavirus strain suggests a complex evolutionary origin potentially involving reassortment events between feline and bovine rotaviruses. PLoS One. 2014; 9(5):e97127.

74. Dwyer R M. Diarrhea among young foals. Equine Disease Quarterly. 1995, July; 3(4):5-6.

75. Vlasova A N, Amimo J O, Saif L J. Porcine Rotaviruses: Epidemiology, Immune Responses and Control Strategies. Viruses. 2017 Mar. 18; 9(3):48.

76. Marthaler D, Suzuki T, Rossow K, et al. VP6 genetic diversity, reassortment, intragenic recombination and classification of rotavirus B in American and Japanese pigs. Vet Microbiol. 2014 Aug. 27; 172(3-4):359-66.

77. World Health Organization. (2009). Manual of rotavirus detection and characterization methods. World Health Organization. https://apps.who.int/iris/handle/10665/70122

78. Freeman M M, Kerin T, Hull J, McCaustland K, Gentsch J. Enhancement of detection and quantification of rotavirus in stool using a modified real-time R T-PCR assay. J Med Virol. 2008 August; 80(8):1489-96. doi: 10.1002/jmv.21228. PMID: 18551614.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

What is claimed is:

1. A method for detecting equine rotavirus group B (ERVB) in an equine biological sample, the method comprising:

extracting viral ribonucleic acid (RNA) from the sample;

performing polymerase chain reaction (PCR) analysis on a VP7 segment of ERVB using a primer and probe set comprising SEQ ID NOs: 210, 211, and 212; and determining whether the sample contains ERVB based on signal generated during amplification.

2. The method of claim 1, wherein the equine biological sample is a fecal sample.

3. The method of claim 1, wherein said primer and probe set exhibits no amplification of porcine or bovine RVB VP7 sequences under assay conditions.

4. The method of claim 1, wherein the polymerase chain reaction (PCR) analysis is a real-time quantitative reverse transcription polymerase chain reaction (qRT-PCR).

* * * * *